United States Patent [19]

Tsuchiya et al.

[11] Patent Number: 5,306,728
[45] Date of Patent: Apr. 26, 1994

[54] SUBSTITUTED AMINE DERIVATIVES HAVING ANTIHYPERLIPEMIA ACTIVITY

[75] Inventors: Yoshimi Tsuchiya; Takashi Nomoto; Masahiro Hayashi; Yoshikazu Iwasawa; Hitoshi Masaki; Mitsuru Ohkubo; Yumiko Sakuma; Yasufumi Nagata; Toshihiko Satoh; Toshio Kamei, all of Tokyo, Japan

[73] Assignee: Banyu Pharmaceutical Co., Ltd., Tokyo, Japan

[21] Appl. No.: 26,120

[22] Filed: Mar. 4, 1993

Related U.S. Application Data

[63] Continuation of Ser. No. 672,430, Mar. 20, 1991, abandoned.

[30] Foreign Application Priority Data

Mar. 20, 1990 [JP] Japan .................. 2-71542
Apr. 3, 1990 [JP] Japan .................. 2-88624

[51] Int. Cl.$^5$ .................. A61K 31/38; A01N 43/06; C07D 411/10; C07D 333/10
[52] U.S. Cl. .................. 514/438; 514/445; 549/59; 549/65; 549/75; 549/77; 544/182; 544/216; 544/333; 544/357; 544/405; 546/284; 546/329; 546/339; 548/205; 548/214; 548/235; 548/247
[58] Field of Search .................. 549/59, 65, 75, 77; 514/438, 445

[56] References Cited

U.S. PATENT DOCUMENTS 3,639,476 2/1972 Eberle et al. .................. 514/438

FOREIGN PATENT DOCUMENTS 0318860 7/1989 European Pat. Off. .
0395768 7/1990 European Pat. Off. .

OTHER PUBLICATIONS

Fessenden et al., Organic Chemistry, 2nd ed. (1982) pp. 714–715.
Chemical Abstracts 113(19):171, 868 (Takezawa) Abstract of WO90/05,132 (1990).
Chemical Abstracts 113(23):211,837 (Tsucha) Abstract of JP Koho 02,169,571 (1990).

(List continued on next page.)

Primary Examiner—Mukund J. Shah
Assistant Examiner—Matthew V. Grumbling
Attorney, Agent, or Firm—Sherman & Shalloway

[57] ABSTRACT

Substituted amine derivatives represented by the general formula $$R-Q-CH_2-\underset{R^1}{\overset{R^1}{N}}-CH_2-\underset{R^3}{\overset{R^2}{C}}-\underset{R^5}{\overset{R^4}{C}}-\overset{R^6}{C}=\overset{R^7}{C}-\underset{R^{10}}{\overset{R^8}{C}}-R^9 \quad [I]$$

wherein Q is -C-D-E- F-G-M- or -N-H-I-J-K-L- [C, D, E, F, G, H, I, J, K and L are each O, S, a carbonyl group, -CHR$^2$-, -R$^b$= or -NR$^c$- (R$^a$, R$^b$ and R$^c$ are each H or a lower alkyl group), M and N are each an aromatic ring of 5-6 members optionally having a halogen, OH, LN, a lower alkyl group or a lower alkoxy group, provided that L is not O, S, or -NR$^c$-]; R is a heterocyclic ring of 5-6 members; R$^1$ is H, a lower alkyl group, a lower haloalkyl group, a lower alkenyl group, a lower alkynyl group or a cycloalkyl group; R$^2$, R$^3$, R$^4$, R$^5$ R$^6$ and R$^7$ are each H, a halogen or a lower alkyl group or two of them denote a single bond; R$^8$ and R$^9$ are each F, CF$_3$ or a lower alkyl group or are a cycloalkane in combination thereof; and R$^{10}$ is H, F, CF$_3$ an acetoxy group, a lower alkyl group or a lower alkoxy group. These compounds inhibit biosynthesis of cholesterol in mammals by inhibiting their squalene epoxidase, and thereby lower their blood cholesterol values. Therefore, these compounds are expected to be effective as an agent for treatment and prophylaxis of diseases caused by excess of cholesterol, for example, obesity, hyperlipemia and arteriosclerosis and heart and encephalic diseases accompanying them.

13 Claims, No Drawings

OTHER PUBLICATIONS

Chemical Abstracts 114(3):17 392z (Tsuchiya) Abstract of J. Biol. Chem 1990 265(30) 18075-18078.

Chemical Abstracts 115(9):85181a (Hidaka) Abstracts of J. Biol. Chem. 1991 266(20) 13171-13177.

Chemical Abstracts 99(25)212,414 (Stuetz) Abstract of DE 3,302,814; (Feb. 1982).

Chemical Abstracts 100(11) 85,436c (Stuetz) Abstract of DE 3,316,093; (May 1982).

Chemical Abstracts 105(21)190,645 (Stuetz) Abstract of CH 656 378 (May. 1983).

Chemical Abstracts 111(25) 232,287 (Takezawa) Abstract of EP 318 860 (1989).

JP-A-03 141 275, Patent Abstracts of Japan, vol. 15, No. 357 (C-866), Sep. 10, 1991, "Substituted Allylamine Derivative and its Use", Banyu Pharmaceut Co. Ltd.

SUBSTITUTED AMINE DERIVATIVES HAVING ANTIHYPERLIPEMIA ACTIVITY

This application is a continuation of application Ser. No. 07/672,430, filed Mar. 20, 1991, now abandoned.

DETAILED DESCRIPTION OF THE INVENTION

This invention relates to novel substituted amine derivatives, and more detailedly relates to substituted amine derivatives and their contoxic salts useful in the medicinal field, particularly in the field of treatment and prophylaxis of hypercholesterolemia, hyperlipemia and arteriosclerosis, and their preparation method and their use.

Recently, increase of occurrence frequency of arteriosclerosis and various coronary and encephalic artery system diseases following it, due to aging of the population and change of food, life, etc., have been pointed out. Various factors were considered as stimulants of arteriosclerosis, and particularly, increase of blood cholesterol is one of the most dangerous factors. Thus, blood cholesterol-lowering agents are effective for prophylaxis and treatment of arteriosclerosis (Agents Used to Treat Hyperlipidemia, Drug Evaluations 6th. edition 903–926 (1986)). Further, among these blood cholesterol-lowering agents, agents which inhibit biosynthesis of cholesterol in the living body are highly rated due to their clear action mechanism and strong drug action (Proc. Natl. Acad. Sci., 77, 3957 (1980)). However, since many of the so far known cholesterol biosynthesis-inhibiting agents are inhibitors in the early stage or later stage of the cholesterol biosynthesis steps, there are problems, for example, that, when they inhibit biosynthesis of cholesterol, they simultaneously inhibit formation of various other physiologically important biological products, and further accumulation of precursors formed by the inhibition becomes a cause of other diseases.

Previously, the present inventors reported that a series of substituted allylamine derivatives selectively inhibit squalene epoxidase positioned at the middle stage of the cholesterol biosynthesis system of mammals, and therefore are useful as a blood cholesterol-lowering agent having a different action mechanism from the known cholesterol biosynthesis-inhibiting agents (See =Japanese Patent Application No. 296840/1988, EP-A-318860, WO 90/5132 (PCT/JP89/00522)). As for inhibitors of mammal squalene epoxidase, several reports were made lately besides those by the present inventors, but any of the compounds described therein only has a very low activity (J. Chem. Research(s) 18-19 (1988); J. Am. Chem. Soc., 111, 1508-1510 (1989); J. Med. Chem., 32, 2152-2158 (1989); Japanese Laid-Open Patent Publication No. 3144/1989).

The major object of the invention is to provide an antihypercholesterolemia agent, an antihyperlipemia agent and an agent for the treatment and prophylaxis of arteriosclerosis each having higher safety and excellent anticholesterol action, compared to the known drugs.

As described above, the present inventors previously reported that a series of substituted allylamine derivatives selectively inhibit mammal squalene epoxidase and have a strong anticholesterol action (Japanese Patent Application No. 296840/1988, EP-A-318860 and WO 90/5132 (PCT/JP 89/0052)).

This time, as a result of vigorous study, it was found that the substituted amine derivatives represented by the following general formula [I] have further excellent characteristics compared to the group of the previously reported compounds, and the present invention was completed.

Thus, according to the invention, substituted amine derivatives represented by the following general formula and their nontoxic salts are provided:

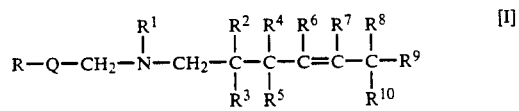

wherein,

R denotes a 5- or 6-membered heterocyclic group containing 1 to 4 hetero atoms selected from the group consisting of nitrogen atom(s), oxygen atom(s) and sulfur atom(s);

Q denotes (a) a group represented by the formula:

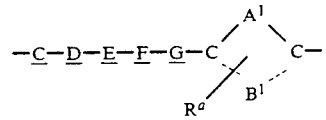

wherein C, D, E, F and G are the same or different and each denotes an oxygen atom, sulfur atom, carbonyl group, group represented by the formula $-CHR^b-$, group represented by the formula $-CR^c=$ or group represented by the formula $-NR^d-$, wherein $R^b$, $R^c$ and $R^d$ are the same or different and each denotes a hydrogen atom or lower alkyl group; $A^1$ denotes a methine group, nitrogen atom, oxygen atom or sulfur atom; $B^1$ denotes a group which may contain one or two hetero atoms selected from the group consisting of nitrogen atom(s), oxygen atom(s) and sulfur atom(s) and forms a 5- or 6- membered aromatic ring together with the adjacent carbon atoms and $A^1$; and $12^1$ denotes a hydrogen atom, halogen atom, hydroxyl group, cyano group, lower alkyl group or lower alkoxy group, provided that except that each pair of $\underline{C}$ and $\underline{F}$, $\underline{C}$ and $\underline{G}$, or $\underline{D}$ and $\underline{G}$ are the same or different and can denote oxygen atom(s), sulfur atom(s) or group(s) represented by the formula $-NR^d-$, it is impossible that at least two of $\underline{C}$, $\underline{D}$, $\underline{E}$, $\underline{F}$ and $\underline{G}$ simultaneously denote oxygen atom(s), sulfur atom(s) or group(s) represented by the formula $-NR^d$, and it is impossible that at least two of $\underline{C}$, $\underline{D}$, $\underline{E}$, $\underline{F}$ and $\underline{G}$ simultaneously denote carbonyl groups, and further when double bond(s) and oxygen atom(s), sulfur atom(s) or group(s) represented by the formula $-NR^d-$coexist in the chain formed by $\underline{C}$, $\underline{D}$, $\underline{E}$, $\underline{F}$ and $\underline{G}$, they do not adjoin one another, or (b) a group represented by the formula:

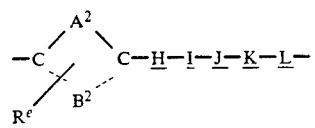

wherein $A^2$ denotes a methine group, nitrogen atom, oxygen atom or sulfur atom; $B^2$ denotes a group which may contain one or two hetero atoms selected from the group consisting of nitrogen atom(s), oxygen atom(s)

and sulfur atom(s) and forms a 5- or 6-membered aromatic ring together with the adjacent carbon atoms and $A^2$; $\underline{H}$, $\underline{I}$, $\underline{J}$ and $\underline{K}$ are the same or different and each denotes an oxygen atom, sulfur atom, carbonyl group, group represented by the formula —CHR$^f$—, group represented by the formula —CR$^g$= or group represented by the formula —NR$^h$—, wherein R$^f$, R$^g$ and R$^h$ are the same or different and each denotes a hydrogen atom or lower alkyl group; $\underline{L}$ denotes a carbonyl group, group represented by the formula —CHR$^i$—or group represented by the formula —CR$^j$=, wherein R$^i$ and R$^j$ are the same or different and each denotes a hydrogen atom or lower alkyl group; and R$^e$ denotes a hydrogen atom, halogen atom, hydroxyl group, cyano group, lower alkyl group or lower alkoxy group, provided that except that $\underline{H}$ and $\underline{K}$ are the same or different and each can denote an oxygen atom, sulfur atom or group represented by the formula —NR$^h$—, it is impossible that at least two of $\underline{H}$, $\underline{I}$, $\underline{J}$ and $\underline{K}$ simultaneously denote oxygen atom(s), sulfur atom(s) or group(s) represented by the formula —NR$^h$—, and it is impossible that at least two of $\underline{H}$, $\underline{I}$, $\underline{J}$ and $\underline{K}$ simultaneously denote carbonyl groups, and further when double bond(s) and oxygen atom(s), sulfur atom(s) or group(s) represented by the formula —NR$^h$—coexist in the chain formed by $\underline{H}$, $\underline{I}$, $\underline{J}$, $\underline{K}$ and $\underline{L}$, they do not adjoin one another;

$R^1$ denotes a hydrogen atom, lower alkyl group, lower haloalkyl group, lower alkenyl group, lower alkynyl group or cycloalkyl group;

$R^2$, $R^3$, $R^4$ and $R^5$ are the same or different and each denotes a hydrogen atom, halogen atom or lower alkyl group, or $R^2$ and $R^4$ and/or $R^3$ and $R^5$ combine to denote a single bond;

$R^6$ and $R^7$ are the same or different and each denotes a hydrogen atom, halogen atom or lower alkyl group, or $R^6$ and $R^7$ combine to denote a single bond;

$R^8$ and $R^9$ are the same or different and each denotes a fluorine atom, trifluoromethyl group or lower alkyl group, or $R^8$ and $R^9$ combine to denote a group to form cycloalkane together with the adjacent carbon atom;

$R^{10}$ denotes a hydrogen atom, fluorine atom, trifluoromethyl group, acetoxy group, lower alkyl group or lower alkoxy group.

Compounds of the above formula [I] in the invention inhibit mammal squalene epoxidase extremely selectively and strongly and are useful as a drug for prophylaxis or treatment of hypercholesterolemia, hyperlipemia, arteriosclerosis, etc.

Described below are definitions of various terms referred to in the description of this specification and their specific examples:

The term "lower" is used to mean that the carbon number of the group or compound to which this term is attached is 6 or less, preferably 5 or less.

Thus, a lower alkyl group includes a straight-chain or branched alkyl group having 1 to 6, preferably 1 to 3 carbon atoms such as a methyl, ethyl, propyl, isopropyl, butyl, isobutyl, sec-butyl, tert-butyl, pentyl, isopentyl, neopentyl or hexyl group; a lower haloalkyl group includes a haloalkyl group having 1 to 3 halogen atoms and 1 to 4 carbon atoms such as a trifluoromethyl, 2-fluoroethyl, 2-chloroethyl, 2,2,2-trifluoroethyl, 3-fluoropropyl or 2-fluoro-2-methylpropyl, 4-fluorobutyl group; a lower alkenyl group includes a straight-chain or branched alkenyl group having 3 to 5 carbon atoms such as an allyl, 2-methyl-2-propenyl, 2-butenyl, 3-butenyl or 2-pentenyl group; a lower alkynyl group includes a straight-chain or branched alkynyl group having 3 to 5 carbon atoms such as a propargyl, 2-butynyl, 3-butynyl, 1-methyl-2-butynyl or 2-pentynyl group; and a lower alkoxy group includes straight-chain or branched alkoxy group having 1 to 5 carbon atoms such as a methoxy, ethoxy, propoxy, isopropoxy, butoxy, isobutoxy, sec-butoxy, tert-butoxy or pentoxy group.

A cycloalkyl group and a cycloalkane include a cycloalkyl group and a cycloalkane each having 3 to 6 carbon atoms, respectively, and specifically, examples of the cycloalkyl group are cyclopropyl, cyclobutyl, cyclopentyl and cyclohexyl groups and examples of the cycloalkane are cyclopropane, cyclobutane, cyclopentane and cyclohexane.

Halogen atoms include fluorine, chlorine, bromine and iodine atoms.

In order to further specifically disclose compounds of the invention represented by the above general formula [I], the various symbols used in the formula [I]are further detailedly described mentioning their preferred specific examples:

Examples of the 5- or 6- membered hetero cyclic group, symbolized by R, containing 1 to 4 hetero atoms selected from the group consisting of nitrogen atom(s), oxygen atom(s) and sulfur atom(s) include pyrrolyl, furyl, thienyl, oxazolyl, isoxazolyl, thiazolyl, isothiazolyl, imidazolyl, pyrazolyl, oxadiazolyl, thiadiazolyl, triazolyl, tetrazolyl, furazanyl, pyridyl, pyridazinyl, pyrimidinyl, pyrazinyl and triazinyl groups and other aromatic heterocyclic groups; and dihydrothienyl, tetrahydrothienyl, pyrrolinyl, pyrrolidinyl, oxazolinyl, oxazolidinyl, isoxazolinyl, isoxazolidinyl, thiazolinyl, thiazolidinyl, isothiazolinyl, isothiazolidinyl, 1, 2-dithiolanyl, 1, 3-dithiolanyl, 1, 2-dithiolyl, 1, 3-dithiolyl, dihydrothiopyranyl, tetrahydrothiopyranyl, 1, 4-dithianyl, 1, 4-dithiinyl, 1, 4-oxathiinyl and thiomorpholinyl groups and other nonaromatic heterocyclic groups. Among them, preferred are thienyl, pyrrolyl, oxazolyl, isoxazolyl, thiazolyl, isothiazolyl, imidazolyl, pyridyl and dihydrothienyl groups, etc., and particularly preferred are 3-thienyl, 1-pyrrolyl, 5-oxazolyl, 4-isoxazolyl, 5-isoxazolyl, 4-thiazolyl, 5-thiazolyl, 3-isothiazolyl, 4-isothiazolyl, 5-isothiazolyl, 3-pyridyl, 2, 3-dihydro-4-thienyl and 2, 5-dihydro-3-thienyl groups, etc.

In the group symboled by R and represented by (a) the formula:

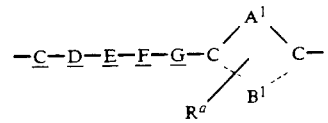

or (b) the formula:

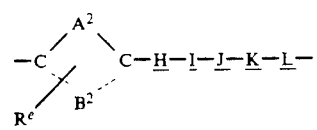

, the aromatic ring represented by the formula;

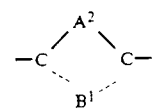

(i)

or the formula:

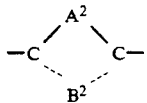

is an aromatic ring optionally containing 1 to 3 hetero atoms selected from the group consisting of nitrogen atom(s), oxygen atom(s) and sulfur atom(s), such as a benzene, pyrrole, furan, thiophene, oxazole, isoxazole, thiazole, isothiazole, imidazole, 1,3,4-oxadiazole, 1,3,4-thiaziazole, pyridine, pyridazine, pyrimidine, pyrazine or triazine ring. Further, in the formula of the above (a), specific examples of the chained group formed by C, D, E, F and G include those represented by the following formulae: $-(CHR^b)_5-$, $-CR^c=CR^c(CHR^b)_3-$, $-CHR^bCR^c=CR^c(CHR^b)_2-$, $-(CHR^b)_2CR^c=CR^cCHR^b-$, $-(CHR^b)_3CR^c=CR^c-$, $-(CR^c=CR^c)_2CHR^b-$, $-CHR^b(CR^c=CR^c)_2-$, $-CR^c=CR^cCHR^bCR^c=CR^c-$, $-O(CHR^b)_4-$, $-S(CHR^b)_4-$, $-NR^d(CHR^b)_4-$, $-CHR^bO(CHR^b)_3-$, $-CHR^bS(CHR^b)_3-$, $-CHR^bNR^d(CHR^b)_3-$, $-(CHR^b)_2O(CHR^b)_2-$, $-(CHR^b)_2S(CHR^b)_2-$, $-(CHR^b)_2NR^d(CHR^b)_2-$, $-(CHR^b)_3OCHR^b-$, $-(CHR^b)_3SCHR^b-$, $-(CHR^b)_3NR^dCHR^b-$, $-(CHR^b)_4O-$, $-(CHR^b)_4S-$, $-(CHR^b)_4NR^d-$, $-O(CHR^b)_2OCHR^b-$, $-O(CHR^b)_2SCHR^b-$, $-O(CHR^b)_2NR^dCHR^b-$, $-S(CHR^b)_2OCHR^b-$, $-S(CHR^b)_2SCHR^b-$, $-S(CHR^b)_2NR^dCHR^b-$, $-NR^d(CHR^b)_3O-$, $-NR^d(CHR^b)_2SCHR^b-$, $-NR^d(CHR^b)_2NR^dCHR^b-$, $-CHR^bO(CHR^b)_2O-$, $-CHR^bO(CHR^b)_2S-$, $-CHR^bO(CHR^b)_2NR^d-$, $-CHR^bS(CHR^b)_2O-$, $-CHR^bS(CHR^b)_2S-$, $-CHR^bS(CHR^b)_2NR^d-$, $-CHR^bNR^d(CHR^b)_2O-$, $-CHR^bNR^d(CHR^b)_2S-$, $-CHR^bNR^d(CHR^b)_2NR^d-$, $-O(CHR^b)_3O-$, $-O(CHR^b)_3S-$, $-O(CHR^b)_3NR^d-$, $-S(CHR^b)_3O-$, $-S(CHR^b)_3S-$, $-S(CHR^b)_3NR^d-$, $-NR^d(CHR^b)_3O-$, $-NR^d(CHR^b)_3S-$, $-NR^d(CHR^b)_3NR^d-$, $-CO(CHR^b)_4-$, $-CHR^bCO(CHR^b)_3-$, $-(CHR^b)_2CO(CHR^b)_2-$, $-(CHR^b)_3COCHR^b-$, $-(CHR^b)_4CO-$, $-COCR^c=CR^c(CHR^b)_2-$, $-CO(CHR^b)_2CR^c=CR^c-$, $-CO(CR^c=CR^c)_2-$, $-CHR^bCOCR^c=CR^cCHR^b-$, $-CR^c=CR^cCO(CHR^b)_2-$, $-(CHR^b)_2COCR^c=CR^c-$, $-CR^c=CR^cCOCR^c=CR^c-$, $-CHR^bCR^c=CR^cCOCHR^b-$, $-(CHR^b)_2CR^c=CR^cCO-$, $-CR^c=CR^c(CHR^b)_2CO-$, $-(CR^c=CR^c)_2CO-$, $-OCO(CHR^b)_3-$, $-SCO(CHR^b)_3-$, $-NR^dCO(CHR^b)_3-$, $-OCHR^bCO(CHR^b)_2-$, $-SCHR^bCO(CHR^b)_2-$, $-NR^dCHR^bCO(CHR^b)_2-$, $-O(CHR^b)COCHR^b-$, $-S(CHR^b)_2COCHR^b-$, $-NR^d(CHR^b)_2COCHR^b-$, $-O(CHR^b)_3CO-$, $-S(CHR^b)_3CO-$, $-NR^d(CHR^b)_3CO-$, $-OCHR^bCR^c=CR^cCHR^b-$, $-SCHR^bCR^c=CR^cCHR^b-$, $-NR^dCHR^bCR^c=CR^cCHR^b-$, $-OCOCR^c=CR^cCHR^b-$, $-SCOCR^c=CR^cCHR^b-$, $-NR^dCOCR^c=CR^cCHR^b-$, $-OCHR^bCR^c=CR^cCO-$, $-SCHR^bCR^c=CR^cCO-$, $-NR^dCHR^bCR^c=CR^cCO-$, $-O(CHR^b)_2CR^c=CR^c-$, $-S(CHR^b)_2CR^c=CR^c-$, $-NR^d(CHR^b)_2CR^c=CR^c-$, $-OCHR^bCOCR^c=CR^c-$, $-SCHR^bCOCR^c=CR^c-$, $-NR^dCHR^bCOCR^c=CR^c-$, $-COO(CHR^b)_3-$, $-COS(CHR^b-)_3-$, $-CONR^d(CHR^b)_3-$, $-CHR^bOCO(CHR^b)_2-$, $-CHR^bSCO(CHR^b)_2-$, $-CHR^bNR^dCO(CHR^b)_2-$, $-CHR^bOCHR^bCOCHR^b-$, $-CHR^bSCHR^bCOCHR^b-$, $-CHR^bNR^dCHR^bCOCHR^b-$, $-CHR^bO(CHR^b)_2CO-$, $-CHR^bS(CHR^b)_2CO-$, $-CHR^bNR^d(CHR^b)_2CO-$, $-CHR^bOCHR^bCR^c=CR^c-$, $-CHR^bSCHR^bCR^c=CR^c-$, $-CHR^bNR^dCHR^bCR^c=CR^c-$, $-COOCHR^bCR^c=CR^c-$, $-COSCHR^bCR^c=CR^c-$, $-CONR^dCHR^bCR^c=CR^c-$, $-CHR^bOCOCR^c=CR^c-$, $-CHR^bSCOCR^c=CR^c-$, $-CHR^bNR^dCOCR^c=CR^c-$, $-COCHR^bO(CHR^b)_2-$, $-COCHR^bS(CHR^b)_2-$, $-COCHR^bNR^d(CHR^b)_2-$, $-CHR^bCOO(CHR^b)_2-$, $-CHR^bCOS(CHR^b)_2-$, $-CHR^bCONR^d(CHR^b)_2-$, $-(CHR^b)_2OCOCHR^b-$, $-(CHR^b)_2SCOCHR^b-$, $-(CHR^b)_2NR^dCOCHR^b-$, $-(CHR^b)_2OCHR^bCO-$, $-(CHR^b)_2SCHR^bCO-$, $-(CHR^b)_2NR^dCHR^bCO-$, $-CO(CHR^b)_2OCHR^b-$, $-CO(CHR^b)_2SCHR^b-$, $-CO(CHR^b)_2NR^dCHR^b-$, $-CHR^bCOCHR^bOCHR^b-$, $-CHR^bCOCHR^bSCHR^b-$, $-CHR^bCOCHR^bNR^dCHR^b-$, $-(CHR^b)_2COOCHR^b-$, $-(CHR^b)_2COSCHR^b-$, $-(CHR^b)_2CONR^dCHR^b-$, $-(CHR^b)_3OCO-$, $-(CHR^b)_3SCO-$, $-(CHR^b)_3NR^dCO-$, $-CR^c=CR^cCHR^bOCHR^b-$, $-CR^c=CR^cCHR^bSCHR^b-$, $-CR^c=CR^cCHR^bNR^dCHR^b-$, $-CR^c=CR^cCOOCHR^b-$, $-CR^c=CR^cCOSCHR^b-$, $-CR^c=CR^cCONR^dCHR^b-$, $-CR^c=CR^cCHR^bOCO-$, $-CR^c=CR^cCHR^bSCO-$, $-CR^c=CR^cCHR^bNR^dCO-$, $-CO(CHR^b)_3O-$, $-CO(CHR^b)_3S-$, $-CO(CHR^b)_3NR^d-$, $-CHR^bCO(CHR^b)_2O-$, $-CHR^bCO(CHR^b)_2S-$, $-(CHR^b)_2NR^d-$, $-(CHR^b)_2COCHR^bO-$, $-(CHR^b)_2COCHR^bS-$, $-(CHR^b)_2COCHR^bNR^d-$, $-(CHR^b)_3COO-$, $-(CHR^b)_3COS-$, $-(CHR^b)_3CONR^d-$, $-CR^c=CR^c(CHR^b)_2O-$, $-CR^c=CR^c(CHR^b)_2S-$, $-CR^c=CR^c(CHR^b)_2NR^d-$, $-CR^c=CR^cCOCHR^bO-$, $-CR^c=CR^cCOCHR^bS-$, $-CR^c=CR^cCOCHR^bNR^d-$, $-CHR^bCR^c=CR^cCHR^bO-$, $-CHR^bCR^c=CR^cCHR^bS-$, $-CHR^bCR^c=CR^cCHR^bNR^d-$, $-COCR^c=CR^cCHR^bO-$, $-COCR^c=CR^cCHR^bS-$, $-COCR^c=CR^cCHR^bNR^d-$, $-CHR^bCR^c=CRCOO-$, $-CHR^bCR=CR^cCOS-$, $-CHR^bCR^c=CR^cCONR^d-$, $-OCOCHR^bOCHR^b-$, $-OCOCHR^bSCHR^b-$, $-OCOCHR^bNR^dCHR^b-$, $-SCOCHR^bOCHR^b-$, $-SCOCHR^bSCHR^b-$, $-SCOCHR^bNR^dCHR^b-$, $-NR^dCOCHR^bOCHR^b-$, $-NR^dCOCHR^bSCHR^b-$, $-NR^dCOCHR^bNR^dCHR^b-$, $-OCHR^bCOOCHR^b-$, $-OCHR^bCOSCHR^b-$, $-OCHR^bCONR^dCHR^b-$, $-SCHR^bCOOCHR^b-$, $-SCHR^bCOSCHR^b-$, $-SCHR^bCONR^dCHR^b-$, $-NR^dCHR^bCOOCHR^b-$, $-NR^dCHR^bCOSCHR^b-$, $-NR^dCHR^bCONR^dCHR^b-$, $-O(CHR^b)_2OCO-$, $-O(CHR^b)_2SCO-$, $-O(CHR^b)_2NR^dCO-$, $-S(CHR^b)_2OCO-$, $-S(CHR^b)_2SCO-$, $-S(CHR^b)_2NR^dCO-$, $-NR^d(CHR^b)_2OCO-$, $-NR^d(CHR^b)_2SCO-$, $-NR^d(CHR^b)_2NR^dCO-$, $-COO(CHR^b)_2O-$, $-COO(CHR^b)_2S-$, $-COO(CHR^b)_2NR^d-$, $-COS(CHR^b)_2O-$, $-COS(CHR^b)_2S-$, $-COS(CHR^b)_2NR^d-$, $-CONR^d(CHR^b)_2O-$, $-CONR^d(CHR^b)_2S-$, $-CONR^d(CHR^b)_2NR^d-$, $-CHR^bOCOCHR^bO-$, $-CHR^bOCOCHR^bS-$, $-CHR^bOCOCHR^bNR^d-$, $-CHR^bSCOCHR^bO-$, $-CHR^bSCOCHR^bS-$, $-CHR^bSCOCHR^bNR^d-$, $-CHR^bNR^dCOCHR^bO-$, $-CHR^bNR^dCOCHR- $^b$S—, —CHR$^b$NR$^d$COCHR$^b$NR$^d$—, —CHR$^b$OCHR$^b$COO—, —CHR$^b$OCHR$^b$COS—, —CHR$^b$OCHR$^b$CONR$^d$—, —CHR$^b$SCHR$^b$COO—, —CHR$^b$SCHR$^b$COS—, —CHR$^b$SCHR$^b$CONR$^d$—, —CHR$^b$NR$^d$CHR$^b$COO—, —CHR$^b$NR$^d$CHR$^b$COS—, —CHR$^b$NR$^d$CHR$^b$CONR$^d$—, —OCO(CHR$^b$)$_2$O—, —OCO(CHR$^b$)$_2$S—, —OCO(CHR$^b$)$_2$NR$^d$—, —OCHR$^b$COCHR$^b$O—, —OCHR$^b$COCHR$^b$S—, —OCHR$^b$COCHR$^b$NR$^d$—, —O(CHR$^b$)$_2$COO—, —O(CHR$^b$)$_2$COS—, —O(CHR$^b$)$_2$CONR$^d$—, —SCO(CHR$^b$)$_2$O—, —SCO(CHR$^b$)$_2$S—, —SCO(CHR$^b$) NR$^d$—, —SCHR$^b$COCHR$^b$O—, —SCHR$^b$COCHR$^b$S—, —SCHR$^b$COCHR$^b$NR$^d$—, —S(CHR$^b$) COO—, —S(CHR$^b$)$_2$COS—, —S(CHR$^b$)$_2$CONR$^d$—, —NR$^d$CO(CHR$^b$)$_2$O—, —NR$^d$CO(CHR$^b$)$_2$S—, —NR$^d$CO(CHR$^b$)$_2$NR$^d$—, —NR$^d$CHR$^b$COCHR$^b$O—, —NR$^d$CHR$^b$COCHR$^b$S—, —NR$^d$CHR$^b$COCHR$^b$NR$^d$—, —NR$^d$(CHR$^b$)$_2$COO—, —NR$^d$(CHR$^b$)$_2$COS—, —NR$^d$(CHR$^b$)$_2$CONR$^d$—, etc. In these formulae, R$^b$, R$^c$ and R$^d$ are as defined above.

On the other hand, in the formula of the above (b), specific examples of the chained group formed by H, I, J, K and L include those represented by the following formulae:
—(CHR$^f$)$_4$CHR$^i$—, —CR$^g$=CR$^g$(CHR$^f$)$_2$CHR$^i$—, —CHR$^f$CR$^g$=CR$^g$CHR$^f$CHR$^i$—, —(CHR$^f$)$_2$CR$^g$=CR$^g$CHR$^i$—, —(CHR$^f$)$_3$CR$^g$=CR$^j$—, —(CR$^g$=CR$^g$)$_2$CHR$^i$—, —CHR$^f$CR$^g$=CR$^g$CR$^g$=CR$^j$—, —CR$^g$=CR$^g$CHR$^f$CR$^g$=CR$^j$—, —O(CHR$^f$)$_3$CHR$^i$—, —S(CHR$^f$)$_3$CHR$^i$—, —NR$^h$(CHR$^f$)$_3$CHR$^i$—, —CHR$^f$O(CHR$^f$)$_2$CHR$^i$—, —CHR$^f$S(CHR$^f$)$_2$CHR$^i$—, —CHR$^f$NR$^h$(CHR$^f$)$_2$CHR$^i$—, —(CHR$^f$)$_2$OCHR$^f$CHR$^i$—, —(CHR$^f$)$_2$SCHR$^f$CHR$^i$—, —(CHR$^f$)$_2$NR$^h$CHR$^f$CHR$^i$—, —(CHR$^f$)$_3$OCHR$^i$—, —(CHR$^f$)$_3$SCHR$^i$—, —(CHR$^f$)$_3$NR$^h$CHR$^i$—, —O(CHR$^f$)$_2$OCHR$^i$—, —O(CHR$^f$)$_2$SCHR$^i$—, —O(CHR$^f$)$_2$NR$^h$CHR$^i$—, —S(CHR$^f$)$_2$OCHR$^i$—, —S(CHR$^f$)$_2$SCHR$^i$—, —S(CHR$^f$)$_2$NR$^h$CHR$^i$—, —NR$^h$(CHR$^f$)$_2$OCHR$^i$—, —NR$^h$(CHR$^f$)$_2$SCHR$^i$—, —NR$^h$(CHR$^f$)$_2$NR$^h$CHR$^i$—, —CR$^g$=CR$^g$COCHR$^f$CHR$^i$—, —(CR$^g$=CR$^g$)$_2$CO—, —COCR$^g$=CR$^g$CHR$^f$ CHR$^i$—, —(CHR$^f$)$_2$CR$^g$=CR$^g$CO—, —(CHR$^f$)$_2$COCR$^g$=CR$^j$—, —CR$^g$=CR$^g$COCR$^g$CR$^j$—, —OCHR$^f$CR$^g$CHR$^i$—, —OCOCR$^g$=CR$^g$CHR$^i$—, —SCOCR$^g$=CR$^g$CHR$^i$—, —NR$^h$COCR$^g$=CR$^g$CHR$^i$—, —CHR$^f$OCHR$^f$CR$^g$=CR$^j$—, —CHR$^f$SCHR$^f$CR$^g$=CR$^j$—, —CHR$^f$NR$^h$CHR$^f$CR$^g$=CR$^j$—, —CR$^g$=CR$^g$CHR$^f$OCHR$^i$—, —CR$^g$=CR$^g$CHR$^f$SCHR$^i$—, —CR$^g$=CR$^g$CHR$^f$NR$^h$CHR$^i$—, —O(CHR$^f$)$_2$CR$^g$=CR$^j$—, —S(CHR$^f$)$_2$CR$^g$=CR$^j$—, —NR$^h$(CHR$^f$)$_2$CR$^g$=CR$^j$—, —COOCHR$^f$CR$^g$=CR$^j$—, —COSCHR$^f$CR$^g$=CR$^j$—, —CONR$^h$CHR$^f$CR$^g$=CR$^j$—, —CR$^g$=CR$^g$COOCHR$^i$—, —CR$^g$=CR$^g$COSCHR$^i$—, —CR$^g$=CR$^g$CONR$^h$CHR$^i$—, —CHR$^f$OCOCR$^g$=CR$^j$—, —CHR$^f$SCOCR$^g$=CR$^j$—, —CHR$^f$NR$^h$COCR$^g$=CR$^j$13, —CR$^g$=CR$^g$CHR$^f$ OCO—, —CR$^g$=CR$^g$CHR$^f$SCO—, —CR$^g$=CR$^g$CHR$^f$NR$^h$CO—, —OCOCHR$^f$OCHR$^i$—, —OCOCHR$^f$SCHR$^i$—, —OCOCHR$^f$NR$^h$CHR$^i$—, —SCOCHR$^f$OCHR$^i$—, —SCOCHR$^f$SCHR$^i$—, —SCOCHR$^f$NR$^h$CHR$^i$—, —NR$^h$COCHR$^f$OCHR$^i$—, —NR$^h$COCHR$^f$SCHR$^i$—, —NR$^h$COCHR$^f$NR$^h$CHR$^i$—, —OCOCHR$^f$OCO—, —OCOCHR$^f$SCO—, —OCOCHR$^f$NR$^h$CO—, —SCOCHR$^f$OCO—, —SCOCHR$^f$SCO—, —S-COCHR$^f$NR$^h$CO—, —NR$^h$COCHR$^f$OCO—, —NR$^h$COCHR$^f$SCO—, —NR$^h$COCHR$^f$NR$^h$CO—, —O(CHR$^f$)$_2$OCO—, —O(CHR$^f$)$_2$SCO—, —O(CHR$^f$)$_2$NR$^h$CO—, —S(CHR$^f$)$_2$OCO—, —S(CHR$^f$)$_2$SCO—, —S(CHR$^f$)$_2$NR$^h$CO—, —NR$^h$(CHR$^f$)$_2$OCO—, —NR$^h$(CHR$^f$)$_2$SCO—, —NR$^h$(CHR$^f$)$_2$NR$^h$CO—, etc. In these formulae, R$^f$, R$^g$, R$^h$, R$^i$ and R$^j$ are as defined above. Further, the aromatic ring represented by the above formula (i) or (ii) can be unsubstituted or monosubstituted by a halogen atom, hydroxyl group, cyano group, lower alkyl group or lower alkoxy group (see the definitions of R$^a$ and R$^b$).

In the formula of the above (a), preferred as the aromatic ring represented by the above formula (i) is a benzene, furan, thiophene, oxazole, isoxazole, thiazole, isothiazole, 1,3,4-oxadiazole, 1,3,4-thiadiazole, pyridine, pyridazine, pyrimidine or pyrazine ring, and preferred as the substituent R$^a$ of the aromatic ring is a hydrogen atom, hydroxyl group, fluorine atom, chlorine atom, methyl group, ethyl group or methoxy group. Further, preferred as the chained group symbolized by the formula —C—D—E—F—G— is a group represented by the formula —(CH$_2$)$_5$—, —CH(CH$_3$) (CH$_2$)$_4$—, —CH=CH (CH$_2$)$_3$—, —C (CH$_3$)=CH(CH$_2$)$_3$—, —CH=C (CH$_3$) (CH$_2$)$_3$—, —CH=CHCH (CH$_3$) (CH$_2$)$_2$—, —(CH$_2$)$_3$CH=CH—, —CH (CH$_3$)(CH$_2$)$_2$CH=CH—, —(CH$_2$)$_3$CH=C (CH$_3$)—, —(CH=CH)$_2$CH$_2$—, —C(CH$_3$)=CHCH=CHCH$_2$—, —CH=CHC(CH$_3$)=CHCH$_2$—, —CH$_2$(CH=CH)$_2$—, —CH$_2$CH=C(CH$_3$)CH=CH—, —CH=CHCH$_2$CH=CH—, —S(CH$_2$)$_4$—, —CH$_2$O(CH$_2$)$_3$—, —CH(CH$_3$)O(CH$_2$)$_3$—, —CH$_2$OCH(CH$_3$)(CH$_2$)$_2$—, —CH$_2$S(CH$_2$)$_3$—, —CH$_2$NH(CH$_2$)$_3$—, —CH$_2$N(CH$_3$)(CH$_2$)$_3$—, —(CH$_2$)$_2$O(CH$_2$)$_2$—, —CH(CH$_3$)CH$_2$O(CH$_2$)$_2$—, —(CH$_2$)$_2$S(CH$_2$)$_2$—, —(CH$_2$)$_2$NH(CH$_2$ )$_2$—, —(CH$_2$)$_2$N(CH$_3$)(CH$_2$)$_2$—, —(CH$_2$)$_2$N(C$_2$H$_5$) (CH$_2$)$_2$—, —(CH$_2$)$_3$OCH$_2$—, —CH(CH$_3$)(CH$_2$)$_2$OCH$_2$—, —(CH$_2$)$_3$SCH$_2$—, —(CH$_2$)$_3$NHCH$_2$—, —(CH$_2$)$_3$N(CH$_3$)CH$_2$—, —(CH$_2$)$_4$O—, —CH(CH$_3$)(CH$_2$)$_3$O—, —(CH$_2$)$_4$S—, —(CH$_2$)$_4$NH—, —(CH$_2$)$_4$N(CH$_3$)—, —S(CH$_2$)$_2$OCH$_2$—, —NH(CH$_2$)$_2$OCH$_2$—, —N(CH$_3$)(CH$_2$)$_2$OCH$_2$—, —CH$_2$O(CH$_2$)$_2$O—, —CH(CH$_3$)O(CH$_2$)$_2$O—, —CH$_2$OCH(CH$_3$)CH$_2$O—, —CH$_2$O(CH$_2$)$_2$S—, —CH$_2$O(CH$_2$)$_2$NH—, —CH$_2$O(CH$_2$)$_2$N (CH$_3$)—, —CH$_2$S (CH$_2$)$_2$O—, —CH$_2$NH(CH$_2$)$_2$O—, —CH$_2$N(CH$_3$)(CH$_2$)$_2$O—, —S(CH$_2$)$_3$O—, —NH(CH$_2$)$_3$O—, —N(CH$_3$)(CH$_2$)$_3$O—, —CO(CH$_2$)$_4$—, —CH$_2$CO (CH$_2$)$_3$—, —(CH$_2$)$_2$CO(CH$_2$)$_2$—, —(CH$_2$)$_3$COCH$_2$—, —(CH$_2$)$_4$CO—, —COCH=CH(CH$_2$)$_2$—, —COCH=C (CH$_3$)(CH$_2$)$_2$—, —CO(CH=CH)$_2$—, —COCH=C (CH$_3$)CH=CH—, —CH=CHCO(CH$_2$)$_2$—, —C(CH$_3$)=CHCO(CH$_2$)$_2$—, —(CH$_2$)$_2$COCH=CH—, —CH=CHCOCH=CH—, —C(CH$_3$) =CHCOCH=CH—, —(CH$_2$)$_2$CH=CHCO—, —(CH=CH)$_2$CO—, —C(CH$_3$)=CHCH=CHCO—, —NHCO(CH$_2$)$_3$—, —N(CH$_3$)CO(CH$_2$)$_3$—, —SCH$_2$CO(CH$_2$)$_2$—, —S(CH$_2$)$_2$COCH$_2$—, —S(CH$_2$)$_3$CO—, —SCH$_2$CH=CHCO—, —S(CH$_2$)$_2$CH=CH—, —NH(CH$_2$)$_2$CH=CH—, —N(CH$_3$)(CH$_2$)$_2$CH=CH—, —SCH$_2$COCH=CH—, —COO(CH$_2$)$_3$—, —CONH(CH$_2$)$_3$—, —CON(CH$_3$)(CH$_2$)$_3$—, —CH$_2$OCO(CH$_2$)$_2$—, —CH$_2$NHCO(CH$_2$)$_2$—, —CH$_2$N(CH$_3$)CO(CH$_2$)$_2$—, —CH$_2$OCH$_2$COCH$_2$—, —CH$_2$SCH$_2$COCH$_2$—, —CH$_2$NHCH$_2$COCH$_2$—, —CH$_2$O(CH$_2$)$_2$CO—, —CH$_2$S(CH$_2$)$_2$CO—, —CH₂NH(CH₂)₂CO—, —CH₂OCH₂CH=CH—, —CH(CH₃)COCH₂CH=CH—, —CH₂OCH(CH₃)CH=CH—, —CH₂OCH₂CH=C(CH₃)—, —CH(CH₃)OCH(CH₃)CH=CH—, —CH₂SCH₂CH=CH—, —CH(CH₃)SCH₂CH=CH—, —CH₂NHCH₂CH=CH—, —CH(CH₃)NHCH₂CH=CH—, —CH₂N(CH₃)CH₂CH=CH—, —CH(CH₃)N(CH₃)CH₂CH=CH—, —COOCH₂CH=CH—, —CONHCH₂CH=CH—, —CON(CH₃)CH₂CH=CH—, —CH₂OCOCH=CH—, —CH₂NHCOCH=CH—, —CH₂N(CH₃)COCH=CH—, —COCH₂O(CH₂)₂—, —COCH₂NH(CH₂)₂—, —COCH₂N(CH₃)(CH₂)₂—, —CH₂COO(CH₂)₂—, —CH₂CONH(CH₂)₂—, —CH₂CON(CH₃)(CH₂)₂—, —(CH₂)₂OCOCH₂—, —(CH₂)₂NHCOCH₂—, —(CH₂)₂N(CH₃)COCH₂—, —(CH₂) , —(CH₂)₂NHCH₂CO—, —(CH₂)₂N(CH₃)CH₂CO—, —CO(CH₂)₂OCH₂—, —CO(CH₂)₂SCH₂—, —CO(CH₂)₂NHCH₂—, —CO(CH₂)₂N(CH₃)CH₂—, —CH₂COCH₂OCH₂—, —CH₂COCH₂SCH₂—, —CH₂COCH₂NHCH₂—, —CH₂COCH₂N(CH₃)CH₂—, —(CH₂)₂COOCH₂—, —(CH₂)₂CONHCH₂—, —(CH₂)₂CON(CH₃)CH₂—, —(CH₂)₃OCO—, —(CH₂)₃NHCO—, —(CH₂)₃N(CH₃)CO—, —CH=CHCH₂OCH—, —C(CH₃)=CHCH₂OCH₂—, —CH=C(CH₃)CH₂OCH₂—, —CH=CHCH(CH₃)OCH₂—, —CH=CHCH₂OCH(CH₃)—, —C(C₂H₅)=CHCH₂OCH₂—, —C(CH₃)=CHCH(CH₃)OCH—, —CH=CHCH₂SCH₂—, —C(CH₃)=CHCH₂SCH₂—, —CH=CHCH₂NHCH₂—, —C(CH₃)=CHCH₂NHCH₂—, —CH=CHCH₂N(CH₃)CH₂—, —C(CH₃)=CHCH₂N(CH₃)CH₂—, —CH=CHCOOCH₂—, —CH=CHCONHCH₂—, —CH=CHCON(CH₃)CH₂—, —CH=CHCH₂OCO—, —CH=CHCH₂NHCO—, —CH=CHCH₂N(CH₃)CO—, —CO(CH₂)₃O—, —CO(CH₂)₃S—, —CO(CH₂)₃NH—, —CO(CH₂)₃N(CH₃)—, —CH₂CO(CH₂)₂O—, —CH₂CO(CH₂)₂S—, —CH₂CO(CH₂)₂NH—, —CH₂CO(CH₂)₂N(CH₃)—, —(CH₂)₂COCH₂O—, —(CH₂)₂COCH₂NH—, —(CH₂)₂COCH₂N(CH₃)—, —(CH₂)₃COO—, —(CH₂)₃CONH—, —(CH₂)₃CON(CH₃)—, —CH=CH(CH₂)₂O—, —C(CH₃)=CH(CH₂)₂O—, —CH=CHCH(CH₃)CH₂O—, —CH=CH(CH₂)₂S—, —C(CH₃)=CH(CH₂)₂S—, —CH=CH(CH₂)₂NH—, —C(CH₃)=CH(CH₂)₂NH—, —CH=CH(CH₂)₂N(CH₃)—, —C(CH₃)=CH(CH₂)₂N(CH₃)—, —CH=CHCOCH₂O—, —C(CH₃)=CHCOCH₂O—, —CH=CHCOCH₂NH—, —CH=CHCOCH₂N(CH₃)—, —COCH=CHCH₂O—, —COCH=CHCH₂NH—, —COCH=CHCH₂N(CH₃)—, —OCOCH₂OCH₂—, —NHCOCH₂OCH₂—, —N(CH₃)COCH₂OCH₂—, —COO(CH₂)₂O—, —CONH(CH₂)₂O—, —CON(CH₃)(CH₂)₂O—, —CH₂OCOCH₂O—, —CH₂NHCOCH₂O—, —CH₂N(CH₃)COCH₂O—, —CH₂OCH₂COO—, —CH₂OCH₂CONH—, —CH₂OCH₂CON(CH₃)—, —SCH₂COCH₂O—, —NHCO(CH₂)₂O— or —N(CH₃)CO(CH₂)₂O—.

Particularly preferred examples of the group of the above (a) include those represented by the following formulae:

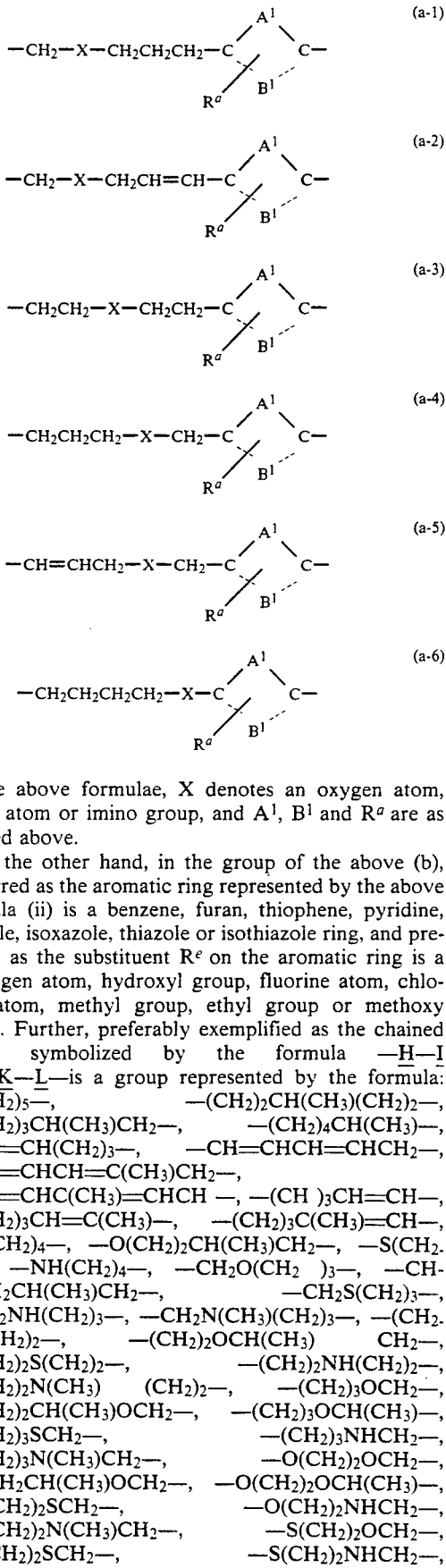

In the above formulae, X denotes an oxygen atom, sulfur atom or imino group, and $A^1$, $B^1$ and $R^a$ are as defined above.

On the other hand, in the group of the above (b), preferred as the aromatic ring represented by the above formula (ii) is a benzene, furan, thiophene, pyridine, oxazole, isoxazole, thiazole or isothiazole ring, and preferred as the substituent $R^e$ on the aromatic ring is a hydrogen atom, hydroxyl group, fluorine atom, chlorine atom, methyl group, ethyl group or methoxy group. Further, preferably exemplified as the chained group symbolized by the formula —H—I—J—K—L— is a group represented by the formula: —(CH₂)₅—, —(CH₂)₂CH(CH₃)(CH₂)₂—, —(CH₂)₃CH(CH₃)CH₂—, —(CH₂)₄CH(CH₃)—, —CH=CH(CH₂)₃—, —CH=CHCH=CHCH₂—, —CH=CHCH=C(CH₃)CH₂—, —CH=CHC(CH₃)=CHCH—, —(CH )₃CH=CH—, —(CH₂)₃CH=C(CH₃)—, —(CH₂)₃C(CH₃)=CH—, —O(CH₂)₄—, —O(CH₂)₂CH(CH₃)CH₂—, —S(CH₂)₄—, —NH(CH₂)₄—, —CH₂O(CH₂)₃—, —CH₂OCH₂CH(CH₃)CH₂—, —CH₂S(CH₂)₃—, —CH₂NH(CH₂)₃—, —CH₂N(CH₃)(CH₂)₃—, —(CH₂)₂O(CH₂)₂—, —(CH₂)₂OCH(CH₃) CH₂—, —(CH₂)₂S(CH₂)₂—, —(CH₂)₂NH(CH₂)₂—, —(CH₂)₂N(CH₃) (CH₂)₂—, —(CH₂)₃OCH₂—, —(CH₂)₂CH(CH₃)OCH₂—, —(CH₂)₃OCH(CH₃)—, —(CH₂)₃SCH₂—, —(CH₂)₃NHCH₂—, —(CH₂)₃N(CH₃)CH₂—, —O(CH₂)₂OCH₂—, —OCH₂CH(CH₃)OCH₂—, —O(CH₂)₂OCH(CH₃)—, —O(CH₂)₂SCH₂—, —O(CH₂)₂NHCH₂—, —O(CH₂)₂N(CH₃)CH₂—, —S(CH₂)₂OCH₂—, —S(CH₂)₂SCH₂—, —S(CH₂)₂NHCH₂—, —S(CH₂)₂N(CH₃)CH₂—, —NH(CH₂)₂OCH₂—, —NH(CH₂)₂SCH₂—, —NH(CH₂)₂NHCH₂—, —NH(CH₂)₂N(CH₃)CH₂—, —CH=CHCO(CH₂)₂—, —CH=CHCOCH(CH₃)CH₂—, —CH=CHCH=CH-CO—, —CH=CHCH=C(CH₃)CO—, —CH=CHC(CH₃)=CHCO—, —COCH=CH(CH₂)₂—, —COCH=CHCH(CH₃)CH₂—, —(CH₂)₂CH=CHCO—, —(CH₂)₂CH=C(CH₃)CO—, —(CH₂)₂COCH=CH—, —(CH₂)₂COCH=C(CH₃)—, —COCH=CHCH=CH—, —COCH=CHC(CH₃)=CH—, —CH=CHCOCH=CH—, —OCH₂CH=CHCH₂—, —OCOCH=CHCH₂—, —SCH₂CH=CHCH₂—, —NHCH₂CH=CHCH₂—, —NHCOCH=CHCH₂—, —CH₂OCH₂CH=CH—, —CH₂OCH₂C(CH₃)=CH—, —CH₂SCH₂CH=CH—, —CH₂SCH₂C(CH₃)=CH—, —CH₂NHCH₂CH=CH—, —CH₂N(CH₃)CH₂CH=CH—, —CH=CHCH₂OCH₂—, —CH=CHCH(CH₃)OCH₂—, —CH=CHCH₂OCH(CH₃)—, —CH=CHCH₂SCH₂—, —CH=CHCH(CH₃)SCH₂—, —CH=CHCH₂NHCH₂—, —CH=CHCH(CH₃)NHCH₂—, —CH=CHCH₂N(CH₃)CH₂—, —CH=CHCH₂N(C₂H₅)CH₂—, —CH=CHCH₂NHCO—, —CH=CHCH₂N(CH₃)CO—, —O(CH₂)₂CH=CH—, —S(CH₂)₂CH=CH—, —NH(CH₂)₂CH=CH—, —COOCH₂CH=CH—, —CONHCH₂CH=CH—, —CH=CHCOOCH₂—, —CH=CHCOOCH(CH₃)—, —CH=CHCOSCH₂—, —CH=CHCONHCH₂—, —CH=CHCONHCH(CH₃)—, —CH=CHCON(CH₃)CH₂—, —CH=CHCON(C₂H₅)CH₂—, —CH₂OCOCH=CH—, —CH₂OCOC(CH₃)=CH—, —CH₂NHCOCH=CH—, —CH₂NHCOC(CH₃)=CH—, —CH₂N(CH₃)COCH=CH—, —CH=CHCH₂OCO—, —CH=CHCH(CH₃)OCO—, —CH=CHCH₂SCO—, —CH=CHCH₂SCO—, —CH=CHCH₂NHCO—, —CH=CHCH₂N(CH₃)CO—, —CH=CHCH₂N(C₂H₅)CO—, —OCOCH₂OCH₂—, —OCOCH₂SCH₂—, —OCOCH₂NHCH₂—, —OCOCH₂N(CH₃)CH₂—, —NHCOCH₂OCH₂—, —NHCOCH(CH₃)OCH₂—, —NHCOCH₂SCH₂—, —NHCOCH₂NHCH₂—, —NHCOCH₂N(CH₃)CH₂—, —OCOCH₂OCO—, —OCOCH₂NHCO—, —OCOCH₂N(CH₃)CO—, —NHCOCH₂OCO—, —NHCOCH₂NHCO—, —NHCOCH₂N(CH₃)CO—, —O(CH₂)₂OCO—, —O(CH₂)₂NHCO—, —OCH₂CH(CH₃)NHCO—, —O(CH₂)₂N(CH₃)CO—, —S(CH₂)₂OCO—, —S(CH₂)₂NHCO—, —NH(CH₂)₂NHCO— or —NH(CH₂)₂N(CH₃)CO—.

Particularly preferred as the groups of the above (b) are those represented by the following formulae

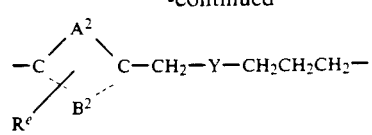

(b-1)

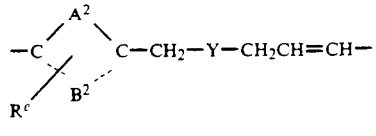

(b-2)

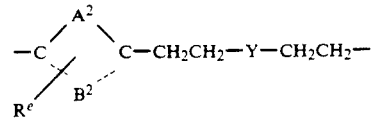

(b-3)

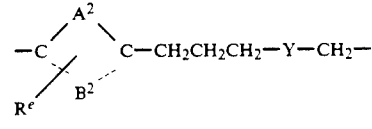

(b-4)

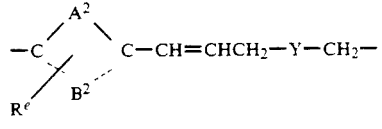

(b-5)

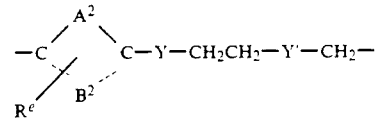

(b-6)

(b-7)

(b-8)

In the above formulae, Y and Y' are the same or different and each denotes an oxygen atom, sulfur atom or imino group, and $A^2$, $B^2$ and $R^e$ are as defined above $R^1$ denotes a hydrogen atom, lower alkyl group, lower haloalkyl group, lower alkenyl group, lower alkynyl group or cycloalkyl group, and among them, preferred as the lower alkyl group is a methyl, ethyl or propyl group, preferred as the lower haloalkyl group is a 2-fluoroethyl group, preferred as the lower alkenyl group is an alkyl group, preferred as the lower alkynyl group is a propargyl group, and preferred as the cycloalkyl group is a cyclopropyl group.

$R^2$, $R^3$, $R^4$ and $R^5$ are the same or different and each denotes a hydrogen atom, halogen atom or lower alkyl group, or $R^2$ and $R^4$ and/or $R^3$ and $R^5$ combine to denote a single bond. Preferred as the lower alkyl group is a methyl or ethyl group, and preferred as the halogen atom is a fluorine atom or chlorine atom. Further, the case where $R^2$ and $R^4$, and/or $R^3$ and $R^5$ denote a single bond means that the part represented by

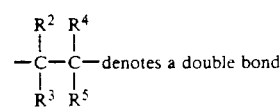 denotes a double bond

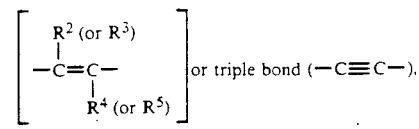 or triple bond (—C≡C—).

and the double bond formed therein may be either of cis (Z) and trans (E), but trans (E) form is preferred in general. Particularly preferably, $R^2$, $R^3$, $R^4$ and $R^5$ are hydrogen atoms at the same time, or $R^2$ and $R^4$, and/or $R^3$ and $R^5$ combine to form a single bond and the remainder of $R^2$, $R^3$, $R^4$ and $R^5$ are the same or different and each is a hydrogen or fluorine atom.

$R^6$ and $R^7$ are the same or different and each denotes a hydrogen atom, halogen atom or lower alkyl group, or $R^6$ and $R^7$ combine to denote a single bond. In the above, preferred as the lower alkyl group is a methyl or ethyl group, and preferred as the halogen atom is a fluorine or chlorine atom. Further, specifically the case where $R^6$ and $R^7$ denote a single bond means that the part represented by

denotes a triple bond ($-C\equiv C-$). Particularly preferably, $R^6$ and $R^7$ are hydrogen atoms, or $R^6$ and $R^7$ combine to form a single bond.

$R^8$ and $R^9$ are the same or a different and each is a fluorine atom, trifluoromethyl group or lower alkyl group, or $R^8$ and $R^9$ combine to denote a group forming a cycloalkane together with the adjacent carbon atom. Among them, mentioned as particularly preferred groups are the case where each of $R^8$ and $R^9$ denotes a fluorine atom, methyl group, ethyl group, propyl group or trifluoromethyl group, or $R^8$ and $R^9$ form a cyclopropane ring together with the adjacent carbon atom (namely, the part denoted by

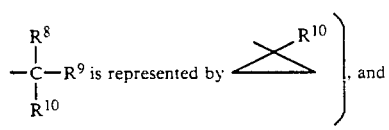

particularly preferred is the case where both $R^8$ and $R^9$ are methyl groups $R^{10}$ denotes a hydrogen atom, fluorine atom, trifluoromethyl group, acetoxy group, lower alkyl group or lower alkoxy group. In the above, preferred as the lower alkyl group is a straight-chain lower alkyl group having 1 to 4 carbon atoms such as, for example, a methyl, ethyl, propyl or butyl group, and preferred as the lower alkoxy group is a straight-chain alkoxy group having 1 to 3 carbon atoms such as a methoxy, ethoxy or propoxy group. Particularly, preferred is a hydrogen atom, fluorine atom, trifluoromethyl group, acetoxy group, methyl group, ethyl group, propyl group, methoxy group, ethoxy group or propoxy group, and most preferred is a fluorine atom, methyl group, ethyl group, methoxy group or ethoxy group.

The substituted amine derivative of the above formula [I] can exist in the form of an acid addition salt, and mentioned as such an acid addition salt is an inorganic acid salt such as, for example, hydrochloride, hydrobromide, hydroiodide, sulfate, nitrate, perchlorate or phosphate; or an organic acid salt such as, for example, p-toluenesulfonate, benzenesulfonate, methanesulfonate, oxalate, succinate, tartrate, citrate, fumarate or maleate, and a pharmaceutically acceptable non-toxic salt is particularly preferred.

Further, there is a case where stereoisomers such as diastereomers, geometrical isomers or optical isomers exist about the compounds of the formula [I] of the invention, according to the form of their substituents, and the compounds of the formula [I] of the invention include all these stereoisomers and their mixtures.

Compounds of the formula [I] of the invention can be prepared, for example, according to the methods indicated in the following reaction equations 1 to 3.

Reaction equation 1

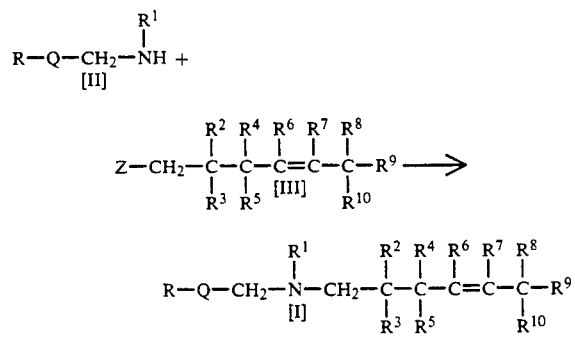

Reaction equation 2

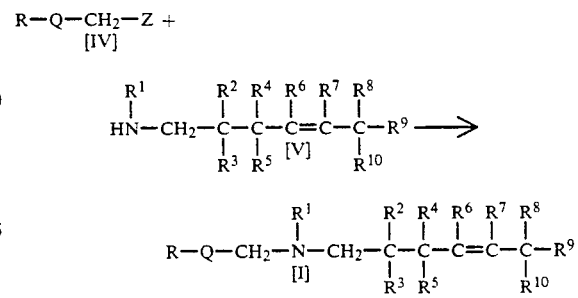

Reaction equation 3

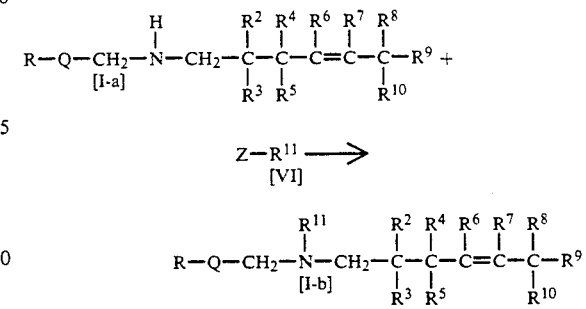

wherein Z denotes an eliminatable group, $R^{11}$ denotes a lower alkyl, lower alkenyl, lower alkynyl, cycloalkyl or lower haloalkyl group, and Q, R, $R^1$, $R^2$, $R^3$, $R^4$, $R^5$, $R^6$, $R^7$, $R^8$, $R^9$ and $R^{10}$ are as defined above.

Specifically mentioned as an eliminable group symboled by Z is a halogen atom such as a chlorine, bromine or iodine atom, or an organic sulfonyloxy group such as a methanesulfonyloxy or p-toluenesulfonyloxy group.

Any of the reactions represented by the above reaction equations is an alkylation reaction for primary or secondary amines well known in the field of organic synthesis chemistry, and a most universal method usable for synthesis of almost all the compounds of the invention. According to the invention, an objective compound of the above formula [I] or [I-b] can usually be prepared by reacting an amine represented by the general formula [II], [V] or [I-a] with a corresponding alkylating agent represented by the general formula [III], [IV] or [VI] in an equimolar or a small excess amount of the latter preferably in the range of 1 to 2 moles of the latter per mole of the amine in a solvent having no bad influence on the reaction, for example in an aromatic hydrocarbon such as benzene, toluene or xylene; an ether such as ethyl ether, tetrahydrofuran or dioxane; a halogenated hydrocarbon such as methylene chloride, chloroform or dichloroethane; an alcohol such as ethanol or isopropanol; an aprotic polar solvent such as acetonitrile or dimethylsulfoxide; or a mixture thereof.

As for conditions of the reactions indicated in the above reaction equations 1, 2 and 3, reaction temperature is generally in the range of about $-70°$ C. to the boiling point of the solvent, preferably about $-20°$ C. to about 150° C., and reaction time can be usually 5 minutes to 10 days, preferably 1 to 24 hours. Further, in order to let these reactions proceed smoothly, it is advantageous in general to carry out the reactions in the presence of a base, and the base usable there includes, for example, an alkali metal hydride such as sodium hydride, lithium hydride or potassium hydride; an alkali or alkaline earth metal hydroxide such as sodium hydroxide, potassium hydroxide or calcium hydroxide; an alkali metal carbonate salt such as sodium carbonate, potassium carbonate or sodium bicarbonate; or an organic amine such as triethylamine or pyridine. The use amount of these bases is generally an equimolar or excess amount, preferably in the range of 1 to 5 times moles based on the starting compound of the formula [II], [V] or [I-a].

Compounds of the invention can also be prepared by utilizing the reactions disclosed in the following reaction equations 4 to 7.

Reaction equation 4

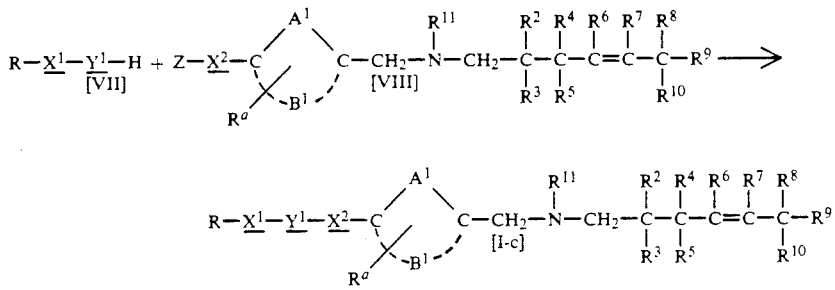

Reaction equation 5

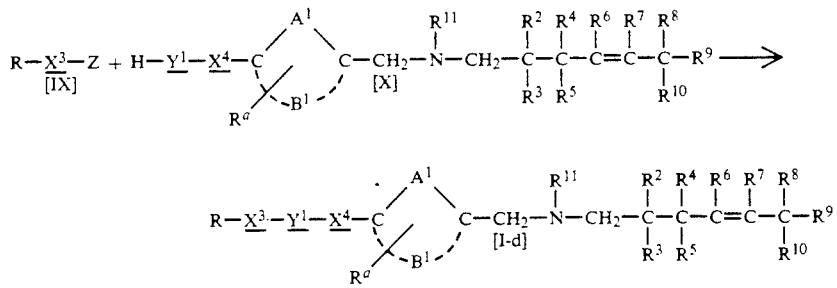

Reaction equation 6

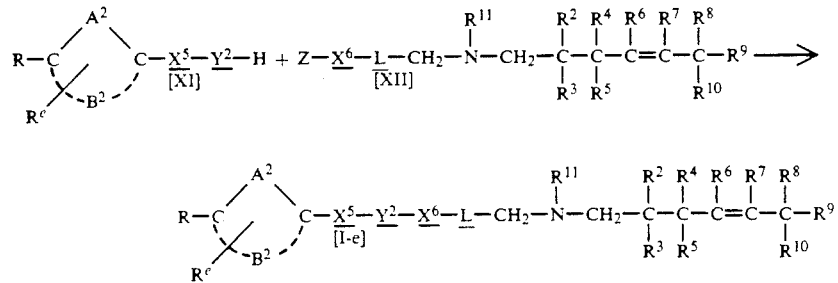

Reaction equation 7

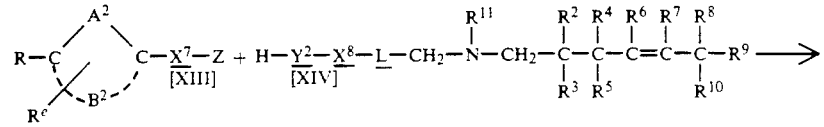

-continued

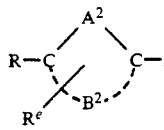 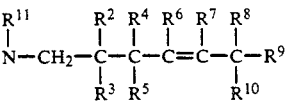

wherein $Y^1$ denotes an oxygen atom, sulfur atom or group represented by the formula $-NR^d-$ and $Y^2$ denotes an oxygen atom, sulfur atom or group represented by the formula $-NR^h-$, wherein $R^d$ and $R^h$ are as defined above;

$X^1$ and $X^2$, and $X^3$ and $X^4$ denote, together respectively, the remaining groups when any one of C, D, E, F and G is the above $Y^1$, wherein C, D, E, F and G are as defined above;

$X^5$ and $X^6$, and $X^7$ and $X^8$ denote, together respectively, the remaining groups when any one of H, I, J, and K is the above $Y^2$, wherein H, I, J and K are as defined above; and $A^1$, $A^2$, $B^1$, $B^2$, L, R, $R^2$, $R^3$, $R^4$, $R^5$, $R^6$, $R^7$, $R^8$, $R^9$, $R^{10}$, $R^{11}$, $R^a$, $R^e$ and Z are as defined above.

The methods indicated in the above reaction equations 4 to 7 are general preparation methods of compounds of the invention containing hetero atom(s) such as oxygen atom(s), sulfur atom(s) or nitrogen atom(s) in the chain formed by C, D, E, F and G or by H, I, J and K in the above formula [I], namely compounds of the above formulae [I-d], [I-e] and [I-f]. These compounds can be classified into ethers, sulfides, amines, esters, thioesters and amides depending on the kind of the hetero atom(s) contained and the kind of the groups adjacent thereto, and they can be prepared according to general preparation methods well known in the field of organic synthetic chemistry in accordance with respective compounds.

Namely, in case of an ether, sulfide or amine which contains oxygen atom(s), sulfur atom(s) or nitrogen atom(s) as hetero atom(s) in the chain in the general formula [I-c], [I-d], [I-e] or [I-f] and wherein both groups adjacent to the hetero atom(s) are formed by a group represented by the formula $-CHR^b-$ or by the formula $-CHR^f-$, wherein $R^b$ and $R^f$ are as defined above, provided that $X^1$ and $X^4$, and $X^5$ and $X^8$ may be a single bond, respectively, it can be prepared by reacting a hydroxy derivative, mercapto derivative or amino derivative represented by the general formula [VII], [X], [XI] or [XIV] with a corresponding compound represented by the general formula [VIII], [IX], [XII] or [XIII], in a solvent having no bad influence on the reaction, either in an equimolar ratio or in small excess of either of the reactive components, preferably using 1 to 2 moles of a compound of the formula [VII], [IX], [XI] or [XIII] per mole of a compound of the formula [VIII], [X], [XII] or [XIV]. The reaction solution usable there includes an aromatic hydrocarbon such as benzene, toluene or xylene; an ether such as ethyl ether, tetrahydrofuran or dioxane; a halogenated hydrocarbon such as methylene chloride, chloroform or dischloroethane; a ketone such as acetone; an ester such as ethyl acetate; an aprotic polar solvent such as acetonitrile, dimethylformamide or dimethylsulfoxide; or a mixture thereof As for conditions of the reaction, reaction temperature is generally in the range of about $-70°$ C. to the boiling point of the solvent, preferably in the range of about $-20°$ C. to about $150°$ C., and reaction time can be usually 10 minutes to 48 hours, preferably 1 to 24 hours Further, in this reaction, it is advantageous to carry out the reaction in the presence of a base for smooth proceeding thereof, and the base usable there can be an alkali metal hydride such as sodium hydride, lithium hydride or potassium hydride; an alkali metal or alkaline earth metal hydride such as sodium hydroxide, potassium hydroxide or calcium hydroxide; an alkali metal carbonate salt such as sodium carbonate, potassium carbonate or sodium bicarbonate; or an organic amine such as triethylamine or pyridine The use amount of these bases is generally equimolar or in an excess amount, preferably 1 to 5 moles per mole of each starting compound Further, when the compound of the formula [I-c], [I-d], [I-e] or [I-f] is the above ether, the compound can be prepared by reacting a hydroxy derivative represented by the general formula [VII], [X], [XI] or [XIV] with a compound represented by the general formula [VIII], [IX], [XII] or [XIII] wherein the eliminable group (Z) denotes a halogen atom such as a chlorine, bromine or iodine atom in a solvent having no bad influence in the presence of a silver salt such as silver trifluoroacetate or silver carbonate. The use amounts of each starting compound and the silver salt can be usually preferably equimolar, but either one can be in an excess amount. The reaction temperature can be generally in the range of about $-20°$ C. to the boiling point of the solvent, preferably in the range of about $0°$ C. to about $100°$ C., and the reaction time can be usually 10 minutes to 48 hours, preferably 1 to 24 hours.

On the other hand, the synthesis of an ester, thioester or amide which contains oxygen atom(s), sulfur atom(s) or nitrogen atom(s) as hetero atom(s) in the chain in the general formula [I-c], [I-d], [I-e] or [I-f] and wherein one group adjacent to the hetero atom is a carbonyl group and the other group is a group represented by the formula $-CHR^b-$ or by the formula $-CHR^f-$ wherein $R^b$ and $R^f$ are as defined above, provided that $X^1$ and $X^4$, and $X^5$ and $X^8$ may be a single bond, respectively, can easily be carried out, too, by a general synthetic method of an ester thioester or amide well known in the field of organic chemistry. For example, such a compound can usually be prepared by reacting a hydroxy derivative, mercapto derivative or amino derivative with a corresponding reactive derivative of a carboxylic acid such as an acid chloride or acid anhydride represented by the general formula [VIII], [IX], [XII] or [XIII], in an equimolar amount or in a small excess of one reactive component, preferably using 1 to 2 moles of the compound of the formula [VII], [IX], [XI] or [XIII] per mole of the compound of the formula [VIII], [X], [XII] or [XIV], in a solvent not involved in the reaction, for example in an organic solvent such as tetrahydrofuran, dichloromethane, chloroform, benzene, ethyl acetate, acetone, acetonitrile, dimethylformamide or dimethylsulfoxide or a mixed solvent thereof with water.

As for reaction conditions therefor, reaction temperature is generally in the range of about $-70°$ C. to the boiling point of the solvent, preferably in the range of about $-20°$ C. to about $100°$ C., and reaction time can be usually 5 minutes to 10 days, preferably 10 minutes to 24 hours. Further, for smooth progress of the reaction it is advantageous to carry out the reaction in the presence of a base, and the base usable there includes, for example, an alkali metal or alkaline earth metal hydroxide such as sodium hydroxide, potassium hydroxide or calcium hydroxide; an alkali metal carbonate salt such as sodium carbonate, potassium carbonate or sodium bicarbonate; or an organic amine such as triethylamine or pyridine. The use amount of these bases is generally equimolar or excess, preferably 1 to 5 moles per mole of each starting compound.

Further, some of the compounds of the invention can also be prepared according to the methods indicated in the following reaction equations 8 to 11.

of the previously defined $\underline{C}$, $\underline{D}$, $\underline{E}$, $\underline{F}$ and $\underline{G}$ combine to form a group represented by the formula —CH$_2$NH— or a group represented by the formula —NHCH$_2$—;

$\underline{X}^{13}$ and $\underline{X}^{14}$, and $\underline{X}^{15}$ and $\underline{X}^{16}$ denote, together respectively, the remaining groups when any neighboring two of the previously defined $\underline{H}$, $\underline{I}$, $\underline{J}$ and $\underline{K}$ combine to form a group represented by the formula —CH$_2$NH— or by a group represented by the formula —NHCH$_2$—; and $A^1$, $A^2$, $B^1$, $B^2$, $\underline{L}$, R, $R^2$, $R^3$, $R^4$, $R^5$, $R^6$, $R^7$, $R^8$, $R^9$, $R^{10}$, $R^{11}$, $R^a$ and $R^e$ are as defined above.

The methods indicated in the above reaction equations 8 to 11 are preparation methods for compounds of the invention having a group represented by —CH$_2$NH— or a group represented by —NHCH— in the chain Reaction equation 8

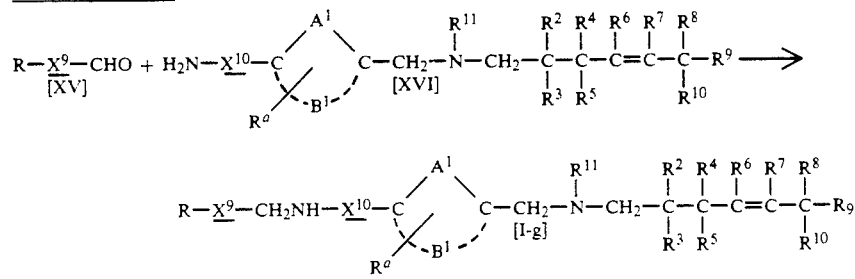

Reaction equation 9

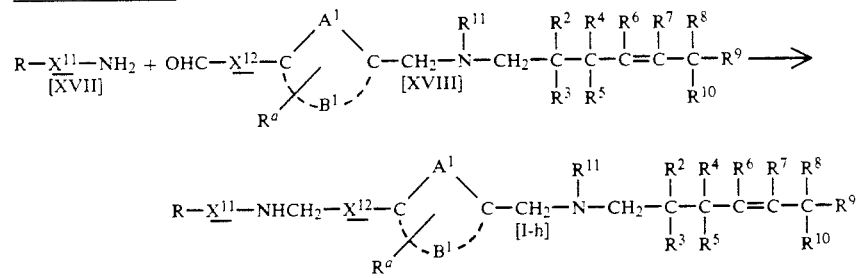

Reaction equation 10

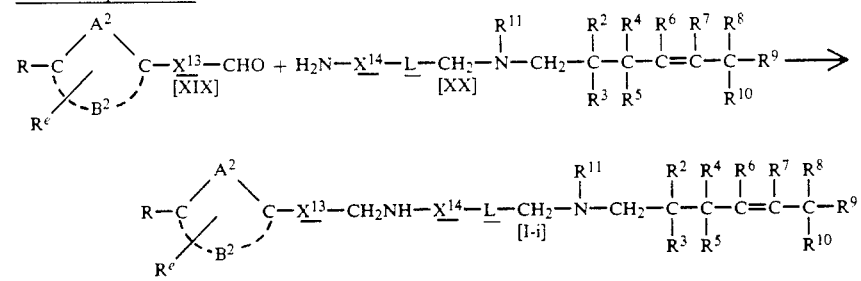

Reaction equation 11

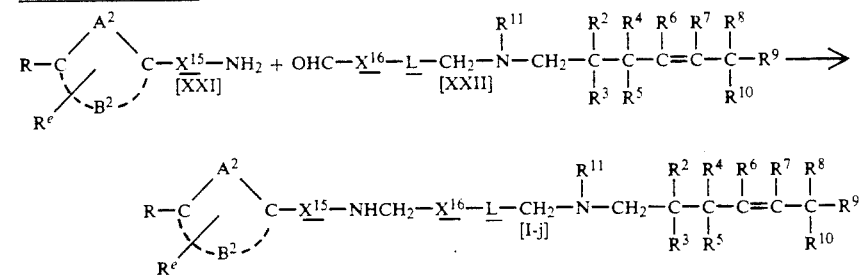

wherein $\underline{X}^9$ and $\underline{X}^{10}$, and $\underline{X}^{11}$ and $\underline{X}^{12}$ denote, together respectively, the remaining groups when any neighboring two formed by $\underline{C}$, $\underline{D}$, $\underline{E}$, $\underline{F}$ and $\underline{G}$ or by $\underline{H}$, $\underline{I}$, $\underline{J}$, $\underline{K}$ and $\underline{L}$, namely compounds of the above formulae [I-g], [I-h], [I-i] and [I-j]. The reactions indicated by the above reaction equations 8 to 11 can, for example, be carried out by previously condensing a compound of the formula [XV], [XVIII], [XIX] or [XXII] with an almost equimolar amount of a compound of the formula [XVI], [XVII], [XX] or [XXI] in benzene, tetrahydrofuran or an alcohol to form an imine and reducing it. Mentioned as the reducing agent usable for this reduction is, for example, a complex metal hydride such as sodium borohydride, sodium cyanoborohydride or lithium aluminum hydride. Further, as reduction conditions therefor, there is, for example, a method which comprises carrying out the reaction in a solvent such as methanol, ethanol or tetrahydrofuran at about 0° C. to room temperature for 1 to 6 hours using a reducing agent in an equimolar or excess mole amount based on the imine, preferably using 1 to 5 moles thereof per mole of the imine.

Some compounds of the invention can further be prepared even by the methods indicated by the following reaction equations 12 to 15.

Reaction equation 12

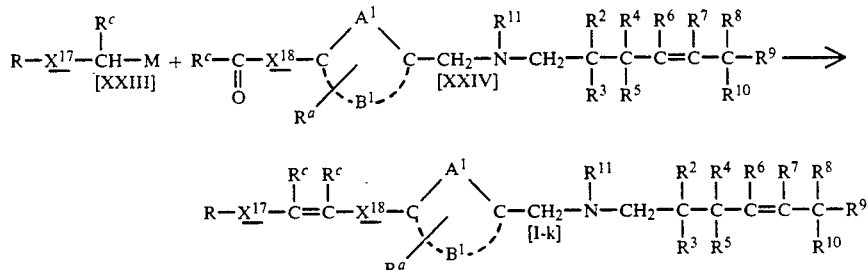

Reaction equation 13

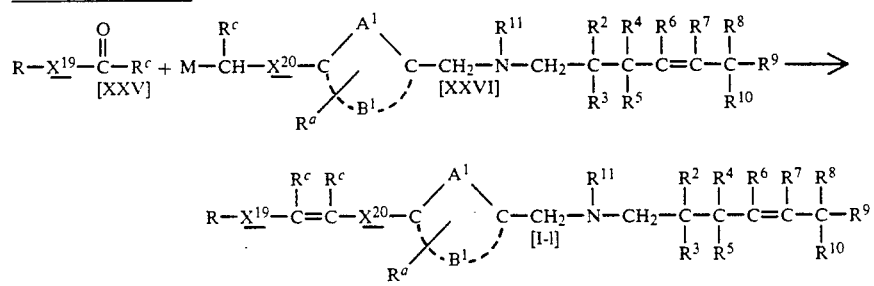

Reaction equation 14

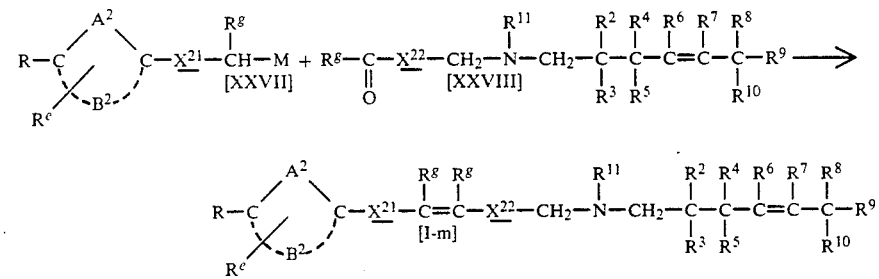

Reaction equation 15

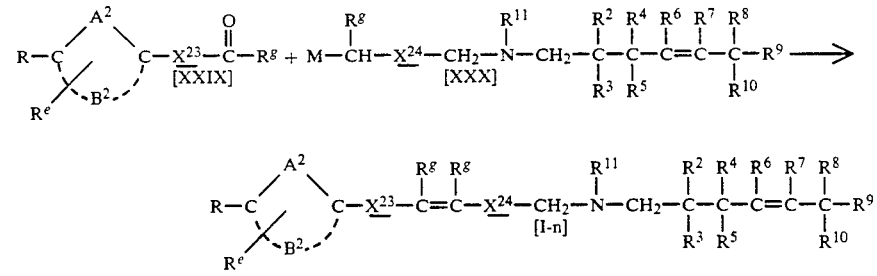

wherein

M denotes a group represented by the formula:

wherein G denotes a halogen atom, or by the formula:

wherein $R^i$ denotes a lower alkyl group;

$X^{17}$ and $X^{18}$, and $X^{19}$ and denote, together respectively, the remaining groups when any neighboring two of the previously defined C, D, E, F and G combine to form a double bond optionally substituted by a lower alkyl group;

$X^{21}$ and $X^{22}$, and $X^{23}$ and denote, together respectively, the remaining groups when any neighboring two of the previously defined H, I, J, K and L combine to form a double bond optionally substituted by a lower alkyl group; and $A^1$, $A^2$, $B^1$, $B^2$, L, R, $R^2$, $R^3$, $R^4$, $R^5$, $R^6$, $R^7$, $R^8$, $R^9$, $R^{10}$, $R^{11}$, $R^a$, $R^c$, $R^e$, $R^g$ and $R^i$ are as defined above.

The reactions indicated in the above reaction equations 12 to 15 are general preparation methods for compounds of the invention having double bond(s) in the chain formed by C, D, E, F and G or by H, I, J, K and L, namely for the compound of the above formula [I-k], [I-1], [I-m] and [I-n]. Namely, such a compound can be prepared by reacting a phosphonium salt or phosphonate represented by the general formula [XXIII], [XXVI], [XXVII] or [XXX] with an aldehyde or ketone represented by the general formula [XXIV], [XXV], [XXVIII] or [XXIX] in an equimolar ratio or in a rate of small excess of the latter in a solvent having no relation to the reaction. As the solvent to be used there, in case of, for example, a phosphonium salt derivative tetrahydrofuran, dimethylformamide or the like is preferred, and in case of a phosphonate derivative tetrahydrofuran, benzene, toluene or the like is preferred. Further, this reaction is preferably carried out usually in the presence of a base, and especially when a phosphonium salt derivative is used as a starting compound, it is necessary to let a base act in advance or in the reaction system. Such a base can, for example, include sodium hydroxide, sodium hydride, butyllithium or the like. Although the reaction conditions largely vary depending on the reaction seeds to be used, reaction temperature and reaction time are, for example, about $-70°$ C. to about $200°$ C. and about 10 minutes to about 24 hours, respectively.

Because of diversity in the structure of compounds of the invention, it is also possible to synthesize them via various routes according to other various preparation methods well known in organic synthetic chemistry, in addition to the various preparation methods exemplified above. These preparation methods include, for example, construction of a heterocyclic group in the final step, e.g. a method indicated by the following reaction equation:

Reaction equation 16

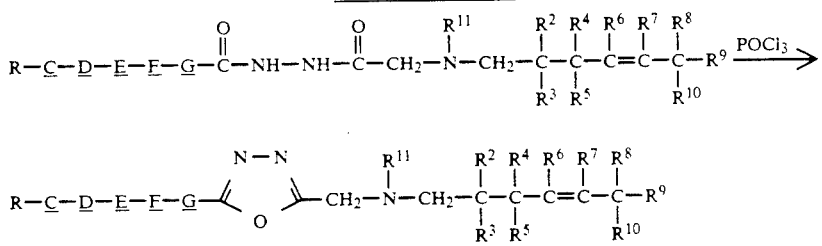

, and construction of an en-yne or diyne structure similarly in the final step, e.g. methods indicated by the following reaction equations 17 to 19:

Reaction equation 17

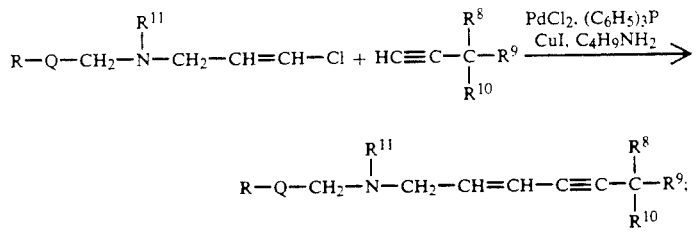

Reaction equation 18

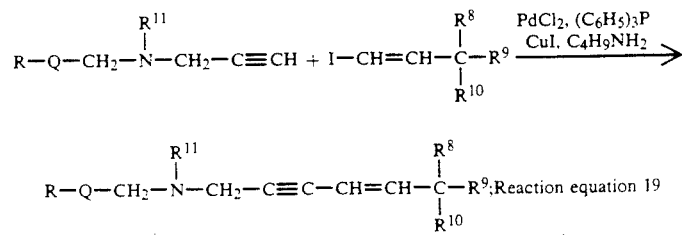

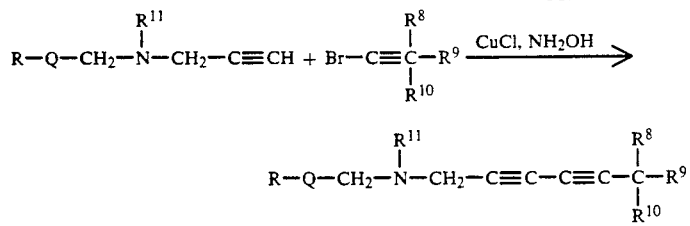

In each of the above-described reaction methods, when in addition to the hydroxyl group, mercapto group or amino group having relation to the reaction, a reactive functional group such as a hydroxyl group or amino group coexists in the compounds to be used as starting compounds, it is possible, if necessary, to carry out the reaction after appropriate protection of these reactive functional groups and remove these protective groups after the reaction. Protective groups to be used there include those readily eliminated by hydrolysis under an acidic or alkaline condition, for example, methoxymethyl, tetrahydropyranyl, trityl, dimethyl(tert butyl)silyl, formyl, acetyl, methoxycarbonyl, ethoxycarbonyl and tertbutoxycarbonyl groups.

Compounds of the formula [I] of the invention to be obtained by the above steps can be isolated and purified, for example, by column chromatography, solvent extraction, recrystallization or the like, alone or in appropriate combinations. Further, if necessary, compounds of the invention of the formula [I] as a free base can be converted to their acid addition salts, or reversely, their acid addition salts can be converted to their free bases The step to convert compounds of the formula [I] as a free base to their acid addition salts, or the step to convert acid addition salts to their free bases can easily be carried out by a conventional method using a corresponding acid or base, respectively Starting compounds of the formulae [II] to [XXX] used in the above reaction equations 1 to 15 can either be purchased as a commercial product, or prepared by the methods disclosed in Japanese Laid-Open Patent Publication No. 5059/1988, the methods previously reported by the present inventors [see Japanese Patent Application No. 296840/1988, EP-A-318860, WO 90/5132 (PCT/JP89/00522)] or methods based thereon, or further methods disclosed in the later reference examples or other methods.

Compounds of the invention of the formula [I] inhibit mammal squalene epoxidase extremely selectively and strongly, and are thus useful compounds whose use is expected as an antihypercholesterolemia agent, an antihyperlipemia agent or an antiarteriosclerosis agent.

In order to verify this, a test example is mentioned and described below. Test example Squalene epoxidase inhibition action (1) Preparation of squalene epoxidase Human squalene epoxidase is prepared based on the method disclosed in J. Biol. Chem. 245, 1670 (1970) and ibid. 250, 1572 (1975).

Namely, human hepatoma (Hep-G2) cells are cultured at 37° C. under 5% carbon dioxide-mixed air. After completion of the culture the cells are scraped and recovered by centrifugation. The cells are suspended (1 × 10$^8$ cells/ml) in a 0.1M Tris-HCl buffer (pH 7.5), the suspension is homogenized and centrifuged at 9,750×g for 10 minutes, and the sediment is washed with a 0.1M Tris-HCl buffer (pH 7.5) and centrifuged at 105,000×g for 1 hour. The resulting microsome is suspended in a 0.1M Tris-HCl buffer (pH 7.5) so that the protein amount becomes 20 mg/ml, and the suspension is stirred under ice cooling in the presence of 1 % Triton X-100 for solubilization. After this solubilization treatment, the solution is diluted with 1 mM EDTA and 1 mM dithiothreitol so that the Triton X-100 concentration becomes 0.125 %, and then centrifuged at 105,000×g for 1 hour. The resulting supernatant is used in the later test as a squalene epoxidase fraction.

(2) Method for measurement of squalene epoxidase activity

Measurement of human squalene epoxidase activity is carried out based on the method disclosed in J. Biol. Chem. 245, 1670 (1970).

Namely, 3 Ml of a dimethylsulfoxide solution of a test drug is added to a solution consisting of 0.2 ml of the squalene epoxidase fraction prepared in (1) [Protein amount 0.4 mg, 0.1 % Triton X-100, 20 $\mu$M Tris-HCl buffer (pH 7.5)], 100 $\mu$M FAD, 1 mM NADPH, 1 mM EDTA total volume 0.3 ml, and the mixture is subjected to shaking reaction at 37° C. for 60 minutes. 0.3 ml of a 10 % potassium hydroxide-methanol solution is added to stop the reaction, and the mixture is heated at 75° C. for 1 hour. Then, after extraction of the nonsaponified substances, the extract is concentrated to dryness in a stream of nitrogen. The resulting residue is dissolved in a small amount of ethyl ether, dropped on Pre-coated silicagel TLC and developed with benzene-ethyl acetate (99.5:0.5). The position of the formed $^3$H-squalene-2,3-epoxide on TLC is ascertained using as a marker ergosterol acetate and the $^3$H-squalene-2,3-epoxide part of TLC is cut out. The TLC piece is immersed in a toluene series scintillator and measurement is carried out using a liquid scintillation counter. By this, 50% inhibitory concentrations (IC50 values) of compounds of the invention on squalene epoxidase are determined, and the results are shown in the following table.

TABLE 1

| Test drug | Human squalene epoxidase inhibition action 50% inhibitory concentration (IC50, nM) |
| --- | --- |
| Compound of Example 7 | 0.3 |
| Compound of Example 30 | 0.8 |
| Compound of Example 35 | 0.4 |
| Compound of Example 38 | 0.2 |
| Compound of Example 46 | 0.4 |
| Compound of Example 48 | 0.5 |

As apparent from the above results, compounds of the invention are effective for treatment or prophylaxis of various diseases caused by sthenia of the cholesterol biosynthesis mechanism and/or excessive ingestion of cholesterol, etc., for example, diseases such as obesity, hypercholesterolemia, hyperlipemia and arteriosclerosis. Further, the squalene epoxidase inhibition action of compounds of the invention is not observed on fungi, etc. and is specific for mammals and their toxicity is low, and thus the, invention is extremely useful in the field of medicine Compounds of the formula [I] of the invention can be administered orally or parenterally, and can be provided, through formulation into forms suitable for such administrations, for treatment and prophylaxis of hypercholesterolemia, hyperlipemia, arteriosclerosis, etc. In case where compounds of the invention are clinically used, it is also possible to administer them after they are variously formulated in accordance with their administration forms and in addition of pharmaceutically acceptable additives. Additives usable therefor include various additives usually used in the pharmaceutical filed, for example, gelatin, lactose, sucrose, titanium oxide, starch, crystalline cellulose, hydroxypropylcellulose, carboxymethylcellulose, corn starch, microcrystalline wax, white Vaseline, magnesium metasilicate aluminate, anhydrous calcium phosphate, citric acid, trisodium citrate, hydroxypropylcellulose, sorbitol, sorbitan aliphatic acid esters, polysorbate, sucrose aliphatic acid esters, polyoxyethylenecured castor oil, polyvinylpyrrolidone, magnesium stearate, light anhydrous silicic acid, talc, vegetable oils, benzyl alcohol, gum arabic, propylene glycol, polyalkylene glycol, cyclodextrin, hydroxypropylcyclodextrin, etc. Dosage forms into which compounds of the invention formulated as a mixture with these additives include solid formulations such as, for example, tablets, capsuls, granules, powders and suppository; and liquid formulations such as, for example, syrups, elixirs and injections, and these can be prepared according to usual methods in the filed of formulations. The liquid formulations may be in the form wherein they are dissolved or suspended in a suitable medium at the time of use. Further, particularly in case of injections, they can be dissolved or suspended, if necessary, in physiological saline or a glucose solution, and a buffering agent and a preservative can also be added.

These formulations can contain a compound of the invention in the rate of 0 to 100 weight %, preferably 1.0 to 60 weight %. These formulation can also contain another therapeutically effective compound When a compound of the invention is used as an antihyperlipemia agent, an antiarteriosclerosis agent or an antihypercholesterolemia agent, its dose and the number of administration vary depending on the sex, age, body weight and the severity of symptom of patients and the type and range of the intended therapeutic effect and the like. Generally, in oral administration, it is administered preferably in a daily dose of 0.01 to 20 mg per kg of an adult once or in several divided portions In parenteral administration, it is preferably administered in a daily dose of 0.001 to 2 mg per kg of an adult once or in several divided portions

EXAMPLE 1

Production of (E,E)-N-ethyl-N-(6,6-dimethyl-2-hepten-4-ynyl)-3-[3-(3-thienyl)-2-propenyloxymethyl]benzylamine hydrochloride 6.9 g of (E)-3-[3-(3-thienyl)-2-propenyloxymethyl]benzyl bromide was dissolved in 50 ml of dimethylformamide, and 5.3 g of (E)-N-ethyl-6,6-di-methyl-2-hepten-4-ynylamine hydrochloride and 7.0 g of potassium carbonate were added. The solution was stirred overnight at room temperature. The solvent was evaporated, and ethyl acetate and water were added to the residue to extract it. The organic layer was separated, washed with a saturated aqueous solution of sodium chloride, and dried over anhydrous magnesium s sulfate. The desiccant was separated by filtration, and the solvent was evaporated under reduced pressure The residue was dissolved in 10 ml of ethanol, and to this solution, a hydrogen chloride-methanol solution was added, then the solvent was evaporated again The residue was recrystallized from a mixture of ethyl ether and hexane to give 6.7 g (yield 72 %) of the captioned compound as a white powder, m.p.103°-105° C.

IR(KBr,cm$^{-1}$)
3448,2968,2926,2608,1458,1398,1110,966,771 $^{1}$H-NMR(300 MHz,CDCl$_3$,δppm):1.24(9H,s),1.44(2H,t,J=7.1 Hz),1.54-1.57(2H,m),2.94-3.05(2H,m),3.52-3.57(1H,m), 3.65-3.67(1H,m),4.-08-4.13(2H,m),4.20(2H,dd,J=6.5Hz, 1.4Hz),4.59(2H,s),5.82(1H,d,J=15.9Hz),6.17(1H,dt,J=15.9Hz,6.5Hz),6.26(1H,dt,J=15.6Hz,7.3Hz),6.65(1H,d-,J=15.6Hz),7.17-7.23(2H,m),7.-26-7.28(1H,m),7.44(2H,d,J=4.7Hz),7.61-7.64(2H,m).

Compounds of Examples 2 to 7 were obtained by s performing the same reaction as in Example 1 except that the corresponding bromomethyl or chloromethyl derivatives and/or 2-hepten-4-ynylamine derivatives were used instead of the starting compounds, (E)-3-[3—(3-thienyl)-2-propenyloxymethyl]benzyl bromide and/or (E)- N-ethyl-6,6-dimethyl-2-hepten-4-ynylamine hydrochloride, which were used in the above-mentioned reaction. ( When the reaction product was a free base, the hydrochloride producing step in the aftertreatment was not included.)

EXAMPLE 2

(E,E)-N-ethyl-N-(6,6-dimethyl-2-hepten-4-ynyl)-3-[3-(3-thienylmethoxy)-1-propenyl]benzylamine IR(neat,cm$^{-1}$):
2968,2866,1458,1365,1266,1107,1083,966, 774,693.
$^{1}$H-NMR(300MHz,CDCl$_3$,δppm):1.04(3H,t,J=7.0Hz),1.2-4(9H, s),2.50(2H,q,J=7.0Hz),3.09(2H,dd,J=6.3Hz,1.4Hz),3.-54 (2H,s),4.18(2H,dd,J=6.4Hz,1.6Hz),4.58(2H,s),5.64(1H, dt,J=15.9Hz,1.4Hz),6.08(1H,dt,J=15.9Hz,6.3Hz),6.31-(1H, dt,J=15.8Hz,6.4Hz),6.62(1H,dt,J=15.8Hz,1.6Hz),7.10--7.12 (1H,m),7.20-7.27(4H,m),7.-30-7.33(1H,m),7.35(1H, br.s).

EXAMPLE 3

(E)-N-ethyl-N-(6,6-dimethyl-2-hepten-4-ynyl)-3-[3-(3-thienyl)propoxymethyl]benzylamine IR(neat,cm$^{-1}$)
2968,2926,1455,1365,1266,1152,1107,960, 774.
$^{1}$H-NMR(300 MHz,CDCl$_3$,δ ppm):1.04(3H,t,J=7.1 Hz),1.24(9H, s),1.92-1.97(2H,m),2.50(2H,q,J=7.1 Hz),2.75(2H,t,J=7.7 Hz),3.09(2H,dd,J=6.3 Hz,1.5 Hz),3.50(2H,t,J=6.5 Hz), 3.56(2H,s),4.49(2H,s),5.64(1H,dt,J=15.9 Hz,1.5 Hz),6.07 (1H,dt,J=15.9 Hz,6.3 Hz),6.90-6.95(2H,m),7.-20-7.30(5H,m).

EXAMPLE 4

(E,E)-N-ethyl-(6,6-dimethyl-2-hepten-4-ynyl)-3-[3-(5-thiazolyl)-2-propenyloxymethyl]benzylamine IR(neat,cm$^{-1}$): 2974,1458,1365,1266,1113,960,870.

$^1$H-NMR(300 MHz,CDCl$_3$,δ ppm):1.04(3H,t,J=7.1 Hz),1.23(9H, s),2.50(2H,q,J=7.1 Hz),3.09(2H,dd,J=6.6 Hz,1.5 Hz),3.56 (2H,s),4.16(2H,dd,J=5.5 Hz,1.5 Hz),4.56(2H,s),5.64(1H, dt,J=15.9Hz,1.5 Hz),6.07(1H,dt,J=15.9 Hz,6.6 Hz),6.18(1H, dt,J=15.9 Hz,6.0 Hz),6.80(1H,d,J=15.9 Hz),7.22–7.31(4H, m),7.74(1H,s),8.63(1H,s).

EXAMPLE 5

(E)-N-ethyl-N-(6,6-dimethyl-2-hepten-4-ynyl)-3-2-[2-(3-thienyl)ethoxy]ethyl]benzylamine IR(neat,cm$^{-1}$): 2968,2866,1707,1365,1113,774.

$^1$MHz,CDCl$_3$,δ ppm):1.04(3H,t,J=7.1 Hz),1.23(9H, s),2.50(2H,q,J=7.1 Hz),2.88(2H,t,J=6.8 Hz),2.90(2H,t,J=6.1 Hz),3.08(2H,dd,J=6.3 Hz,1.5 Hz),3.53(2H,s),3.62–3.71 (4H,m),5.64(1H,dt,J=15.9 Hz,1.5 Hz),6.07(1H,dt,J=15.9 Hz, 6.3 Hz),6.92–6.98(2H,m),7.07(1H,dt,J=7.2Hz,1.5Hz),7.14–7.29(4H,m).

EXAMPLE 6

(E,E)-N-(6,6-dimethyl-2-hepten-4-ynyl)-N-propyl-3-3-(3-thienyl)-2-propenyloxymethyl]benzylamine hydrochloride m.p.: 70°–72° C.

IR(KBr,cm$^-$): 3442,2974,2932,1458,1110,969.

$^1$H-NMR(300 MHz,CDCl$_3$,δ ppm):0.94(3H,t,J=7.4 Hz),1.25(9H, s),1.90–1.94(2H,m),2.80–2.87(2H,m),3.55–3.68(2H,m), 4.11–4.15(2H,m),4.20(2H,dd,J=6.8 Hz,1.3 Hz),4.59(2H,s), 5.82(1H,d,J=16.0 Hz),6.17,6.25(1H,dt,J=16.0 Hz,6.8 Hz), 6.66(1H,d,J=16.0 Hz),7.18(1H,dd,J=3.1 Hz,1.3 Hz),7.22(1H, dd,J=5.1 Hz,1.2 Hz),7.27(1H,dd,J=5.1 Hz,3.1 Hz),7.44–7.46 (2H,m),7.60–7.63(2H,m).

EXAMPLE 7

(E,E)-N-ethyl-N-(6-methoxy-6-methyl-2-hepten-4-ynyl)-3-[3-(3-thienyl)-2-propenyloxymethyl]benzylamine hydrochloride m.p.:100°–102° C.

IR(KBr,cm$^{-1}$): 2614,2584,1170,1122,1077,966.

$^1$H-NMR(300 MHz,CDCl$_3$,δ ppm):1.46(3H,t,J=7.2 Hz),1.48(6H, s),2.90–3.16(2H,m),3.36(3H,s),3.48–3.78(2H,m),4.05–4.20(2H,m),4.20(2H,dd,J=6.5 Hz,1.5 Hz),4.59(2H,s),5.87 (1H,d,J=15.9 Hz),6.17(1H,dt,J=15.9 Hz,6.3 Hz),6.40(1H,dt, J=15.9 Hz,6.5 Hz),6.65(1H,d,J=15.9 Hz),7.17–7.30(3H,m), 7.43–7.50(2H,m),7.59–7.68(2H,m).

EXAMPLE 8

(E,E)-N-ethyl-N-(6-methoxy-6-methyl-2-hepten-4-ynyl)-5-[3-(3-thienyl)-2-propenyloxymethyl]-1,2,4-oxadiazol-2-ylmethylamine IR(KBr,cm$^{-1}$): 2980,2938,1362,1248,1173,1149,1113,1074, 966,771.

$^1$H-NMR(300 MHz,CDCl$_3$,δ ppm):1.09(3H,t,J=7.0 Hz),1.46(6H, s),2.59(2H,q,J=7.0 Hz),3.25(2H,dd,J=6.5 Hz,1.4 Hz),3.35 (3H,s),3.81(2H,s),4.29(2H,dd,J=6.6 Hz,1.2 Hz),4.76(2H, s),5.72(1H,dt,J=15.9 Hz,1.4 Hz),6.13(1H,dt,J=15.9 Hz, 6.5 Hz),6.16(1H,dt,J=15.9 Hz,6.6 Hz),6.66(1H,d,J=15.9 Hz), 7.18–7.23(2H,m),7.26–7.30(1H,m).

EXAMPLE 9

(E,E)-N-ethyl-N-(6-methoxy-6-methyl-2-hepten-4-ynyl)-6-[3-(3-thienyl)-2-propenyloxymethyl]-2-pyridylmethylamine IR(KBr,cm$^{-1}$):
2980,1461,1248,1173,1149,1116,1077,966,768.

$^1$H-NMR(300 MHz,CDCl$_3$,δ ppm):1.05(3H,t,J=7.1 Hz),1.46(6H, s),2.56(2H,q,J=7.1 Hz),3.17(2H,dd,J=6.3 Hz,1.7 Hz),3.35 (3H,s),3.72(2H,s),4.25(2H,dd,J=6.3 Hz,1.7 Hz),4.66(2H, s),5.70(1H,dt,J=16.1 Hz,1.7 Hz),6.17(1H,dt,J=16.1 Hz, 6.3 Hz),6.19(1H,dt,J=16.1 Hz,6.3 Hz),6.66(1H,dt,J=16.1 Hz, 1.7 Hz),7.16(1H,dd,J=2.5 Hz,1.2 Hz),7.21(1H,dd,J=5.2 Hz, 1.2 Hz),7.27(1H,dd,J=5.2 Hz,2.5 Hz),7.33(1H,d,J=7.7 Hz), 7.39(1H,d,J=7.7 Hz),7.67(1H,t,J=7.7 Hz).

EXAMPLE 10

Production of (E)-N-ethyl-N-(6-methoxy-6-methyl-2-hepten-4-ynyl)-2-2-[3-(3-thienyl)phenoxy]ethoxy]ethylamine hydrochloride 12.0 g of 3-[3-[2-(2-chloroethoxy)ethoxy]phenyl]thiophene, 11.1 g of (E)-N-ethyl-6-methoxy-6-methyl-2-hepten-4-ynylamine hydrochloride, 17.6 g of potassium carbonate and 7.0 g of potassium iodide were dissolved in 300 ml of dimethylformamide, and the mixture was stirred at 95° to 105 ° C. for 5 hours. The solvent was evaporated under reduced pressure, and ethyl acetate and water were added to the residue to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by silica gel column chromatography [hexane/ethyl acetate=5/1→2/1→½] to give 15.7 g (yield 88.6 %) of the captioned free base as a pale yellow oil. The free base (15.7 g) obtained as above was dissolved in methanol, treated with a hydrogen chloride-methanol slution and recrystallized from ethyl ether to give 15.4 g (yield 87.2%) of the captioned compound as a white crystalline powder, m.p.103°–105° C.

IR(KBr,cm$^{-1}$):
3450,2932,2620,1599,1464,1449,1221,1128, 1074,777.

$^1$H-NMR(300 MHz,CDCl$_3$,δ ppm): 1.41(3H,t,J=6.7 Hz),1.44(6H, s),3.12–3.28(4H,m),3.31(3H,s),3.76–3.86(2H,m),3.88–3.91(2H,m),4.00–4.14(2H,m),4.14–4.20(2H,m),5.90(1H,d, J=15.9 Hz),6.25–6.40(1H,m),6.86(1H,ddd,J=8.1 Hz,2.7 Hz, 2.1 Hz),7.12(1H,t,J=2.2 Hz),7.21(1H,ddd,J=8.4 Hz,2.7 Hz, 2.1 Hz),7.31(1H,t,J=7.8 Hz),7.35–7.40(2H,m),7.45(1H,dd, J=2.7 Hz,1.2 Hz).

Compounds of Examples 11 to 20 were obtained by performing the same reaction as in Example 10 except that the corresponding chloroalkyl or bromoalkyl derivatives and/or alkynylamine derivatives were used instead of the starting compounds, 3-[3-[2-(2-chloroethoxy)ethoxy]phenyl]thiophene and/or (E)-N-ethyl-6-methoxy-6-methyl-2-hepten-4-ynylamine, which were used in the above-mentioned reaction.

EXAMPLE 11

(E)-N-(6,6-dimethyl-2-hepten-4-ynyl)-3-2-[3-(3-thienyl)phenyl]ethoxy propylamine IR(neat,cm$^{-1}$): 2968,1458,1364,1266,1114,960,774.

$^1$H-NMR(300 MHz,CDCl$_3$,δ ppm):1.00(3H,t,J=7.2 Hz),1.23(9H, s),1.73(1H,q,J=6.6 Hz),2.45-2.59(4H,m),2.92(2H,t,J=7.2 Hz),3.12(2H,d,J=6.6 Hz),3.48(2H,t,J=6.6 Hz),3.65(2H, t,J=7.2 Hz),5.52(1H,dt,J=15.9 Hz,1.5 Hz),6.03(1H,dt,J=15.9 Hz,6.6 Hz),7.15(1H,dt,J=7.2 Hz,1.8 Hz),7.32(1H,dt,J=7.5 Hz,1.5 Hz),7.37-7.39(2H,m),7.42-7.48(3H,m).

EXAMPLE 12

(E)-N-ethyl-N-(6,6-dimethyl-2-hepten-4-ynyl)-5-[3-(3-thienyl)phenoxy]pentylamine hydrochloride m.p.:119°-121° C.

IR(KBr,cm$^{-1}$): 3432,2972,2944,2872,2616,2488,1602,1480, 1456,1286,1270,1222,1186,776.

$^1$H-NMR(300 MHz,CDCl$_3$,δ ppm):1.24(9H,s),1.41(3H,t,J=7.2 Hz),1.50-2.00(6H,m),2.90-3.00(2H,m),3.08(2H,q,J=7.2 Hz),3.65(2H,d,J=7.2 Hz),4.02(2H,t,J=6.0 Hz),5.85(1H,d,J=15.9 Hz),6.17(1H,dt,J=15.9 Hz,7.2 Hz),6.82(1H,ddd,J=8.1 Hz,2.1 Hz,1.5 Hz),7.11(1H,br.t,J=2.1 Hz),7.18(1H,dt,J=8.1 Hz,1.5 Hz),7.30(1H,t,J=8.1 Hz),7.37(2H,d,J=2.4 Hz), 7.45(1H,t,J=2.4 Hz).

EXAMPLE 13

(E)-N-ethyl-N-(6-methoxy-6-methyl-2-hepten-4-ynyl)-5-[3-(3-thienyl)phenoxy]pentylamine IR(neat,cm$^{-1}$): 3442,2986,2938,2614,2500,1605,1584,1473, 1455,1365,1287,1248,1221,1173,1152,1071, 966,777.

$^1$H-NMR(300 MHz,CDCl$_3$,δ ppm):1.42(3H,t,J=7.2 Hz),1.47(6H, s),1.50-2.00(6H,m),2.-92-3.20(2H,m),3.10(2H,q,J=7.2 Hz), 3.34(3H,s),3.67(2H,d,J=7.2 Hz),4.03(2H,t,J=6.0 Hz),5.91 (1H,d,J=15.9 Hz),6.32(1H,dt,J=15.9 Hz,7.2 Hz),6.82(1H, ddd,J=8.1 Hz,2.7 Hz,1.2 Hz),7.11(1H,br.t,J=2.4 Hz),7.19 (1H,d,J=8.1 Hz),7.30(1H,t,J=8.1 Hz),7.37(2H,d,J=2.4 Hz), 7.45(1H,t,J=2.4 Hz).

EXAMPLE 14

(E,E)-N-ethyl-N-(6,6-dimethyl-2-hepten-4-ynyl)-6-3-(3thienyl)phenyl]-5-hexenylamine IR(neat,cm$^{-1}$): 2974,2932,1600,1461,1365,1269,1203,1086, 963,849,771.

$^1$H-NMR(300 MHz,CDCl$_3$,δ ppm):1.01(3H,t,J=7.2 Hz),1.24(9H, s),1.48-1.50(4H,m),2.24(2H,q,J=6.3 Hz),2.44(2H,t,J=7.2 Hz),2.51(2H,q,J=7.2 Hz),3.11(2H,dd,J=6.3 Hz,1.5 Hz), 5.63(1H,dt,J=15.9 Hz,1.5 Hz),6.05(1H,dt,J=15.9 Hz,6.3 Hz), 6.27(1H,dt,J=15.9 Hz,6.3 Hz),6.42(1H,d,J=15.9 Hz),7.22-7.50(6H,m),7.55(1H,br.s).

EXAMPLE 15

(E)-N-ethyl-N-(6,6-dimethyl-2-hepten-4-ynyl)-2-[2-[3-(5-thiazolyl)phenoxy]ethoxy]ethylamine IR(neat,cm$^{-1}$): 2968,1602,1581,1479,1443,1278,1128,1056, 870.

$^1$H-NMR(300 MHz,CDCl$_3$,δ ppm):1.03(3H,t,J=7.2 Hz),1.23(9H, s),2.59(2H,q,J=7.2 Hz),2.71(2H,t,J=6.0 Hz),3.20(2H,d,J=6.3 Hz),3.65(2H,t,J=6.0 Hz),3.83(2H,t,J=4.9 Hz),4.16(2H, t,J=4.9 Hz),5.63(1H,dt,J=15.9 Hz,1.5 Hz),6.05(1H,dt,J=15.9 Hz,6.3 Hz),6.90(1H,ddd,J=8.1 Hz,2.7 Hz,2.7 Hz),7.14 (1H,dd,J=2.7 Hz,1.8 Hz,),7.17(1H,ddd,J=8.1 Hz,1.8 Hz,1.8 Hz),7.32(1H,t,J=8.1 Hz),8.07(1H,s),8.74(1H,s).

EXAMPLE 16

(E)-N-ethyl-N-(6,6-dimethyl-2-hepten-4-ynyl)-2-[2-[3-(3-pyridyl)phenoxy]ethoxy]ethylamine IR(neat,cm$^{-1}$): 2968,1605,1476,1302,1218,1128,1056,783.

$^1$H-NMR(300 MHz,CDCl$_3$,δ ppm):1.03(3H,t,J=7.1 Hz),1.23(9H, s),2.58(2H,q,J=7.1 Hz),2.71(2H,t,J=6.0 Hz),3.20(2H,d,J=6.3 Hz),3.65(2H,t,J=6.0 Hz),3.84(2H,t,J=4.8 Hz),4.18(2H, t,J=4.8 Hz),5.62(1H,dt,J=15.9 Hz,1.3 Hz),6.05(1H,dt,J=15.9 Hz,6.3 Hz),6.96(1H,ddd,J=8.4 Hz,2.4 Hz,2.4 Hz),7.13 (1H,dd,J=2.4 Hz,1.8 Hz),7.16(1H,ddd,J=7.5 Hz,2.4 Hz,1.8 Hz),7.35(1H,ddd,J=8.2 Hz,5.1 Hz,1.0 Hz),7.38(1H,t,J=8.1 Hz),7.86(1H,ddd,J=8.2 Hz,2.6 Hz,1.8 Hz),8.59(1H,dd,J=5.0 Hz,1.8 Hz),8.34(1H,d,J=2.7 Hz,1.0 Hz).

EXAMPLE 17

(E)-N-ethyl-N-(6,6-dimethyl-2-hepten-4-ynyl)-2-[2-[3-(1-imidazolyl)phenoxy]ethoxy]ethylamine IR(neat,cm$^{-1}$): 2968,1611,1509,1215,1128,1056.

$^1$H-NMR(300 MHz,CDCl$_3$,δ ppm):1.02(3H,t,J=7.5 Hz),1.23(9H, s),2.56(2H,q,J=7.5 Hz),2.68(2H,t,J=6.0 Hz),3.17(2H,dd,J=6.6 Hz,1.5 Hz,),3.63(2H,t,J=6.0 Hz),3.83(2H,t,J=6.0 Hz), 4.16(2H,t,J=6.0 Hz),5.64(1H,dt,J=15.6 Hz,1.5 Hz),6.03(1H, dt,J=15.6 Hz,6.6 Hz),6.91(1H,ddd,J=8.4 Hz,2.4 Hz,1.2 Hz), 6.94-6.99(2H,m),7.19(1H,t,J=1.2 Hz),7.27(1H,t,J=1.2 Hz), 7.36(1H,ddd,J=8.4 Hz,8.2 Hz,0.6 Hz),7.84(1H,t,J=1.2 Hz).

EXAMPLE 18

(E)-N-(6-ethoxy-6-methyl-2-hepten-4-ynyl)-N-propyl-5-[3-(3-thienyl)phenoxy]pentylamine hydrochloride m.p.:62°-64° C.

IR(KBr,cm$^{-1}$): 2980,2938,2878,1605,1584,1455,1290,1221, 1188,1161,1068,966,777.

$^1$H-NMR(300 MHz,CDCl$_3$,δ ppm):1.00(3H,t,J=7.3 Hz),1.20(3H,t, J=6.8 Hz),1.47(6H,s),1.50-1.70(4H,m),1.80-2.00(6H,m), 2.70-3.00(4H,m),3.57(2H,q,J=7.3 Hz),3.66(2H,d,J=7.6 Hz), 4.02(2H,t,J=6.0 Hz),5.88(1H,d,J=15.5 Hz),6.29(1H,dt,J=15.5 Hz,7.6 Hz),6.81(1H,ddd,J=8.0 Hz,2.8 Hz,0.9 Hz),7.11 (1H,dd,J=2.8 Hz,1.8 Hz),7.18(1H,ddd,J=7.5 Hz,1.8 Hz,0.9 Hz),7.30(1H,dd,J=8.0 Hz,7.5 Hz),7.36-7.40(2H,m),7.45(1H, dd,J=2.7 Hz,2.0 Hz).

EXAMPLE 19

(E)-N-(6-ethoxy-6-methyl-2-hepten-4-ynyl)-N-propyl-2-[2-[3-(3-thienyl)phenoxy]ethoxy]ethylamine hydrochloride m.p.:110°-111° C.

IR(KBr,cm$^{-1}$): 2986,2932,2632,1602,1452,1245,1224,1134, 1065,966,777.

¹H-NMR(300 MHz,CDCl₃,δ ppm):0.96(3H,t,J=7.2 Hz),1.18(3H,t, J=7.2 Hz),1.45(6H,s),1.82–1.90(2H,m),2.96–3.02(2H,m), 3.22(2H,t,J=4.5 Hz),3.54(2H,q,J=7.2 Hz),3.79(2H,d,J=7.3 Hz),3.87–3.90(2H,m),4.09–4.10(2H,m),4.16–4.20(2H, m),5.89(1H,d,J=15.9 Hz),6.29(1H,dt,J=15.9 Hz,7.3 Hz), 6.83(1H,ddd,J=8.0 Hz,2.3 Hz,0.9 Hz),7.13(1H,dd,J=2.3 Hz, 1.8 Hz),7.21(1H,ddd,J=7.8 Hz,1.8 Hz,0.9 Hz),7.31(1H,dd,J=8.0 Hz,7.8 Hz),7.37(1H,dd,J=4.9 Hz,1.3 Hz),7.38(1H,dd,J=4.9 Hz,2.6 Hz),7.45(1H,dd,J=2.6 Hz,1.3 Hz).

EXAMPLE 20

N-ethyl-N-(6,6-dimethyl-2,4-heptadiynyl)-2-[2-[3-(3-thienyl)phenoxy]ethoxy]ethylamine IR(neat,cm⁻¹): 2974,1605,1455,1287,1128,1059.

¹H-NMR (300 MHz,CDCl₃,δ ppm):1.06(3H,t,J=7.0 Hz),1.24(9H, s),2.60(2H,q,J=7.0 Hz),2.76(2H,t,J=5.7 Hz),3.55(2H,s), 3.67(2H,t,J=5.7 Hz),3.84(2H,t,J=5.0 Hz),4.18(2H,t,J=5.0 Hz),6.85(1H,ddd,J=7.8 Hz,2.3 Hz,1.0 Hz),7.14–7.22(2H, m),7.30(1H,t,J=7.8 Hz),7.37(2H,d,J=2.2 Hz),7.44(1H,t,J=2.2 Hz).

EXAMPLE 21

Production of (E,E)-N-ethyl-N-(6,6-dimethyl-2-hepten-4-ynyl)-5-[3-(3-thienyl)phenoxy)-2-pentenylamine 90 mg of 5-[3-(3-thienyl)phenoxy]-2-penten-1-ol was dissolved in 3 ml of ethyl acetate, and 69 μl of triethylamine and 34 μl of methanesulfonyl chloride were added with ice cooling and stirring. The solution was stirred for 30 minutes, and then water and ethyl acetate were added. The organic layer was separated, washed with a saturated aqueous solution of sodium chloride, and dried over anhydrous magnesium sulfate. The desiccant was separated by filtration, and the solvent was evaporated under reduced pressure. The residue was dissolved in 2 ml of dimethylformamide, and 101 mg of (E)-N-ethyl-6,6-dimethyl-2-hepten-4-ynylamine hydrochloride, 69 mg of potassium carbonate and 83 mg of potassium iodide were added. The mixture was stirred s overnight at room temperature, and then ethyl ether and water were added. The organic layer was separated, washed with a saturated aqueous solution of sodium chloride, and dried over anhydrous magnesium sulfate. The desiccant was separated by filtration, and the solvent was evaporated under reduced pressure. The residue was purified by medium-pressure liquid chromatography [silica gel column, hexane/ethyl acetate=15/1→15/2]]to give 68 mg (yield 49%) of the captioned compound as a colorless oil.

IR(neat,cm⁻¹): 2968,1605,1584,1455,1287,1221,1128,1059, 774.

¹H-NMR(300 MHz,CDCl₃,δ ppm):1.02(3H,t,J=7.1 Hz),1.23(9H, s),2.50(2H,q,J=7.1 Hz),2.45–2.60(2H,m),3.08(2H,d,J=5.1 Hz),3.10(2H,d,J=6.5 Hz),4.04(2H,t,J=7.0 Hz),5.56–5.74(3H,m),6.04(1H,dd,J=15.9 Hz,6.6 Hz),6.83(1H,ddd,J=8.4 Hz,3.0 Hz,2.1 Hz),7.12(1H,dd,J=3.0 Hz,2.1 Hz),7.17(1H, ddd,J=7.5 Hz,3.0 Hz,2.1 Hz),7.29(1H,t,J=7.8 Hz),7.37(2H,d, J=2.1 Hz),7.44(1H,t,J=2.1 Hz).

Compounds of Examples 22 and 23 were obtained by performing the same reaction as in Example 21 except that (E)-4-[3-(3-thienyl)benzyloxy]-2-buten-1-ol and/or the corresponding 2-hepten-4-ynylamine derivative were used instead of the starting compounds, (E)-5-[3-(3-thienyl)phenoxy]-2-penten-1-ol, which were used in the above-mentioned reaction.

EXAMPLE 22

(E,E)-N-ethyl-N-(6-methoxy-6-methyl-2-hepten-4-ynyl)-4-[3-(3-thienyl)benzyloxy]-2-butenylamine IR(neat,cm⁻¹) 2980,2938,1173,1149,1074,774.

¹H-NMR(300 MHz,CDCl₃,δ ppm):1.03(3H,t,J=7.0 Hz),1.46(6H, s),2.51(2H,q,J=7.0 Hz),3.10(2H,dd,J=4.0 Hz,1.3 Hz),3.13 (2H,dd,J=6.6 Hz,1.4 Hz),3.35(3H,s),4.04(2H,dd,J=3.4 Hz, 1.4 Hz),4.55(2H,s),5.66(1H,dt,J=15.8 Hz,1.4 Hz),5.75–5.78(2H,m),6.13(1H,dt,J=15.8 Hz,6.6 Hz),7.24–7.28(1H,m), 7.34–7.41(3H,m),7.46(1H,dd,J=2.8 Hz,1.7 Hz),7.51(1H,dt, J=7.8 Hz,1.2 Hz),7.56–7.58(1H,m).

EXAMPLE 23

(E,E)-N-ethyl-N-(6,6-dimethyl-2-hepten-4-ynyl)-4-[3-(3-thienyl)benzyloxy]-2-butenylamine IR(neat,cm⁻¹): 2974,2932,1365,1107,774.

¹H-NMR(300 MHz,CDCl₃,δ ppm):1.03(3H,t,J=7.1 Hz),1.24(9H, s),2.53(2H,q,J=7.1 Hz),3.04–3.20(4H,m),4.03–4.06(2H,m), 4.55(2H,s),5.63(1H,dt,J=15.9 Hz,1.5 Hz),5.75–5.80(2H,m), 6.04(1H,dt,J=15.9 Hz,6.6 Hz),7.24–7.42(4H,m),7.46(1H,dd, J=2.7 Hz,1.7 Hz),7.52(1H,dt,J=7.3 Hz,1.6 Hz),7.56–7.59(1H, m).

EXAMPLE 24

Production of (E)-N-ethyl-N-(6,6-dimethyl-2-hepten-4-ynyl)-5-[3-(3-thienyl)phenoxy]-4-oxopentylamine 50 mg of 5-bromo-1-[3-(3-thienyl)phenoxy]-2-pentanone was dissolved in 1.8 ml of dimethylformamide, and 125 mg of a (E)-N-ethyl-6,6-dimethyl-2-hepten-4-ynylamine hydrochloride and 29 mg of potassium iodide were added. The mixture was stirred at 40° C. for 1 hour, and then ethyl ether and ice water were added. The organic layer was separated, washed with a saturated aqueous solution of sodium chloride, and dried over anhydrous magnesium sulfate. The desiccant was separated by filtration, and the solvent was evaporated under reduced pressure. The residue was purified by silica gel column chromatography [hexane→chloroform] to give 20 mg (yield 27%) of the captioned compound as a colorless oil.

IR(neat,cm⁻¹): 2968,2926,1728,1605,1584,1458,1218,774.

¹H-NMR(300 MHz,CDCl₃,δ ppm):0.97(3H,t,J=7.1 Hz),1.23(9H, s),1.79(2H,q,J=7.1 Hz),2.42(2H,t,J=7.1 Hz),2.48(2H,q,J= 7.1 Hz),2.62(2H,t,J=7.1 Hz),3.07(2H,dd,J=6.6 Hz,1.5 Hz), 4.62(2H,s),5.60(1H,dt,J=14.5 Hz,1.5 Hz),6.00(1H,dt,J=14.5 Hz,6.6 Hz),6.80(1H,dd,J=7.1 Hz,2.8 Hz),7.14(1H,t,J=1.6 Hz),7.23(1H,dt,J=7.8 Hz,1.2 Hz),7.29(1H,t,J=10.5 Hz), 7.35–7.40(2H,m),7.45(1H,dd,J=2.6 Hz,1.4 Hz).

EXAMPLE 25

Production of
(E,E)-N-ethyl-N-(6,6-dimethyl-2-hepten-4-ynyl)-2-[3-[3-(3-thienyl)phenyl]-2-propenyloxy]ethylamine hydrochloride 3.7 g of (E)-2-[3-[3-(3-thienyl)phenyl]-2-propenyloxy]ethanol was dissolved in 100 ml of ethyl acetate, and 1.4 ml of methanesulfonyl chloride and 4.0 ml of triethylamine were added under ice cooling. The mixture was stirred for 30 minutes, and then the precipitate was removed by filtration. The solvent was evaporated under reduced pressure and the residue was dissolved in 100 ml of dimethylformamide. 4.3g of (E)-N-ethyl-6,6-dimethyl-2-hepten-4-ynylamine hydrochloride, 2.6 g of potassium iodide and 3.9 g of potassium carbonate were added, the mixture was heated at 90° C. for 4 hours. The solvent was evaporated under reduced pressure, and ethyl acetate and water were added to the residue to extract it. The organic layer was separated, washed with a saturated aqueous solution of sodium s chloride, and dried over anhydrous magnesium sulfate. The desiccant was separated by filtration, and the solvent was evaporated under reduced pressure. The residue was purified by silica gel column chromatography [hexane/ethyl acetate=2/1] to give 4.5 g (yield 76%) of free base of the captioned compound as a pale yellow oil.

The resulting free base (4.5 g) was dissolved in methanol, treated with a hydrogen chloride-methanol solution and recrystallized from ethyl ether to give 3.9 g of the captioned compound as a white crystalline powder, 133°-134° C.

IR(KBr,cm$^{-1}$):
2968,2866,2566,2470,1461,1365,1266,1137, 978,771.
$^1$H-NMR(300 MHz,CDCl$_3$,δ ppm):1.23(9H,s),1.44(3H,t,J=7.5 Hz),3.10-3.30(4H,m),3.78-3.82(2H,m),3.95-4.15(2H,m), 4.21(2H,d,J=6.3 Hz),5.89(1H,d,J=15.6 Hz),6.21(1H,dt,J=15.6 Hz,7.5 Hz),6.30(1H,dt,J=15.9 Hz,6.3 Hz),6.65(1H,d,J=15.9 Hz),7.30-7.36(2H,m),7.39(2H,d,J=2.1 Hz),7.46-7.51 (2H,m),7.59-7.61(1H,m).

Compounds of Examples 26 to 29 were obtained by performing the same reaction as in Example 25 except that the corresponding alcohol derivatives and/or 2-hepten-4-ynylamine derivatives were used instead of the starting compounds, (E)-2-[3-[3-(3-thienyl)phenyl]-2propenyloxy]ethanol and/or (E)-N-ethyl-6,6-dimethyl-2-hepten-4-ynylamine hydrochloride, which were used in the above-mentioned reaction.

EXAMPLE 26

(E,E)-N-ethyl-N-(6,6-dimethyl-2-hepten-4-ynyl)-2-[3-[4-( 3-thienyl)-2-thienyl]-2-propenyloxy]ethylamine IR(neat,cm$^{-1}$):
2968,1458,1365,1266,1203,1107,957,837, 783,750.
$^1$H-NMR(300 MHz,CDCl$_3$,δ ppm):1.04(3H,t,J=7.2 Hz),1.23(9H, s),2.59(2H,q,J=7.2 Hz),2.70(2H,t,J=6.0 Hz),3.19(2H,dd,J=6.6 Hz,1.5 Hz),3.57(2H,t,J=6.0 Hz),4.12(2H,dd,J=6.0 Hz, 1.5 Hz),5.64(1H,dt,J=15.9 Hz,1.5 Hz),6.06(1H,dt,J=15.9 Hz, 6.6 Hz),6.15(1H,dt,J=15.9 Hz,6.0 Hz),6.72(1H,dt,J=15.9 Hz, 1.5 Hz),7.16-7.20(2H,m),7.27-7.35(3H,m).

EXAMPLE 27

(E)-N-ethyl-N-(6,6-dimethyl-2-hepten-4-ynyl)-2-[2-[3-(3-thienyl)phenoxy]ethoxy]ethylamine hydrochloride
m.p.:79° C.

IR(KBr,cm$^{-1}$):
3442,2968,2578,2482,1602,1452,1287,1122, 777.
$^1$H-NMR(300 MHz,CDCl$_3$,δ ppm):1.27(9H,s),1.04(3H,t,J=6.7 Hz),3.10-3.30(4H,m),3.76-3.80(2H,m),3.88-3.90(2H,m), 4.07-4.10(1H,m),4.13-4.19(3H,m),5.85(1H,d,J=15.8 Hz), 6.17(1H,dt,J=15.8 Hz,7.3 Hz),6.83(1H,ddd,J=8.1 Hz,2.7 Hz, 2.4 Hz),7.13(1H,t,J=2.4 Hz),7.21(1H,dt,J=6.9 Hz,1.8 Hz), 7.31(1H,t,J=8.1 Hz),7.35-7.40(2H,m),7.45(1H,dd,J=3.3 Hz, 1.2 Hz).

EXAMPLE 20

(E)-N-ethyl-N-(6-methoxy-6-methyl-2-hepten-4-ynyl)-2-1-methyl-2-[3-(3-thienyl)phenoxy]ethoxy]ethylamine IR(neat,cm$^{-1}$):
2980,2932,1605,1452,1287,1221,1173,1152, 1074,771.
$^1$H-NMR(300 MHz,CDCl$_3$,δ ppm):1.02(3H,t,J=7.0 Hz),1.29(3H,d, J=6.0 Hz),1.45(6H,s),2.57(2H,q,J=7.0 Hz),2.68(2H,t,J=6.0 Hz),3.20(2H,dd,J=6.4 Hz,1.6 Hz),3.34(3H,s),3.65(1H, dt,J=12.0 Hz,6.0 Hz),3.68(1H,dt,J=12.0 Hz,6.0 Hz),3.80-3.89(1H,m),3.91(1H,dt,J=15.9 Hz,1.6 Hz),6.15(1H,dt,J=15.9 Hz,6.4 Hz),6.84(1H,ddd,J=8.0 Hz,2.8 Hz,1.0 Hz),7.14 (1H,dd,J=2.5 Hz,2.4 Hz),7.19(1H,ddd,J=7.5 Hz,1.8 Hz,0.9 Hz),7.30(1H,t,J=7.9 Hz),7.36-7.38(2H,m),7.44(1H,t,J=2.0 Hz).

EXAMPLE 29

(E)-N-ethyl-N-(6-methoxy-6-methyl-2-hepten-4-ynyl)-2-2-[3-(3-thienyl)phenoxy1ethoxy]propylamine IR(neat,cm$^{-1}$):
2980,2932,1605,1584,1452,1287,1221,1173, 1149,1122,1074,771.
$^1$H-NMR(300 MHz,CDCl$_3$,δ ppm):1.01(3H,t,J=7.3 Hz),1.19(3H,d, J=6.1 Hz),1.45(6H,s),2.39(1H,dd,J=13.4 Hz,5.4 Hz),2.60 (1H,dd,J=13.4 Hz,6.4 Hz),2.49-2.61(2H,m),3.17(1H,ddd,J=15.0 Hz,6.8 Hz,1.4 Hz),3.22(1H,ddd,J=15.0 Hz,6.8 Hz,1.4 Hz), 3.34(3H,s),3.58-3.69(1H,m),3.83(1H,dt,J=10.7 Hz,5.3 Hz), 3.89(1H,dt,J=10.7 Hz,5.3 Hz),4.15(2H,t,J=5.3 Hz),5.67(1H, dt,J=15.8 Hz,1.4 Hz),6.15(1H,dt,J=15.8 Hz,6.8 Hz),6.85(1H, ddd,J=8.5 Hz,2.9 Hz,1.3 Hz),7.15(1H,dd,J=2.2 Hz,1.7 Hz), 7.18(1H,ddd,J=7.5 Hz,1.4 Hz,1.2 Hz),7.29(1H,t,J=7.5 Hz), 7.37(2H,m),7.44(1H,dd,J=2.4 Hz,2.0 Hz).

EXAMPLE 30

Production of (E,E)-N-ethyl-N-(6-methoxy-6-methyl-2-hepten-4-ynyl)-5-[3-(3-thienyl)-2-propenyloxymethyl]-2-furylmethylamine hydrochloride 18.0 g of (E)-N-ethyl-5-[3-(3-thienyl)-2-propenyloxymethyl]-2-furylmethylamine was dissolved in 400 ml of dimethylformamide, and 13.0 g of (E)-6-methoxy-6-methyl-2-hepten-4-ynyl bromide (contaminated with about 5 wt % of the (Z)-isomer) and 18.0 g of potassium carbonate were added. The mixture was stirred at room temperature for 24 hours, and then ethyl ether and water were added. The organic layer was separated, washed with a saturated aqueous solution of sodium chloride, and dried over anhydrous magnesium sulfate. The desiccant was separated by filtration, and the solvent was evaporated under reduced pressure. The residue was purified by silica gel column chromatography [hexane/ethyl acetate=8/1→2/1] to give 21.8 g of free base of the captioned compound as a colorless oil.

The resulting free base was dissolved in 240 ml of ethyl ether, and to its solution was added, dropwise with stirring, 65 ml of a 0.5M hydrogen chloride-ethyl ether solution with stirring to give 22.3 g (yield 81%) of the captioned compound as a white crystalline powder, m.p. 91°-92.5° C.

IR(KBr,cm$^{-1}$):
2980,2914,2674,2608,1170,1098,1068,1056, 969,804.

$^1$H-NMR(300 MHz,CDCl$_3$,δ ppm):1.47(6H,s),1.51(3H,t,J=7.2 Hz),2.94-3.06(2H,m),3.34(3H,s),3.58-3.60(2H,m),4.17 (2H,dd,J=1.4 Hz,7.0 Hz),4.23(2H,br.s),4.48(2H,s),5.92 (1H,d,J=15.9 Hz),6.11(1H,dt,J=15.9 Hz,6.2 Hz),6.40(1H,d, J=3.2 Hz),6.45(1H,dt,J=15.9 Hz,7.0 Hz),6.62(1H,d,J=15.9 Hz),6.67(1H,d,J=3.2 Hz),7.18(1H,d,J=3.0 Hz),7.20(1H,dd, J=5.2 Hz,1.2 Hz),7.28(1H,dd,J=5.2 Hz,3.0 Hz).

Compounds of Examples 31 to 44 were obtained by performing the same reaction as in Example 30 except that the corresponding amine derivatives and/or alkynyl bromide derivatives were used instead of the starting compounds, (E)-N-ethyl-5-[3-(3-thienyl)-2-propenyloxymethyl]-2-furylmethylamine and/or (E)-6-methoxy-6-methyl-2-hepten-4-ynyl bromide, which were used in the above-mentioned reaction.

EXAMPLE 31

(E)-N-(2-fluoroethyl)-N-(6,6-dimethyl-2-hepten-4-ynyl)-2-[2-[3-(3-thienyl)phenoxy]ethoxy]ethylamine hydrochloride m.p. 109°-111° C.
IR(KBr,cm$^{-1}$):
2974,2596,2530,1599,1452,1284,1272,1221, 1131,1092,1062,960,840,774.

$^1$H-NMR(300 MHz,CDCl$_3$,δ ppm):1.22(9H,s),3.34-3.60(4H,m), 3.84-3.89(4H,m),4.-10-4.19(4H,m),4.97(2H,d,J=47.6 Hz), 5.87(1H,d,J=15.9 Hz),6.22(1H,dt,J=15.9 Hz,7.6 Hz),6.83 (1H,ddd,J=8.0 Hz,2.3 Hz,1.0 Hz),7.13(1H,dd,J=2.3 Hz,1.5 Hz),7.21(1H,ddd,J=7.8 Hz,1.5 Hz,1.0 Hz),7.31(1H,dd,J=8.0 Hz,7.8 Hz),7.37(1H,dd,J=5.1 Hz,1.7 Hz),7.38(1H,dd,J=5.1 Hz,2.7 Hz),7.46(1H,dd,J=2.7 Hz,1.7 Hz).

EXAMPLE 32

(E)-N-cyclopropyl-N-(6,6-dimethyl-2-hepten-4-ynyl)-2-[2-[3-(3-thienyl)phenoxy]ethoxy]ethylamine hydrochloride m.p. 86°-88° C.
IR(KBr,cm$^{-1}$):
3450,2974,2560,1596,1452,1221,1131,1089, 1062,777.

$^1$H-NMR(300 MHz,CDCl$_3$,δ ppm):0.78-0.85(4H,m),1.22(9H,s), 2.40-2.60(1H,m),3.-24-3.27(2H,m),3.65-4.30(4H,m),3.87 (2H,t,J=4.8 Hz),4.19(2H,t,J=4.8 Hz),5.86(1H,d,J=16.2 Hz), 6.19(1H,dt,J=16.2 Hz,7.2 Hz),6.82-6.86(1H,m),7.13(H,t,J=1.8 Hz),7.31(1H,t,J=7.8 Hz).

EXAMPLE 33

(E)-N-ethyl-N-(6,6-dimethyl-2-hepten-4-ynyl)-2-[2-[3-(3-thienyl)phenoxy]ethylthio]ethylamine IR(neat,cm$^{-1}$)
2974,1605,1584,1455,1287,1218,1182,771.

$^1$H-NMR(300 MHz,CDCl$_3$,δ ppm):1.03(3H,t,J=7.1 Hz),1.23(9H, s),2.55(2H,q,J=7.1 Hz),2.71(4H,s),2.94(2H,t,J=6.5 Hz), 3.14(2H,dd,J=6.3 Hz,1.5 Hz),4.19(2H,t,J=6.9 Hz),5.64(1H, dt,J=15.9 Hz,1.5 Hz),6.04(1H,dt,J=15.9 Hz,6.3 Hz),6.84(1H, dd,J=8.1 Hz,2.7 Hz),7.13(1H,t,J=2.1 Hz),7.20(1H,dd,J=7.8 Hz,1.8 Hz),7.31(1H,t,J=7.8 Hz),7.35(2H,d,J=2.7 Hz), 7.45(1H,dd,J=2.1 Hz,2.1 Hz).

EXAMPLE 34

(E)-N-cyclopropyl-N-(6-ethoxy-6-methyl-2-hepten-4-ynyl)-2-[2-[3-(3-thienyl)phenoxy]ethoxy]ethylamine hydrochloride m.p.:118°-120° C.
IR(KBr,cm$^{-1}$):
2566,1602,1449,1248,1224,1164,1128,1071, 981,777.

$^1$H-NMR(300 MHz,CDCl$_3$,δ ppm):0.81-0.98(2H,m),1.18(3H,t,J=7.2 Hz),1.44(6H,s),1.72-1.89(2H,m),2.49-2.60(1H,m), 3.32-3.40(2H,m),3.53(2H,q,J=7.2 Hz),3.78-3.90(3H,m), 3.90-4.09(2H,m),4.-11-4.30(3H,m),5.93(1H,d,J=15.8 Hz), 6.31(1H,dt,J=15.8 Hz,7.8 Hz),6.82(1H,ddd,J=8.0 Hz,2.3 Hz, 1.4 Hz),7.12(1H,dd,J=2.3 Hz,1.7 Hz),7.21(1H,ddd,J=8.0 Hz, 1.7 Hz,1.4 Hz),7.31(1H,dd,J=8.1 Hz,8.0 Hz),7.37(1H,dd,J=5.3 Hz,1.4 Hz),7.38(1H,dd,J=5.3 Hz,2.5 Hz),7.45(1H,dd,J=2.5 Hz,1.4 Hz).

EXAMPLE 35

(E)-N-ethyl-N-(6,6-dimethyl-2-octen-4-ynyl)-2-[2-[3-(3-thienyl)phenoxy]ethoxy]ethylamine hydrochloride m.p.:96.5°-98° C.
IR(KBr,cm$^{-1}$):
2974,2926,2626,1599,1464,1449,1221,1128, 1089,1062,774.

$^1$H-NMR(300 MHz,CDCl$_3$,δ ppm):0.94(3H,t,J=7.4 Hz),1.17(6H, s),1.40(3H,t,J=7.4 Hz),1.43(2H,q,J=7.4 Hz),3.11-3.19(2H, m),3.21(2H,t,J=4.6 Hz),3.77(2H,t,J=7.6 Hz),3.87-3.90(2H, m),4.10-4.15(2H,m),4.16-4.20(2H,m),5.87(1H,d,J=16.0 Hz), 6.18(1H,dt,J=16.0 Hz,7.6 Hz),6.83(1H,ddd,J=8.0 Hz, 2.8 Hz,1.0 Hz),7.13(1H,dd,J=2.8 Hz,1.9 Hz),7.20(1H,ddd,J=8.0 Hz,1.9 Hz,1.0 Hz),7.30(1H,t,J=8.0 Hz),7.35-7.40(2H,m), 7.45(1H,dd,J=2.7 Hz,1.7 Hz).

EXAMPLE 36

(E,E)-N-ethyl-N-(6,6-dimethyl-2-hepten-4-ynyl)-3-[5-(3-thienyl)-2,4-pentadienyl]benzylamine IR(neat,cm$^{-1}$): 2968,1263,1092,1038,987,801.

$^1$H-NMR(300 MHz,CDCl$_3$,δ ppm):1.04(3H,t,J=7.1 Hz),1.23(9H, s),2.51(2H,q,J=7.1 Hz),3.09(2H,dd,J=6.4 Hz,1.5 Hz),3.46 (2H,dd,J=6.7 Hz,1.5 Hz),3.54(2H,s),5.64(1H,dt,J=15.9 Hz, 1.5 Hz),5.92(1H,dt,J=15.2 Hz,6.7 Hz),6.08(1H,dt,J=15.9 Hz, 6.4 Hz),6.20(1H,ddt,J=15.2 Hz,10.1 Hz,1.5 Hz),6.49(1H,d,J=15.6 Hz),6.62(1H,dd,J=15.6 Hz,10.1

Hz),7.07(1H,d,J=7.4 Hz),7.11(1H,dd,J=3.1 Hz,1.2 Hz),7.07–7.24(5H,m).

EXAMPLE 37

(E,E)-N-ethyl-N-(2-fluoro-6,6-dimethyl-2-hepten-4-ynyl)-5-[3-(3-thienyl)-2-propenyloxymethyl]-2-furylmethylamine IR(neat,cm$^{-1}$):
2968,2860,1677,1365,1266,1101,1059,798.
$^1$H-NMR(300 MHz,CDCl$_3$,δ ppm):1.08(3H,t,J=7.1 Hz),1.26(9H, s),2.58(2H,q,J=7.1 Hz),3.21(2H,d,J=13.7 Hz),3.70(2H,s), 4.15(2H,dd,J=6.4 Hz,1.5 Hz),4.46(2H,s),5.04(1H,d,J=33.8 Hz),6.13(1H,dt,J=16.0 Hz,6.4 Hz),6.15(1H,d,J=3.0 Hz), 6.26(1H,d,J=3.0 Hz),6.62(1H,dt,J=16.0 Hz,1.5 Hz),7.16(1H, dd,J=3.0 Hz,1.2 Hz),7.21(1H,dd,J=5.1 Hz,1.2 Hz),7.26(1H, dd,J=5.1 Hz,3.0 Hz).

EXAMPLE 38

(E,E)-N-methyl-N-(6,6-dimethyl-2-hepten-4-ynyl)-5-[3-(3-thienyl)-2-propenyloxymethyl]-2-furylmethylamine IR(neat,cm$^{-1}$):
2968,2860,1365,1110,1065,1020,966,798.
$^1$H-NMR(300 MHz,CDCl$_3$,δ ppm):1.24(9H,s),2.23(3H,s),3.05 (2H,dd,J=6.9 Hz,1.5 Hz),3.53(2H,s),4.13(2H,dd,J=6.3 Hz, 1.5 Hz),4.46(2H,s),5.63(1H,dt,J=15.9 Hz,1.5 Hz),6.06(1H,dt, J=15.9 Hz,6.9 Hz),6.13(1H,dt,J=15.9 Hz,6.3 Hz),6.14(1H,d,J= 3.0 Hz),6.26(1H,d,J=3.0 Hz),6.62(1H,dt,J=15.9 Hz,1.5 Hz), 7.15(1H,dd,J=2.7 Hz,1.2 Hz),7.20(1H,dd,J=3.6 Hz,1.2 Hz), 7.25(1H,dd,J=3.6 Hz,2.7 Hz).

EXAMPLE 39

(E,E)-N-(6-methoxy-6-methyl-2-hepten-4-ynyl)-N-methyl-5-[3-(3-thienyl)-2-propenyloxymethyl]-2-furylmethylamine IR(neat,cm$^{-1}$):
2986,2938,2848,2794,1660,1560,1458,1362, 1248,1173,1074,966,768.
$^1$H-NMR(300 MHz,CDCl$_3$,δ ppm):1.46(6H,s),2.25(3H,s),3.08 (2H,dd,J=6.6 Hz,1.5 Hz),3.35(3H,s),3.54(2H,s),4.15(2H, dd,J=6.6 Hz,1.5 Hz),4.47(2H,s),5.68(1H,dt,J=15.6 Hz,1.5 Hz),6.09–6.21(3H,m),6.27(1H,d,J=3.3 Hz),6.62(1H,d,J=15.9 Hz),7.15(1H,dd,J=3.0 Hz,1.5 Hz),7.21(1H,dd,J=5.4 Hz, 1.5 Hz),7.25–7.27(1H,m).

EXAMPLE 40

(E,E)-N-ethyl-N-(6,6-dimethyl-2-hepten-4-ynyl)-5-[3-(3-thienyl)-2-propenyloxymethyl]-2-furylmethylamine IR(neat,cm$^{-1}$):
2968,2932,2866,1461,1365,1269,1200,1107, 1068,1020,966,795,768.
$^1$H-NMR(300 MHz,CDCl$_3$,δ ppm):1.06(3H,t,J=7.2 Hz),1.24(9H, s),2.51(2H,q,J=7.2 Hz),3.13(2H,dd,J=6.6 Hz,1.5 Hz),3.63 (2H,s),4.14(2H,dd,J=6.3 Hz,1.5 Hz),4.46(2H,s),5.65(1H, dt,J=15.9 Hz,1.5 Hz),6.05(1H,dt,J=15.9 Hz,6.6 Hz),6.13(1H, d,J=3.3 Hz),6.14(1H,dt,J=15.9 Hz,6.3 Hz),6.26(1H,d,J=3.3 Hz),6.62(1H,d,J=15.9 Hz),7.16(1H,dd,J=3.0 Hz,1.2 Hz), 7.21 (1H,dd,J=5.1 Hz,1.2 Hz),7.26(1H,dd,J=5.1 Hz,3.0 Hz).

EXAMPLE 41

(E,E)-N-(6-ethoxy-6-methyl-2-hepten-4-ynyl)-N-ethyl-5-[3-(3-thienyl)-2-propenyloxymethyl]-2-furylmethylamine IR(neat,cm$^{-1}$): 2980,2932,1161,1110,1071,966.
$^1$H-NMR(300 MHz,CDCl$_3$,δ ppm):1.07(3H,t,J=7.0 Hz),1.20(3H,t, J=7.1 Hz),1.47(6H,s),2.52(2H,q,J=7.0 Hz),3.15(2H,dd,J=6.6 Hz,1.5 Hz),3.59(2H,q,J=7.1 Hz),3.63(2H,s),4.14(2H,dd, J=6.0 Hz,1.5 Hz),4.46(2H,s),5.68(1H,dt,J=15.8 Hz,1.5 Hz), 6.08–6.20(3H,m),6.26(1H,d,J=3.2 Hz),6.62(1H,d,J=15.9 Hz),7.14–7.19(3H,m).

EXAMPLE 42

(E,E)-N-(6-methoxy-6-methyl-2-hepten-4-ynyl)-N-propyl-5-[3-(3-thienyl)-2-propenyloxymethyl]-2-furylmethylamine IR(neat,cm$^{-1}$): 2926,2854,1467,1173,1077,966,759.
$^1$H-NMR(300 MHz,CDCl$_3$,δ ppm):0.88(3H,t,J=7.3 Hz),1.46(6H, s),1.40–1.53(2H,m),2.37–2.42(2H,m),3.15(2H,dd,J=6.3 Hz, 1.5 Hz),3.36(3H,s),3.63(2H,s),4.14(2H,dd,J=6.3 Hz,1.5 Hz),4.46(2H,s),5.71(1H,dt,J,=16.0 Hz,1.5 Hz),6.13(1H,d, J=3.2 Hz),6.15(1H,dt,J=16.0 Hz,6.3 Hz),6.26(1H,d,J=3.2 Hz),6.62(1H,d,J=16.0 Hz),7.15(1H,dd,J=2.8 Hz,1.5 Hz), 7.21(1H,dd,J=5.2 Hz,1.5 Hz),7.26(1H,dd,J=5.2 Hz,2.8 Hz).

EXAMPLE 43

(E,E)-N-(2-fluoroethyl)-N-(6-methoxy-6-methyl-2-hepten-4-ynyl)-5-3-(3-thienyl)-2-propenyloxymethyl]-2-furylmethyl-amine IR(neat,cm$^{-1}$): 1173,1107,1074,1020,966,768.
$^1$H-NMR(300 MHz,CDCl$_3$,δ ppm):1.46(6H,s),2.81(2H,dt,J=26.4 Hz,5.0 Hz),3.24(2H,dd,J=1.5 Hz,6.3 Hz),3.35(3H,s),3.72 (2H,s),4.15(2H,dd,J=6.5 Hz,1.5 Hz),4.46(2H,s),4.51(2H, dt,J=44.7 Hz,5.0 Hz),5.71(1H,dt,J=15.8 Hz,1.5 Hz),6.08–6.20(3H,m),6.27(1H,d,J=2.8 Hz),6.62(1H,d,J=15.9 Hz), 7.16(1H,dd,J=3.0 Hz,1.2 Hz),7.21(1H,dd,J=5.1 Hz,1.2 Hz), 7.26(1H,dd,J=5.1 Hz,3.0 Hz).

EXAMPLE 44

(E,E)-N-cyclopropyl-N-(6-methoxy-6-methyl-2-hepten-4-ynyl)-5-3-(3-thienyl)-2-propenyloxymethyl]-2-furylmethylamine IR(neat,cm$^{-1}$): 2986,2932,1362,1170,1074,966.
$^1$H-NMR(300 MHz,CDCl$_3$,δ ppm):0.36–0.51(4H,m),1.46(6H,s), 1.82–1.90(1H,m),3.27(2H,dd,J=6.9 Hz,1.5 Hz),3.35(3H,s), 3.73(2H,s),4.14(2H,dd,J=6.1 Hz,1.5 Hz),4.46(2H,s),5.67 (1H,dt,J=15.9 Hz,1.5 Hz),6.08–6.22(3H,m),6.26(1H,d,J=2.8 Hz),6.62(1H,d,J=15.9 Hz),7.15(1H,dd,J=3.0 Hz,1.5 Hz), 7.21(1H,dd,J=5.1 Hz,1.5 Hz),7.26(1H,dd,J=5.1 Hz,3.0 Hz).

EXAMPLE 45

Production of
(E)-N-ethyl-N-(6,6-dimethyl-4-hepten-2-ynyl)-2-[2-[3-(3-thienyl)phenoxy]ethoxy]ethylamine 35 mg of (E)-6,6-dimethyl-4-hepten-2-yn-1-ol was dissolved in 2 ml of ethyl acetate, and 23 μl of methanesulfonyl chloride and 70 μl of triethylamine were added under ice cooling. The mixture was stirred for 30 min. The precipitate was removed by filtration, and the solvent was evaporated under reduced pressure. The residue was dissolved in 2 ml of dimethylformamide, and a dimethylformamide solution(2 ml) of 58 mg of N-ethyl- 2-[2-[3-(3-thienyl)phenoxy]ethoxy]ethylamine and 55 mg of potassium carbonate were added. The mixture was stirred overnight at room temperature and then ethyl ether and water were added. The organic layer was separated, washed with a saturated aqueous solution of sodium chloride, and dried over anhydrous magnesium sulfate. The desiccant was separated by filtration, and the solvent was evaporated. The residue was purified by silica gel column chromatography [hexane/ethyl acetate=4/1→2/1] to give 40 mg (yield 49%) of the captioned compound as a pale brown oil.

IR(neat,cm$^{-1}$): 2962,1287,1128,771.

$^1$H-NMR(300 MHz,CDCl$_3$,δ ppm):1.02(9H,s),1.08(3H,t,J=7.0 Hz),2.62(2H,q,J=7.2 Hz),2.78(2H,t,J=5.8 Hz),3.58(2H,d,J=1.6 Hz),3.70(2H,t,J=5.8 Hz),3.85(2H,t,J=5.0 Hz),4.18(2H,t,J=5.0 Hz),5.40(1H,dt,J=16.0 Hz,1.6 Hz),6.14(1H,d,J=16.0 Hz),6.85(1H,ddd,J=8.4 Hz,2.4 Hz,1.4 Hz),7.15-7.20(2H, m),7.30(3H,t,J=7.8 Hz),7.44(1H,t,J=2.2 Hz).

Compound of Example 46 to 49 was obtained by performing the same reaction as in Example 45 except that the corresponding 4-hepten-2-yn-1-ol or 2,4-heptadiyn-1-ol derivative, and 2-furylmethlamine derivative were used instead of the starting compound, (E)-6,6-dimethyl-4-hepten-2-yn-1-ol and N-ethyl-2-[2-[3-(3-thienyl)phenoxy]ethoxy]ethylamine, which were used in the above-mentioned reaction.

EXAMPLE 46

(E,E)-N-ethyl-N-(6,6-dimethyl-4-hepten-2-ynyl)-5-3-(3-thienyl)-2-propenyloxymethyl]-2-furylmethylamine IR(neat,cm$^{-1}$): 2962,2866,1365,1101,1068,1020,966,792,768.

$^1$H-NMR(300 MHz,CDCl$_3$,δ ppm):1.03(9H,s),1.11(3H,t,J=7.2 Hz),2.58(2H,q,J=7.2 Hz),3.49(2H,d,J=2.0 Hz),3.67(2H,s), 4.15(2H,dd,J=6.0 Hz,1.5 Hz),4.46(2H,s),5.43(1H,dt,J=16.5 Hz,2.0 Hz),6.14(1H,dt,J=15.9 Hz,6.0 Hz),6.16(1H,d,J=16.5 Hz),6.21(1H,d,J=3.2 Hz),6.26(1H,d,J=3.2 Hz),6.62(1H, d,J=15.9 Hz),7.15-7.27(3H,m).

EXAMPLE 47

(E,E)-N-(6-methoxy-6-methyl-2,4-heptadiynyl)-N-methyl-5-[3-(3-thienyl)-2-propenyloxymethyl]-2-furylmethylamine IR(neat,cm$^{-1}$): 2986,2938,1362,1269,1173,1110,1074,1020, 966,768.

$^1$H-NMR(300 MHz,CDCl$_3$,δ ppm):1.48(6H,s),2.36(3H,s),3.37 (3H,s),3.44(2H,s),3.60(2H,s),4.15(2H,dd,J=6.2 Hz,1.2 Hz),4.46(2H,s),6.13(1H,dt,J=15.6 Hz,6.2 Hz),6.22(1H,d,J=3.2 Hz),6.27(1H,d,J=3.2 Hz),6.62(1H,dt,J=15.6 Hz,1.2 Hz), 7.15(1H,dd,J=3.0 Hz,0.9 Hz),7.21(1H,dd,J=4.5 Hz,0.9 Hz), 7.26(1H,dd,J=4.5 Hz,3.0 Hz).

EXAMPLE 48

(E)-N-ethyl-N-(6-methoxy-6-methyl-2,4-heptadiynyl)-5-[3-(3-thienylmethoxy)-1-propenyl]-2-furylmethylamine IR(neat,cm$^{-1}$): 2986,2938,1266,1173,1134,1110,1074,966, 777.

$^1$H-NMR(300 MHz,CDCl$_3$,δ ppm):1.12(3H,t,J=7.2 Hz),1.47(6H, s),2.61(2H,q,J=7.2 Hz),3.37(3H,s),3.48(2H,s),3.67(2H, s),4.14(2H,dd,J=5.4 Hz,1.2 Hz),4.56(2H,s),6.18(1H,d,J=3.0 Hz),6.23(1H,d,J=3.0 Hz),6.23(1H,dt,J=15.9 Hz,5.4 Hz), 6.40(1H,dt,J=15.9 Hz,1.2 Hz),7.09(1H,dd,J=4.8 Hz,1.2 Hz), 7.22(1H,dd,J=2.7 Hz,1.2 Hz),7.30(1H,dd,J=4.8 Hz,2.7 Hz).

EXAMPLE 49

(E,E)-N-ethyl-N-(6-methoxy-6-methyl-4-hepten-2-ynyl)-5-[3-(3-thienyl)-2-propenyloxymethyl]-2-furylmethylamine IR(neat,cm$^{-1}$): 2980,2938,2416,1464,1197,1170,1110,1071, 1020,966.

$^1$H-NMR(300 MHz,CDCl$_3$,δ ppm):1.28(6H,s),1.49(3H,t,J=7.0 Hz),3.18(3H,s),3.12-3.20(2H,m),3.90-4.06(2H,m),4.16 (2H,dd,J=6.0 Hz,1.5 Hz),4.22-4.38(2H,m),4.48(2H,s),5.65 (1H,dt,J=16.4 Hz,1.5 Hz),6.12(1H,dt,J=1.60 Hz,6.0 Hz),6.24 (1H,d,J=16.4 Hz),6.40(1H,d,J=3.5 Hz),6.86(1H,d,J=3.5 Hz), 6.62(1H,d,J=16.0 Hz),7.16-7.22(2H,m),7.26-7.29(1H,m).

EXAMPLE 50

Production of (E)-N-ethyl-N-(6,6-dimethyl-4-heptynyl)-3-[3-(3-thienyl)-2-propenyloxymethyl]benzylamine 30 mg of (E)-N-ethyl-3-[3-(3-thienyl)-2-propenyloxymethyl]benzylamine was dissolved in 0.3 ml of dimethylformamide, and 22mg of 6,6-dimethyl-4-heptynyl methanesulfonate, 9.0 mg of potassium iodide and 6.0 μl of pyridine were added. The mixture was stirred at 50° C. for 4 hours, and then ethyl ether and water were added. The organic layer was separated, washed with a saturated aqueous solution of sodium chloride, and dried over anhydrous magnesium sulfate. The desiccant was separated by filtration, and the solvent was evaporated. The residue was purified by silica gel column chromatography [hexane/ethyl acetate=5/1] to give 11 mg (yield 26%) of the captioned compound as a colorless oil.

IR(neat,cm$^{-1}$): 2968,2866,1458,1365,1155,1110,1071,966, 765.

$^1$H-NMR(300 MHz,CDCl$_3$,δ ppm):1.03(3H,t,J=7.1 Hz),1.16(9H, s),1.63(2H,quint.,J=7.1 Hz),2.16(2H,t,J=7.1 Hz),2.49(2H, q,J=7.1 Hz),2.52(2H,t,J=7.1 Hz),3.56(2H,s),4.15(2H,dd,J=6.1 Hz,1.5 Hz),4.55(2H,s),6.17(1H,dt,J=15.9 Hz,6.1 Hz), 6.64(1H,dt,J=15.9 Hz,1.5 Hz),7.16(1H,dd,J=2.6 Hz,1.2 Hz), 7.18-7.31(2H,m).

Compound of Example 51 was obtained by performing the same reaction as in Example 51 was obtained by performing the same reaction as in Example 50 except that N-ethyl-2-[2-[3-(3-thienyl)phenoxy]ethoxy]ethylamine was used instead of the starting compound, (E)-N-ethyl-3-[3-(3-thienyl)-2-propenyloxymethyl] benzylamine, which was used in the above-mentioned reaction.

EXAMPLE 51

N-ethyl-N-(6,6-dimethyl-4-heptynyl)-2-[2-[3-(3-thienyl)phenoxy]ethoxy]ethylamine IR(neat,cm$^{-1}$):
2968,1605,1584,1455,1290,1269,1221,1188, 1128,1059,774.

$^1$H-NMR(300 MHz,CDCl$_3$,δ ppm):1.07(3H,t,J=7.1 Hz),1.18(9H, s),1.64(2H,quint.,J=7.4 Hz),2.16(2H,t,J=7.4 Hz),2.62(2H, t,J=7.4 Hz),2.63(2H,q,J=7.1 Hz),2.74(2H,t,J=6.4 Hz),3.68 (2H,t,J=6.4 Hz),3.85(2H,t,J=5.0 Hz),4.17(2H,t,J=5.0 Hz), 6.85(1H,ddd,J=8.0 Hz,2.3 Hz,0.9 Hz),7.15-7.21(2H,m),7.30 (1H,t,J=8.0 Hz),7.37(2H,d,J=1.8 Hz),7.44(2H,t,J=1.8 Hz).

EXAMPLE 52

Production of (E)-N-(6-methoxy-6-methyl-2-hepten-4-ynyl)-5-[3-(3-thienyl)phenoxy]pentylamine 100 mg of 5-[3-(3-thienyl)phenoxy]pentylamine and 100 mg of potassium carbonate were dissolved in 5 ml of dimethylformamide, and a dimethylformamide solution (0.5 ml) of 43 mg of (E)-6-methoxy-6-methyl-2-hepten-4-ynyl bromide (contaminated with about 5 wt % of the (Z)-isomer) was added dropwise over 30 minutes with stirring. The mixture was stirred at room temperature for 1 hour. The solvent was evaporated under reduced pressure, and ethyl acetate and water were added to the residue to extract it. The organic layer was separated, washed with a saturated aqueous solution of sodium chloride, and dried over anhydrous magnesium sulfate. The desiccant was separated by filtration, and the solvent was evaporated. The residue was purified by silica gel column chromatography [methylene chloride→methylene chloride/methanol=10/1] to give 31 mg (yield 39%) of the captioned compound as a pale yellow oil.

IR(neat,cm$^{-1}$): 2938,1605,1584,1218,1173,1074,771.
$^1$H-NMR(300 MHz,CDCl$_3$,δ ppm):1.45(6H,s),1.49-1.57(4H,m), 1.83(2H,q,J=7.0 Hz),2.64(2H,t,J=7.0 Hz),3.30(2H,dd,J=6.1 Hz,1.5 Hz),3.35(3H,s),4.00(2H,t,J=7.0 Hz),5.67(1H,dt, J=16.2 Hz,1.5 Hz),6.19(1H,dt,J=16.2 Hz,6.1 Hz),6.82(1H, ddd,J=7.5 Hz,2.7 Hz,0.9 Hz),7.12(1H,dd,J=2.7 Hz,0.9 Hz), 7.17(1H,dt,J=7.5 Hz,0.9 Hz),7.30(1H,t,J=7.5 Hz),7.37(2H, d,J=2.2 Hz),7.44(1H,d,J=2.2 Hz).

Compound of Example 53 was obtained by performing the same reaction as in Example 52 except that 2-[2-[3-(3-thienyl)phenoxy]ethoxy]ethylamine and (E)-6,6-dimethyl-2-hepten-4-ynyl bromide were used instead of the starting compounds, 5-[3-(3-thienyl)phenoxy]pentylamine and (E)-6-methoxy-6-methyl-2-hepten-4-ynyl bromide, which were used in the above-mentioned reaction.

EXAMPLE 53

(E)-N-(6,6-dimethyl-2-hepten-4-ynyl)-2-[2-[3-(3-thienyl)phenoxy]ethoxy]ethylamine hydrochloride m.p.:105°-107° C.
IR(KBr,cm$^{-1}$):
2968,2770,1611,1584,1452,1290,1269,1218, 1188,1134,1068,765.

$^1$H-NMR(300 MHz,CDCl$_3$,δ ppm):1.20(9H,s),3.14(2H,t,J=5.0 Hz),3.71(2H,d,J=7.1 Hz),3.80-3.90(2H,m),3.96(2H,t,J=5.0 Hz),4.19-4.23(2H,m),5.84(1H,d,J=15.6 Hz),6.16(1H,dt, J=15.6 Hz,7.1 Hz),6.84(1H,ddd,J=7.5 Hz,2.4 Hz,1.0 Hz),7.15-7.21(2H,m),7.29(1H,t,J=7.5 Hz),7.34-7.40(2H,m),7.45-7.48(1H,m).

EXAMPLE 54

Production of (E)-N-(6,6-dimethyl-2-hepten-4-ynyl)-N-propargyl-2-[2-[3-(3-thienyl)phenoxy]ethoxy]ethylamine hydro-chloride 680 mg of (E)-N-(6,6-dimethyl-2-hepten-4-ynyl)-2-[2-[3-(3-thienyl)phenoxy]ethoxy]ethylamine was dissolved in 50 ml of dimethylformamide, and 300 mg of propargyl bromide and 500 mg of potassium carbonate were added. The mixture was stirred under ice cooling for 3 hours. The solvent was evaporated under reduced pressure, and the residue was dissolved in ethyl ether. An insoluble material was removed by filtration, and the filtrate was evaporated under reduced pressure. The residue was then purified by silica gel short column chromatography, followed by medium-pressure liquid chromatography [silica gel column, methylene chloride/methanol=20/1] to give 350 mg (yield 61%) of free base of the captioned compound as a colorless oil. The resulting free base was treated with a hydrogen chloride-methanol solution and crystallized from ethyl ether to give the captioned compound as a colorless crystalline powder, m.p. 111°-113° C.

IR(KBr,cm$^{-1}$):
2968,2932,2380,2314,1605,1584,1452,1290, 1221,1188,1137,1068,774.

$^1$H-NMR(300 MHz,CDCl$_3$,δ ppm):1.23(9H,s),2.57(1H,s),3.31 (2H,m),3.61-4.32(10H,m),5.89(2H,d,J=15.9 Hz),6.29(2H, dt,J=15.9 Hz,6.3 Hz),6.84(1H,ddd,J=8.0 Hz,2.3 Hz,1.0 Hz), 7.15(1H,dd,J=2.3 Hz,1.4 Hz),7.20(1H,ddd,J=7.5 Hz,1.4 Hz, 1.0 Hz),7.31(1H,dd,J=8.0 Hz,7.5 Hz),7.38(2H,d,J=2.2 Hz), 7.46(1H,t,J=2.2 Hz).

Compound of Example 55 was obtained by performing the same reaction as in Example 54 except that allyl bromide was used instead of the starting compound, propargyl bromide, which was used in the above-mentioned reaction.

EXAMPLE 55

(E)-N-allyl-N-(6,6-dimethyl-2-hepten-4-ynyl)-2-[2-[3-(3-thienyl)phenoxy]ethoxy]ethylamine IR(neat,cm$^{-1}$):
2968,1605,1452,1365,1287,1221,1185,1128, 1047,963,771.

$^1$H-NMR(300 MHz,CDCl$_3$,δ ppm):1.23(9H,s),2.69(2H,t,J=5.9 Hz),3.14(2H,d,J=6.4 Hz),3.18(2H,dd,J=6.6 Hz,1.5 Hz),3.64 (2H,t,J=5.9 Hz),3.82(2H,t,J=4.9 Hz),4.16(2H,t,J=4.9 Hz), 5.09-5.20(2H,m),5.62(1H,dt,J=15.9 Hz),1.5 Hz),5.83(1H, ddt,J=17.0 Hz,9.8 Hz,6.4 Hz),6.04(1H,dt,J=1.59 Hz),6.6 Hz), 6.85(1H,ddd,J=7.9 Hz,2.3 Hz,1.0 Hz),7.15-7.20(2H,m),7.30 (1H,t,J=7.9 Hz),7.37(2H,d,J=2.5 Hz),7.44(1H,t,J=2.5 Hz).

EXAMPLE 56

Production of
(E)-N-ethyl-N-(7,7,7-trifluoro-6-trifluoromethyl-6-methoxy-2-hepten-4-ynyl)-2-[2-[3-(3-thienyl)-phenoxy]ethoxy]ethylamine 159 mg of (E)-ethyl-N-(7,7,7-trifluoro-6-trifluoromethyl-6-hydroxy-2-hepten-4-ynyl)-2-[2-[3-(3-thienyl)phenoxy]ethoxy]ethylamine was dissolved in 2 ml of dimethylformamide, and 24 mg of 60% oily sodium hydride was added. The mixture was stirred at room temperature for 10 minutes. To this solution was added 60 μl of dimethyl sulfate, and then the mixture was stirred at room temperature for 4 hours. The solvent was evaporated under reduced pressure, and ethyl acetate and water were added to the residue to extract it. The organic layer was separated, washed with a saturated aqueous solution of sodium chloride, and dried over anhydrous magnesium sulfate. The desiccant was separated by filtration, and the solvent was evaporated. The residue was purified by silica gel column chromatography [methylene chloride/methanol=70/1] to give 24 mg (yield 15%) of the captioned compound as a pale yellow oil.

IR(neat,cm$^{-1}$): 2230,1584,1491,1257,1158,1059,963.

$^1$H-NMR(300 MHz,CDCl$_3$,δ ppm):1.04(3H,t,J=7.1 Hz),2.58(2H,q, J=7.1 Hz),2.73(2H,t,J=5.7 Hz),3.27(2H,d,J=5.4 Hz),3.65 (2H,t,J=5.7 Hz),3.66(3H,s),3.83(2H,t,J=4.8 Hz),4.17(2H, t,J=4.8 Hz),5.79(1H,d,J=15.9 Hz),6.45(1H,dt,J=15.9 Hz, 5.4 Hz),6.85(1H,ddd,J=8.1 Hz,2.4 Hz,1.7 Hz),7.17(1H,ddd,J=8.1 Hz,2.4 Hz,1.7 Hz),7.19–7.21(1H,m),7.30(1H,t,J=8.1 Hz), 7.37(1H,d,J=1.8 Hz),7.38(1H,d,J=2.7 Hz),7.43(1H,dd,J=2.7 Hz,1.8 Hz).

EXAMPLE 57

Production of
(E)-N-ethyl-N-(6,7,7,7-tetrafluoro-6-trifluoromethyl-2-hepten-4-ynyl)-2-[2-3-(3-thienyl)phenoxy]ethoxy]ethylamine 150 mg of (E)-N-ethyl-N-(7,7,7-trifluoro-6-trifluoromethyl-6-hydroxy-2-hepten-4-ynyl)-2-[2-[3-(3thienyl)phenoxy]ethoxy]ethylamine was dissolved in 3 ml of methylene chloride, and under a nitrogen atmosphere, 29 μl of dimethylaminosulfur trifluoride was added at −78° C. The mixture was gradually warmed to room temperature with stirring, and the solution was washed s with water, then dried over anhydrous magnesium sulfate. The desiccant was separated by filtration, and the solvent was evaporated under reduced pressure. The residue was purified by silica gel column chromatography [methylene chloride→methylene chloride/methanol=10/1] to give 113 mg (yield 70%) of the captioned compound as a pale yellow oil.

IR(neat,cm$^{-1}$):
2926,1605,1584,1287,1257,1218,1200,960, 774.

$^1$H-NMR(300 MHz,CDCl$_3$,δ ppm):1.02(3H,t,J=7.1 Hz),2.59(2H,q, J=7.1 Hz),2.71(2H,t,J=6.0 Hz),3.23(2H,dd,J=6.9 Hz,1.5 Hz), 3.69(2H,t,J=6.0 Hz),3.78(2H,t,J=6.2 Hz),4.14(2H,d,J=6.2 Hz),5.65(1H,dt,J=16.2 Hz,1.5 Hz),6.52(1H,dt,J=16.2 Hz, 6.9 Hz),6.83(1H,ddd,J=7.5 Hz,2.7 Hz,1.5 Hz),7.13(1H,dd,J=2.7 Hz,1.8 Hz),7.19(1H,ddd,J=7.5 Hz,1.8 Hz,1.5 Hz),7.30(1H, t,J=7.5 Hz),7.35(1H,dd,J=5.1 Hz,1.5 Hz),7.37(1H,dd,J=5.1 Hz,2.7 Hz),7.43(1H,dd,J=2.7 Hz,1.5 Hz).

EXAMPLE 58

Production of
N-ethyl-N-(6-methoxy-6-methyl-2,4-heptadiynyl)-2-2-3-(3-thienyl)phenoxy]ethoxy]ethylamine 180 mg of N-ethyl-N-propargyl-2-[2-[3-(3-thienyl)-phenoxy]ethoxy]ethylamine [synthesized by reacting N-ethyl-2-[2-[3-(3-thienyl)phenoxy]ethoxy] ethylamine with propargyl bromide], 5.4 mg of copper(I) chloride and 57 mg of hydroxylamine hydrochloride were dissolved in a mixture of 0.8 ml of a 70% aqueous ethylamine solution and 1 ml of methanol. Under ice cooling, 1.5 g of 1-bromo-4-methoxy-4-methyl-1-butyne was added dropwise over 10 minutes, and the mixture was stirred overnight at room temperature. The solvent was evaporated under reduced pressure, and ethyl acetate and water were added to the residue to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by silica gel column chromatography [hexane/ethyl acetate=10/1→5/1→3/1] to give 86.0 mg (yield 37%) of the captioned compound as a colorless oil.

IR(neat,cm$^{-1}$):
2980,2938,1605,1452,1269,1131,1074,771.

$^1$H-NMR(300 MHz,CDCl$_3$,δ ppm):1.07(3H,t,J=7.0 Hz),1.46(6H, s),2.61(2H,q,J=7.0 Hz),2.77(2H,t,J=5.8 Hz),3.35(3H,s), 3.58(2H,s),3.68(2H,t,J=5.8 Hz),3.85(2H,t,J=5.0 Hz),4.18 (2H,t,J=5.0 Hz),6.85(1H,ddd,J=8.0 Hz,2.3 Hz,0.9 Hz),7.14–7.22(2H,m),7.30(1H,t,J=8.0 Hz),7.37(2H,d,J=2.2 Hz),7.44 (1H,t,J=2.2 Hz).

Compound of Example 59 was obtained by performing the same reaction as in Example 58 except that (E)-N-ethyl-N-propargyl-5-[3-(3-thienyl)-2-propenyloxy methyl]-2-furylmethylamine was used instead of the starting compound, N-ethyl-N-propargyl-2-[2-[3-(3-thienyl)phenoxy]ethoxy]ethylamine, which was used in the above-mentioned reaction.

EXAMPLE 59

(E)-N-(6-methoxy-6-methyl-2,4-heptadiynyl)-5-[3-(3-thienyl)-2-propenyloxymethyl]-2-furylmethylamine IR(neat,cm$^{-1}$): 2986,1461,1362,1266,1173,1074,969.

$^1$H-NMR(300 MHz,CDCl$_3$,δ ppm):1.11(3H,t,J=7.0 Hz),1.47(6H, s),2.61(2H,q,J=7.0 Hz),3.37(3H,s),3.47(2H,s),3.67(2H, s),4.15(2H,dd,J=6.3 Hz,1.6 Hz),4.46(2H,s),6.14(H,dt,J=15.9 Hz,6.3 Hz),6.22(1H,d,J=3.0 Hz),6.27(1H,d,J=3.0 Hz), 6.62(1H,d,J=15.9 Hz),7.14–7.17(1H,m),7.-19–7.22(1H,m), 7.24–7.28(1H,m).

EXAMPLE 60

Production of
(E)-N-ethyl-N-(6,6-dimethyl-2-hepten-4-ynyl)-5-[3-(3-thienyl)phenoxy]-3-oxopentylamine 0.82 g of 1,5-dihydroxy-3,3-dimethoxypentane was dissolved in 30 ml of ethyl acetate, and 0.47 ml of methanesulfonyl chloride and 0.8 ml of triethylamine were added. The mixture was stirred under ice cooling for 1 hour, and then the solution was washed successively with a saturated aqueous solution of sodium bicarbonate and water, followed by dried over anhydrous magnesium sulfate. The desiccant was separated by filtration, and the solvent was then evaporated under reduced pressure. The residue was dissolved in 10 ml of dimethylformamide, and 1.5 g of (E)-N-ethyl-6,6-dimethyl-2-hepten-4-ynylamine hydrochloride, 1.1 g of potassium carbonate and 0.1 g of potassium iodide were added. The mixture was heated at 70° C. for 5 hours, and the solvent was evaporated under reduce pressure. The residue was worked up in a customary manner, and then purified by silica gel column chromatography [hexane/ethyl acetate = 10/1 ] to give 0.23 g (yield 14%) of (E)-N-ethyl-N-(6,6-dimethyl-2-hepten-4-ynyl)-5-hydroxy-3,3-dimethoxypentylamine.

0.22 g of the resulting amino alcohol compound was dissolved in 5 ml of ethyl acetate, and 60 μl of methanesulfonyl chloride and 0.1 ml of triethylamine were added. The mixture was stirred at room temperature for 30 minutes, and then the solution was washed successively with a saturated aqueous solution of sodium bicarbonate and water, followed by drying over anhydrous magnesium sulfate. The desiccant was separated by filtration, and the solvent was evaporated under reduced pressure. The residue was added to 1 ml of a dimethylformamide solution of phenolate prepared from 0.13 g of 3-(3-thienyl)phenol and 30 mg of 60% oily sodium hydride. The mixture was heated at 70° C. for 3 hours, and then the solvent was evaporated under reduced pressure. The residue was worked up in a customary manner, and purified by silica gel column chromatography [hexane/ethyl acetate = 5/1 ] to give 42 mg (yield 13%) of (E)-N-ethyl-N-(6,6-dimethyl-2-hepten-4-ynyl)-3,3-dimethoxy-5-[3-(3-thienyl)phenoxy]pentylamine. 30 mg of the resulting ether compound was dissolved in 5 ml of ethyl acetate, and 5 ml of 1 N hydrochloric acid was added. The mixture was stirred at room temperature for 4 hours. The organic layer was separated, washed with water, and worked up in a customary manner. The product was purified by silica gel column chromatography [hexane/ethyl acetate = 10/1] to give 25 mg (yield 88%) of the captioned compound as a colorless oil.

IR(neat,cm$^{-1}$): 2967,2801,1720,1601,1583,1491,1189.

$^1$H-NMR(300 MHz,CDCl$_3$,δ ppm):1.01(3H,t,J = 7.2 Hz),1.23(9H, s),2.41(2H,t,J = 6.4 Hz),2.44(2H,t,J = 6.1 Hz),2.57(2H,q,J = 7.2 Hz),3.18(2H,dd,J = 6.5 Hz,1.4 Hz),3.81(2H,t,J = 6.4 Hz), 4.07(2H,t,J = 6.1 Hz),5.67(1H,dt,J = 15.9 Hz,1.4 Hz),6.07(1H, dt,J = 15.9 Hz,6.5 Hz),6.85(1H,ddd,J = 7.8 Hz,2.8 Hz,1.4 Hz), 7.15–7.21(2H,m),7.29(1H,t,J = 7.8 Hz),7.37(2H,d,J = 2.2 Hz), 7.45(1H,t,J = 2.2 Hz).

EXAMPLE 61

Production of (E,E)-N-methyl-N-(6,6-dimethyl-2-hepten-4-ynyl)-2-3-[3-(3-thienyl)phenyl]-2-propenylthio]ethylamine 300 mg of (E)-2-[3-[3-(3-thienyl)phenyl]-2-propenylthio]ethylamine [synthesized by condensing 3-ethanethiol in the presence of base ]and 170 mg of (E)-6,6-dimethyl-2-hepten-4-ynal were dissolved in a mixture of 10 ml of ethanol and 5 ml of tetrahydrofuran. The mixture was then allowed to stand for 1 hour, and the solvent was evaporated under reduced pressure. The residue was dissolved in 10 ml of ethanol, and the solvent was evaporated again under reduced pressure. The residue was dissolved in 10 ml of ethanol, and 50 mg of sodium borohydride was added, then the mixture was stirred at room temperature for 1 hour. The solvent was evaporated, and ethyl ether and water were added to the residue to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by medium-pressure liquid chromatography [silica gel column, methylene chloride→methylene chloride/methanol = 10/1] to give 147 mg (yield 34%) of (E,E)-N-(6,6-dimethyl-2-hepten-4-ynyl)-2-[3-(3-thienyl)phenyl]-2-propenylthio]ethylamine.

50 mg of the resulting amine compound was dissolved in 2 ml of ethanol, and 50 μl of 35% aqueous HCHO and 20 mg of NaBH$_3$CN were added. The mixture was stirred at room temperature for 2 hours, and then the solvent was evaporated under reduced pressure. The residue was worked up in a customary manner, and purified by medium-pressure liquid chromatography [silica gel column, methylene chloride→methylene chloride/ethyl acetate = 5/1 ] to give 41 mg (yield 79%) of the captioned compound as a colorless oil.

IR(neat,cm$^{-1}$):2968,2866,1605,1458,1365,1263,1206,1125, 963,849,774,690,651.

$^1$H-NMR(300 MHz,CDCl$_3$,δ ppm):1.23(9H,s),2.67(2H,t,J = 6.5 Hz),2.81(2H,t,J = 6.5 Hz),3.28(2H,dd,J = 6.4 Hz,1.5 Hz),3.32 (2H,d,J = 7.3 Hz),5.63(1H,dt,J = 15.9 Hz,11.5 Hz),6.06(1H,dt, J = 15.9 Hz,6.4 Hz),6.23(1H,dt,J = 15.6 Hz,7.3 Hz),6.48(1H,d, J = 15.6 Hz),7.29–7.37(2H,m),7.38–7.40(2H,m),7.-45–7.49 (2H,m),7.58(1H,t,J = 2.0 Hz).

EXAMPLE 62

Production of (E,E)-N-ethyl-N-(6,6-dimethyl-2-hepten-4-ynyl)-3-[4-(3-thienyl)-3-butenyloxy]benzylamine 14 mg of (E)-4-(3-thienyl)-3-butenyl-1-ol was dissolved in 2 ml of methylene chloride, and 14 μl of methanesulfonyl chloride and 22 μl of triethylamine were added. The mixture was stirred at room temperature for 3 hours. The precipitate was removed by filtration, and the solvent was evaporated under reduced pressure to give crude (E)-4-(3-thienyl)-3-butenyl methanesulfonate. 21 mg of (E)-N-ethyl-N-(6,6-dimethyl-2-hepten-4-ynyl)-3-hydroxybenzylamine was dissolved in 2 ml of dimethylformamide, and 3 mg of 60% oily sodium hydride was added. The mixture was stirred for 30 minutes, and a dimethylformamide solution (1 ml) of the mesylated compound obtained above was added, then the mixture was stirred overnight at room temperature. The solvent was evaporated under reduce pressure, and ethyl acetate and water were added to the residue to extract it. The organic layer was separated, washed with a saturated aqueous solution of sodium chloride, and dried over s anhydrous magnesium sulfate. The desiccant was separated by filtration, and the solvent was evaporated under reduced pressure. The residue was purified by medium-pressure liquid chromatography [silica gel column, hexane/ethyl acetate = 4/1 ] to give 2.7 mg (yield 12%) of the captioned compound as a pale yellow oil.

IR(neat,cm$^{-1}$): 2972,2928,1602,1458,1266,1044,964.

$^1$H-NMR(300 MHz,CDCl$_3$,δ ppm):1.05(3H,t,J = 7.1 Hz),1.24(9H, s),2.51(2H,q,J = 7.1 Hz),2.68(2H,dq,J = 6.6 Hz,1.3 Hz),3.10 (2H,dd,J = 6.5 Hz,1.5 Hz),3.58(2H,s),4.06(2H,t,J = 6.6 Hz), 5.65(1H,dt,J = 15.8 Hz,1.5 Hz),6.02–6.21(2H,m),6.54(1H,d, J = 15.9

Hz),6.78(1H,dd,J=7.2 Hz,2.4 Hz),6.88–6.95(2H,m), 7.12(1H,t,J=1.6 Hz),7.18–7.30(3H,m).

Compounds of Examples 63 and 64 were obtained by performing the same reaction as in Example 62 except that 2-(3-thienymethoxy)ethanol or (E)-N-methyl-N-(6,6-dimethyl-2-hepten-4-ynyl)-3-hydroxybenzylamine was used instead of the starting compound, (E)-4-(3-thienyl)-3-buten-1-ol or (E)-N-ethyl-N-(6,6-dimethyl-2-hepten-4-ynyl)-3-hydroxybenzylamine, which was used in the above-mentioned reaction.

EXAMPLE 63

(E,E]-N-methyl-N-(6,6-dimethyl-2-hepten-4-ynyl)-3-[4-(3-thienyl)- 3-butenyloxy]benzylamine IR(neat,cm$^{-1}$):
2968,2866,2788,1602,1584,1491,1455,1365, 1266,1041,765.
$^1$H-NMR(300 MHz,CDCl$_3$,δ ppm):1.24(9H,s),2.18(3H,s),2.66 (2H,dq,J=6.7 Hz,1.4 Hz),3.03(2H,dd,J=6.7 Hz,1.4 Hz),3.45 (2H,s),4.07(2H,t,J=6.7 Hz),5.64(1H,dt,J=15.8 Hz,1.4 Hz), 6.09(1H,dt,J=15.8 Hz,6.7 Hz),6.14(1H,dt,J=15.8 Hz,6.7 Hz), 6.53(1H,dt,J=15.8 Hz,1.4 Hz),6.79(1H,dd,J=7.5 Hz,1.8 Hz), 6.87–6.91(2H,m),7.09(1H,d,J=2.7 Hz),7.18–7.22(2H,m), 7.23–7.27(1H,m).

EXAMPLE 64

(E)-N-ethyl-N-(6,6-dimethyl-2-hepten-4-ynyl)-3-2-(3-thienylmethoxy)ethoxy]benzylamine IR(neat,cm$^{-1}$): 2968,2926,2866,2800,1455,1266,1107.
$^1$H-NMR(300 MHz,CDCl$_3$,δ ppm):1.03(3H,t,J=7.1 Hz),1.24(9H, s),2.49(2H,q,J=7.1 Hz),3.08(2H,d,J=6.5 Hz),3.52(2H,s), 3.82(2H,t,J=4.9 Hz),4.14(2H,t,J=4.9 Hz),4.64(2H,s),5.64 (1H,d,J=15.9 Hz),6.07(1H,dt,J=15.9 Hz,6.5 Hz),6.79(1H,dd, J=7.8 Hz,2.3 Hz),6.90(1H,d,J=7.8 Hz),6.94(1H,br.s),7.10 (1H,dd,J=4.9 Hz,1.2 Hz),7.19(1H,t,J=7.8 Hz),7.23–7.26(1H, m),7.30(1H,dd,J=4.9 Hz,2.9 Hz).

EXAMPLE 65

Production of (E,E)-N-ethyl-N-(6,6-dimethyl-2-hepten-4-ynyl)-3-[3-(3-thienyl)-2-propenylthiomethyl]benzylamine 16 mg of S-[(E)-3-(3-thienyl)-2-propenyl]thioacetate was dissolved in 1 ml of methanol, and 15 mg of (E)-N-ethyl-N-(6,6-dimethyl-2-hepten-4-ynyl)-3-chloromethylbenzylamine and 42 mg of potassium carbonate were added. The mixture was stirred at room temperature for 3 hours. The solvent was evaporated under reduced pressure, and ethyl acetate and water were added to the residue to extract it. The organic layer was separated, washed with a saturated aqueous solution of sodium chloride, and dried over anhydrous magnesium sulfate. The desiccant was separated by filtration and the solvent was evaporated under reduced pressure. The residue was purified by medium-pressure liquid chromatography [silica gel column, hexane/ethyl acetate=5/1] to give 21 mg (yield 97%) of the captioned compound as a colorless oil.

IR(neat,cm$^{-1}$):
2968,2800,1458,1365,1266,1083,963,771.
$^1$H-NMR(300 MHz,CDCl$_3$,δ ppm):1.04(3H,t,J=7.1 Hz),1.23(9H, s),2.50(2H,q,J=7.1 Hz),3.09(2H,dd,J=6.3 Hz,1.4 Hz),3.17 (2H,dd,J=7.3 Hz,1.3 Hz),3.53(2H,s),3.68(2H,s),5.64(1H, dt,J=15.9 Hz,1.4 Hz),6.01(1H,dt,J=15.6 Hz,7.3 Hz), 6.07(1H, dt,J=15.9 Hz,6.3 Hz),6.42(1H,d,J=15.6 Hz),7.13(1H,dd,J=2.5 Hz,1.3 Hz),7.17–7.28(6H,m).

Compound of Example 66 was obtained by performing the same reaction as in Example 65 except that (E)-3-(3-thienyl)-2-propenylamine [see Chem. Lett., 1733(1984)] was used instead of the starting compound, S-[(E)-3-(3-thienyl)-2-propenyl] thio-acetate.

EXAMPLE 66

(E,E)-N-ethyl-N-(6,6-dimethyl-2-hepten-4-ynyl)-3-[3(3-thienyl)- 2-propenylaminomethyl]benzylamine IR(neat,cm$^{-1}$): 2968,2932,2806,1458,1365,966,768.
$^1$H-NMR(300 MHz,CDCl$_3$,δ ppm):1.07(3H,t,J=7.2 Hz),1.24(9H, s),2.55(2H,q,J=7.2 Hz),2.60(1H,br.s),3.13(2H,dd,J=6.7 Hz,1.5 Hz),3.44(2H,d,J=5.7 Hz),3.60(2H,s),3.88(2H,s), 5.65(1H,dt,J=16.0 Hz,1.5 Hz),6.08(1H,dt,J=16.0 Hz,6.7 Hz), 6.18(1H,dt,J=15.6 Hz,5.7 Hz),6.57(1H,d,J=15.6 Hz),7.14 (1H,dd,J=2.6 Hz,1.1Hz),7.20–7.27(3H,m),7.28(2H,d,J=1.1 Hz),7.35(1H,br.s).

EXAMPLE 67

Production of (E)-ethyl-N-(6,6-dimethyl-2-hepten-4-ynyl)-3-[3-(3-thienyloxy)propoxy]benzylamine 49 mg of 3-(3-thienyloxy)propanol [synthesized by heating 1,3-propandiol and 3-bromothiophene in the s presence of sodium, copper(I) iodide and copper(I) oxide at 150° C. for 20 hours] was dissolved in 1 ml of ethyl acetate, and 26 μl of methanesulfonyl chloride and 65 μl of triethylamine were added. The mixture was stirred at room temperature for 30 minutes, and the precipitate was removed by filtration, then the solvent was evaporated under reduced pressure. The residue was added to a dimethylformamide solution (0.5 ml) of phenolate prepared from 80 mg of N-ethyl-N-(6,6-dimethyl-2-hepten-4-ynyl)-3-hydroxybenzylamine and 11.8 mg of 60% oily sodium hydride, and the mixture was stirred in the presence of 48 mg of potassium iodide at room temperature for 20 hours. Ethyl ether and water were added to the reaction solution and the organic layer was collected, washed with a saturated aqueous solution of sodium chloride, then dried over anhydrous magnesium sulfate. The desiccant was separated by filtration, and the solvent was evaporated under reduced pressure. The residue was purified by medium-pressure liquid chromatography [silica gel column, hexane/ethyl acetate=20/1→15/1] to give 97 mg (yield 76%) of the captioned compound as a colorless oil.

IR(neat,cm$^{-1}$):
2968,1548,1458,1377,1263,1236,1179,1155, 1062,753.
$^1$H-NMR(300 MHz,CDCl$_3$,δ ppm):1.03(3H,t,J=7.1 Hz),1.24(9H, s),2.25(2H,q,J=6.2 Hz),2.45(2H,q,J=7.1 Hz),3.09(2H,dd,J=6.3 Hz,1.6 Hz),3.52(2H,s),4.14(2H,t,J=6.2 Hz),4.15(2H,t, J=6.2 Hz),5.64(1H,dt,J=15.9 Hz,1.6 Hz),6.07(1H,dt,J=15.9 Hz,6.3 Hz),6.27(1H,dd,J=3.1 Hz,1.7 Hz),6.76(1H,dd,J=5.1 Hz,1.7 Hz),6.74–6.78(1H,m),6.88–6.91(2H,m),7.17(1H,dd, J=5.1 Hz,3.1 Hz),7.19(1H,t,J=7.8 Hz).

EXAMPLE 68

Production of (E)-3-(3-thienyl)-2-propenyl (E)-3-(N-ethyl-6,6-dimethyl-2-hepten-4-ynylaminomethyl)benzoate 100 mg of methyl (E)-3-(N-ethyl-6,6-dimethyl-2-hepten-4-ynylaminomethyl)benzoate was dissolved in 5 ml of methanol, and 20 ml of 1N hydrochloric acid was added. The mixture was refluxed for 3 hours, and the solvent was evaporated under reduced pressure. The residual carboxylic acid was dissolved in 5 ml of chloroform, and to this solution, a drop of dimethylformamide and 2 ml of thionyl chloride were added. The mixture was then refluxed for 10 minutes, and the solvent was evaporated under reduced pressure. The residual acid chloride was dissolved in 5 ml of dioxane, and 224 mg of (E)-3-(3-thienyl)-2-propen-1-ol and 1.1 g of potassium carbonate were added. The mixture was then stirred overnight at room temperature. The solvent was evaporated under reduced pressure, and ethyl acetate and water were added to the residue to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by medium-pressure liquid chromatography [silica gel column, hexane/ethyl acetate 7/1→5/1] to give 290 mg (yield 43%) of the captioned compound as a colorless oil.

IR(neat,cm$^{-1}$):
2968,1725,1458,1365,1275,1194,1107,966, 747.

$^1$H-NMR(300 MHz,CDCl$_3$,δ ppm):1.04(3H,t,J=7.1 Hz),1.23(9H, s),2.49(2H,q,J=7.1 Hz),3.09(2H,dd,J=6.3 Hz,1.4 Hz),3.60 (2H,s),4.94(2H,dd,J=6.3 Hz,1.6 Hz),5.65(1H,dt,J=15.9 Hz, 1.4 Hz),6.07(1H,dt,J=15.9 Hz,6.3 Hz),6.26(1H,dt,J=15.4 Hz, 6.3 Hz),6.75(1H,d,J=15.4 Hz),7.21–7.29(3H,m),7.38(1H,t,J=7.5 Hz),7.56(1H,d,J=7.5 Hz),7.94(1H,dt,J=7.5 Hz,1.3 Hz), 7.80–7.98(1H,m).

EXAMPLE 69

Production of (E,E)-N-methyl-N-(6,6-dimethyl-2-hepten-4-ynyl)-3-[4-(1-imidazolyl)-2-butenyloxy]benzylamine 50 mg of (E,E)-N-methyl-N-(6,6-dimethyl-2-hepten-4-ynyl)-3-(4-chloro-2-butenyloxy)benzylamine was dissolved in 0.5 ml of dimethylformamide, and 30 mg of imidazole was added. The mixture was heated at 80° C. for 1 hour. The solvent was evaporated under reduced pressure, and ethyl acetate and water were added to the residue to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by silica gel column chromatography [ethyl acetate→ethyl acetate/methanol=10/1] to give 27 mg (yield 53 %) of the captioned compound as a pale yellow oil.

IR(neat,cm$^{-1}$): 2968, 2788, 1587, 1509, 1491, 1455, 1365, 1230, 1026, 969.

$^1$H-NMR(300 MHz, CDCl$_3$, δppm):1.24(9H,s),2.18(3H,s),3.03 (2H,dd,J=6.5 Hz,1.5 Hz),3.45(2H,s),4.53–4.55(2H,m),4.58–4.61(2H,m)5.65(1H,dt,J=15.8 Hz,1.5 Hz),5.81–5.89(1H,m), 5.90–6.12(2H,m),6.77(1H,ddd,J=8.2 Hz,2.5 Hz,1.1 Hz),6.88–6.92(3H,m),7.08(1H,t,J=1.0 Hz),7.21(1H,t,J=8.2 Hz),7.49 (1H,s).

EXAMPLE 70

Production of (E,E)-N'-ethyl-N'-(6,6-dimethyl-2-hepten-4-ynyl)-N-[β-[4-(3-thienyl)-2-thienyl]acryloyl]ethylenediamine 100 mg of (E)-β-[4-(3-thienyl)-2-thienyl]acrylic acid was suspended in 2 ml of chloroform, and 0.6 ml of thionyl chloride was added. The mixture was refluxed for 10 minutes, and the solvent was evaporated under reduced pressure. The residual acid chloride was dissolved in 0.6 ml of dioxane, and a dioxane solution (1 ml) of 30 mg of (E)-N-ethyl-N-(6,6-dimethyl-2-hepten-4-ynyl)ethylenediamine and 23.1 mg of potassium carbonate were added. The mixture was then stirred overnight at room temperature. The solvent was s evaporated under reduced pressure, and ethyl acetate and water were added to the residue to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by silica gel column chromatography [methylene chloride→methylene chloride/methanol=50/1] to give 36 mg (yield 59%) of the captioned compound as a pale yellow powder, m.p. 97°–100° C.

IR(KBr,cm$^{-1}$): 2968, 1653, 1623, 1206, 966, 750.

$^1$H-NMR(300 MHz, CDCl$_3$, δppm):1.04(3H,t,J=7.1 Hz),1.24(9H, s),1.72(1H,br.s),2.57(2H,q,J=7.1 Hz),2.61(2H,t,J=5.9 Hz),3.15(2H,dd,J=6.5 Hz,1.5 Hz),3.43(2H,dt,J=5.9 Hz,5.5 Hz),5.64(1H,dt,J=15.9 Hz,1.5 Hz),6.03(1H,dt,J=15.9 Hz, 6.5 Hz),6.24(1H,d,J=15.4 Hz),7.30(1H,dd,J=4.9 Hz,1.5 Hz), 7.30–7.35(1H,m),7.36(1H,dd,J=4.9 Hz,2.9 Hz),7.38(1H,dd, J=2.9 Hz,1.5 Hz),7.40–7.44(1H,m),7.74(1H,d,J=15.4 Hz).

Compounds of Examples 70 to 74 were obtained by performing the same reaction as in Example 70 except that the corresponding carboxylic acids were used instead of the starting compound, (E)-β-[4-(3-thienyl)-2-thienyl]acrylic acid, which was used in the above-mentioned reaction.

EXAMPLE 71

(E,E)-N'-ethyl-N'-(6,6-dimethyl-2-hepten-4-ynyl)-N-[3-(3-thienyl)cinnamoyl]ethylenediamine IR(neat,cm$^{-1}$): 3292, 2974, 2872, 1662, 1626, 1554, 1365, 1263, 777.

$^1$H-NMR(300 MHz, CDCl$_3$, δppm):1.04(3H,t,J=7.1 Hz),1.23(9H, s),2.57(2H,q,J=7.1 Hz),2.63(2H,t,J=5.9 Hz),3.19(2H,dd,J=6.6 Hz,1.5 Hz),3.44(2H,q,J=5.9 Hz),5.65(1H,dt,J=15.7 Hz, 1.5 Hz),6.04(1H,dt,J=15.7 Hz,6.6 Hz),6.20–6.30(1H,br.s), 6.46(1H,d,J=15.6 Hz),7.40(1H,t,J=7.5 Hz),7.40–7.42(2H, m),7.46(1H,dt,J=7.6 Hz,1.6 Hz),7.48(1H,dd,J=2.4 Hz,1.6 Hz),7.57(1H,dt,J=7.6 Hz,1.6 Hz),7.66(1H,d,J=15.6 Hz), 7.73(1H,t,J=1.6 Hz).

EXAMPLE 72

(E)-N'-ethyl-N'-(6,6-dimethyl-2-hepten-4-ynyl)-N-3-(3-thienyl)phenoxyacetyl]ethylenediamine IR(neat,cm$^{-1}$): 2972, 1682, 1534, 1442, 1288, 1272, 1184, 1066, 774.

¹H-NMR(300 MHz, CDCl₃, δppm):0.97(3H,t,J=7.1 Hz),1.21(9H, s),2.50(2H,q,J=7.1 Hz),2.58(2H,t,J=6.1 Hz),3.09(2H,dd,J=6.3 Hz,1.5 Hz),3.38(2B,q,J=6.1 Hz),4.45(2H,s),5.65(1H,dt, J=15.9 Hz,1.5 Hz),5.95(1H,dt,J=15.9 Hz,6.3 Hz),6.87(1H, ddd,J=8.0 Hz,2.3 Hz,1.0 Hz),7.15(1H,dd,J=2.3 Hz,1.8 Hz), 7.19-7.22(1H,br.s),7.25(1H,dt,J=8.0 Hz,1.0 Hz),7.34(1H, t,J=8.0 Hz),7.35-7.40(2H,m),7.45(1H,dd,J=2.7 Hz,1.2 Hz).

EXAMPLE 73

(E)-N'-ethyl-N'-(6,6-dimethyl-2-hepten-4-ynyl)-N-[3-(3-thienyl)phenylthioacetyl]ethylenediamine IR(neat,cm⁻¹): 3300, 2974, 1662, 1518, 1269, 774.
¹H-NMR(300 MHz, CDCl₃, δppm):0.88(3H,t,J=7.1 Hz),1.23(9H, s),2.40-2.60(4H,m),3.00(2H,d,J=5.7 Hz),3.20-3.35(2H,m), 3.69(2H,s),5.57(1H,d,J=15.8 Hz),5.90(1H,dt,J=15.8 Hz, 5.7 Hz),7.23(1H,ddd,J=7.8 Hz,1.4 Hz,1.2 Hz),7.30-7.46(5H, m),7.52-7.54(1H,m).

EXAMPLE 74

(E)-N'-ethyl-N'-(6,6-dimethyl-2-hepten-4-ynyl)-N-[3-(3-thienyl)phenylaminoacetyl]ethylenediamine IR(neat,cm⁻¹): 3346, 2968, 1665, 1608, 1533.
¹H-NMR(300 MHz, CDCl₃, δppm):0.86(3H,t,J=7.0 Hz),1.24(9H, s),2.45(2H,q,J=7.0 Hz),2.53(2H,t,J=5.9 Hz),3.04(2H,d,J=6.1 Hz),3.31-3.37(2H,m),3.86(2H,d,J=3.7 Hz),4.35(1H, br.s),5.57(1H,d,J=15.5 Hz),5.88(1H,dt,J=15.5 Hz,6.1 Hz), 6.57(1H,ddd,J=8.5 Hz,2.0 Hz,1.2 Hz),6.84(1H,t,J=2.0 Hz), 7.02(1H,dt,J=8.5 Hz,2.0 Hz),7.23(1H,t,J=8.5 Hz),7.35(1H, d,J=1.2 Hz),7.35(1H,d,J=2.3 Hz),7.41(1H,dd,J=2.3 Hz,1.2 Hz).

EXAMPLE 75

Production of
(E,E)-N-[3-[3-(3-thienyl)phenyl]-2-propenyl]-(N'-ethyl-6,6-dimethyl-2-hepten-4-ynylamino)acetamide 100 mg of (E)-N-ethyl-N-(6,6-dimethyl-2-hepten-4-ynyl)glycine hydrochloride was dissolved in 10 ml of methylene chloride, and 34 μl of methyl chloroformate and 0.1 ml of triethylamine were added under ice cooling. The mixture was stirred for 30 minutes, and a methylene chloride solution(5 ml) of 90 mg of (E)-3-[3-(3-thienyl)phenyl]-2-propenylamine was added, then the mixture was stirred at room temperature for 2 hours. The solvent was evaporated under reduced pressure, and ethyl acetate and water were added to the residue to extract it. The organic layer was separated, washed with a saturated aqueous solution of sodium chloride, and dried over anhydrous magnesium sulfate. The desiccant was separated by filtration and the solvent was evaporated under reduced pressure. The residue was purified by medium-pressure liquid chromatography [silica gel column, hexane→hexane/ethyl acetate=5/1] to give 24 mg (yield 17%) of the captioned compound as a pale yellow oil.

IR(neat,cm⁻¹): 3370, 2974, 2872, 1677, 1605, 1518, 1458, 1365, 1266, 966, 771.
¹H-NMR(300 MHz, CDCl₃, δppm):1.05(3H,t,J=7.0 Hz),1.22(9H, s),2.68(2H,q,J=7.0 Hz),3.11(2H,s),3.15(2H,dd,J=6.6 Hz, 1.6 Hz),4.07-4.12(2H,m),5.64(1H,dt,J=15.9 Hz,1.6 Hz), 6.00(1H,dt,J=15.9 Hz,6.6 Hz),6.26(1H,dt,J=15.8 Hz,6.6 Hz), 6.57(1H,dt,J=15.8 Hz,1.5 Hz),7.30(1H,dt,J=8.0 Hz,1.8 Hz), 7.35(1H,t,J=8.0 Hz),7.30-7.35(3H,m),7.46(1H,dt,J=8.0 Hz, 1.8 Hz),7.58(1H,t,J=1.8 Hz).

EXAMPLE 76

Production of
(E,E)-N'-ethyl-N'-(6,6-dimethyl-2-hepten-4-ynyl)-N-[3-[3-(3-thienyl)phenyl]-2-propenyl]ethylenediamine 30 mg of (E)-3-(3-thienyl)cinnamaldehyde and 29 mg of (E)-N-ethyl-N-(6,6-dimethyl-2-hepten-4-ynyl)ethylenediamine were dissolved in 1 ml of methanol, and 30 mg of molecular sieves 3A was added. The mixture was stirred at room temperature for 2 hours, and then the insoluble material was removed by filtration. The solvent was evaporated under reduced pressure, and the residue was suspended in 1 ml of ethanol. To this suspension, 5.3 mg of sodium borohydride was added, and the mixture was stirred at room temperature for 30 minutes. The solvent was evaporated under reduced pressure, and ethyl ether and water were added to the residue to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by medium-pressure liquid chromatography [silica gel column, chloroform/methanol =100/1→40/1] to give 35 mg (yield 63%) of the captioned compound as a pale yellow oil.

IR(neat,cm⁻¹): 2968, 2818, 1458, 1365, 1266, 963, 846, 771.
¹H-NMR(300 MHz, CDCl₃, δppm):1.02(3H,t,J=7.1 Hz),1.23(9H, s),2.53(2H,q,J=7.1 Hz),2.59(2H,t,J=5.7 Hz),2.72(2H,t,J=5.7 Hz),3.12(2H,dd,J=6.6 Hz,1.5 Hz),3.44(2H,dd,J=6.3 Hz, 1.1 Hz),5.63(1H,dt,J=15.9 Hz,1.5 Hz),6.05(1H,dt,J=15.9 Hz, 6.6 Hz),6.36(1H,dt,J=15.9 Hz,6.3 Hz),6.58(1H,dt,J=15.9 Hz, 1.1 Hz),7.32-7.37(2H,m),7.39-7.41(2H,m),7.-44-7.47(2H, m),7.59-7.61(1H,m).

Compounds of Examples 77 to 79 were obtained by performing the same reaction as in Example 76 except that the corresponding aldehyde or ketone compounds were used instead of the starting compound, (E)-3-(3-thienyl)cinnamaldehyde.

EXAMPLE 77

(E)-N'-ethyl-N'-(6,6-dimethyl-2-hepten-4-ynyl)-N-2-[3-(3-thienyl)phenoxy]ethyl)ethylenediamine IR(neat,cm⁻¹): 3300, 2968, 1602, 1455, 1365, 1284, 756.
¹H-NMR(300 MHz, CDCl₃, δppm):1.03(3H,t,J=7.1 Hz),1.23(9H, s),1.76(1H,br.s),2.55(2H,q,J=7.1 Hz),2.63(2H,t,J=6.0 Hz),2.78(2H,t,J=6.0 Hz),3.06(2H,t,J=5.1 Hz),3.15(2H,dd, J=6.6 Hz,1.5 Hz),5.65(1H,dt,J=15.9 Hz,1.5 Hz),6.05(1H,dt, J=15.9 Hz,6.6 Hz),6.86(1H,ddd,J=8.1 Hz,2.4 Hz,0.9 Hz),7.15 (1H,t,J=2.4 Hz),7.19(1H,ddd,J=7.5 Hz,2.4 Hz,0.9 Hz),7.30 (1H,t,J=8.1 Hz),7.37(2H,d,J=2.2 Hz),7.44(1H,t,J=2.2 Hz).

EXAMPLE 78

(E)-N'-ethyl-N'-(6,6-dimethyl-2-hepten-4-ynyl)-N-3-[3-(3-thienyl)phenyl]propyl]ethylenediamine IR(neat,cm⁻¹): 2968, 2932, 2860, 1458, 774.
¹H-NMR(300 MHz, CDCl₃, δppm): 0.99(3H,t,J=7.1 Hz),1.23(9H, s),2.08(2H quint.,J=7.4 Hz),2.54(2H,q,J=7.1 Hz) 2.68-2.77(4H,m),2.-

83-2.88(4H,m),3.12(2H,dd,J=6.5 Hz,1.5 Hz), 5.61(1H,dt,J=15.9 Hz,1.5 Hz),5.97(1H,dt,J=15.9 Hz,6.5 Hz), 7.15(1H,dd,J=8.0 Hz,1.8 Hz),7.29-7.49(6H,m).

EXAMPLE 79

(E,E)-N'-ethyl-N'-(6,6-dimethyl-2-hepten-4-ynyl)-N-4-[3-(3-thienyl)phenyl]-3-buten-2-yl]ethylenediamine IR(neat,cm$^{-1}$): 2968, 2812, 1461, 1368, 966.

$^1$H-NMR(300 MHz, CDCl$_3$, δppm):1.01(3H,t,J=7.1 Hz),1.23(9H, s),1.27(3H,d,J=6.7 Hz),2.51(2H,q,J=7.1 Hz),2.56-2.78(4H, m),3.11(2H,dd,J=6.7 Hz,1.5 Hz),3.35(1H,quint.,J=6.8 Hz), 5.62(1H,dt,J=15.9 Hz,1.5 Hz),6.04(1H,dt,J=15.9 Hz,6.7 Hz}, 6.14(1H,dd,J=15.7 Hz,7.7 Hz),6.51(1H,d,J=15.7 Hz),7.27-7.36(2H,m),7.37-7.42(2H,m),7.43-7.48(2H,m),7.60(1H, br.s).

EXAMPLE 80

Production of (E,E)-N'-ethyl-N'-(6,6-dimethyl-2-hepten-4-ynyl)-N-methyl-N-[3-[3-(3-thienyl)phenyl]-2-propenyl]ethylenediamine 12 mg of (E,E)-N'-ethyl-N'-(6,6-dimethyl-2-hepten-4-ynyl)-N-[3-[3-(3-thienyl)phenyl]-2-propenyl]ethylenediamine was dissolved in 0.5 ml of ethanol, and 5 μl of 35% formalin was added. The mixture was stirred at room temperature for 5 minutes, and 2 mg of sodium cyanoborohydride was added. The mixture was then stirred for 1 hour, and acidified with 1N hydrochloric acid. The solvent was evaporated under reduced pressure, and chloroform and water were added to the residue to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by medium-pressure liquid chromatography [silica gel column, chloroform/methanol=100/1→50/1→10/1] to give 4.1 mg (yield 34%) of the captioned compound as a pale yellow oil.

IR(neat,cm$^{-1}$): 2974, 2800, 1458, 1365, 1269, 966, 771.

$^1$H-NMR(300 MHz, CDCl$_3$, δppm):1.03(3H,t,J=7.1 Hz),1.23(9H, s),2.30(3H,s),2.52-2.60(6H,m),3.16(2H,d,J=6.7 Hz),3.22 (2H,d,J=6.5 Hz),5.62(1H,dt,J=15.9 Hz,1.5 Hz),6.06(1H,dt, J=15.9 Hz,6.7 Hz),6.33(1H,dt,J=15.9 Hz,6.5 Hz),6.56(1H,d, J=15.9 Hz),7.29-7.37(2H,m),7.39(2H,d,J=1.8 Hz),7.45-7.48(2H,m),7.59-7.60(1H,m).

Compounds of Examples 81 and 82 were obtained by performing the same reaction as in Example 80 except that (E)-N'-ethyl-N'-(6,6-dimethyl-2-hepten-4-ynyl)-N-[2-[3-(3-thienyl)phenoxy]ethyl]ethylenediamine or acetaldehyde was used instead of the starting compound, (E, E)-N'-ethyl-N'-(6,6-dimethyl-2-hepten-4-ynyl)-N-[3-[3-(3-thienyl)phenyl]-2-propenyl]ethylenedi-amine or formalin, which was used in the above-mentioned reaction.

EXAMPLE 81

(E)-N'-ethyl-N'-(6,6-dimethyl-2-hepten-4-ynyl)-N-methyl-N-[2-[3-(3-thienyl)phenoxy]ethyl]ethylenediamine IR(neat,cm$^{-1}$): 2968, 1605, 1455, 1287, 1221, 1038, 771.

$^1$H-NMR(300 MHz, CDCl$_3$, δppm):1.03(3H,t,J=7.1 Hz),1.23(9H, s),2.37(3H,s),2.56(2H,q,J=7.1 Hz),2.61(4H,s),2.86(2H,t, J=5.7 Hz),3.17(2H,dd,J=6.6 Hz,1.2 Hz),4.12(2H,t,J=5.7 Hz), 5.62(1H,dt,J=15.9 Hz,1.2 Hz),6.05(1H,dt,J=15.9 Hz,6.6 Hz), 6.84(1H,ddd,J=8.4 Hz,2.4 Hz,0.9 Hz),7.14(1H,dd,J=2.7 Hz, 2.4 Hz),7.18(1H,ddd,J=7.5 Hz,1.4 Hz,1.0 Hz),7.30(1H,t,J=7.8 Hz),7.37(2H,d,J=2.2 Hz),7.44(1H,t,J=2.2 Hz).

EXAMPLE 82

(E,E)-N,N'-diethyl-N'-(6,6-dimethyl-2-hepten-4-ynyl)-N-[3-[3-(3-thienyl)phenyl]-2-propenyl]ethylenediamine IR(neat,cm$^{-1}$): 2968, 2926, 2866, 2806, 1365, 966, 771.

$^1$H-NMR(300 MHz, CDCl$_3$, δppm):1.02(3H,t,J=7.2 Hz),1.08(3H,t, J=7.2 Hz),1.23(9H,s),2.53(2H,q,J=7.2 Hz),2.60(2H,q,J=7.2 Hz),2.58-2.62(4H,m),3.14(2H,dd,J=6.6 Hz,1.5 Hz).3.30 (2H,d,J=6.6 Hz),5.62(1H,dt,J=15.9 Hz,1.5 Hz),6.05(1H,dt, J=15.9 Hz,6.6 Hz),6.33(1H,dt,J=15.9 Hz,6.6 Hz),6.56(1H,d, J=15.9 Hz),7.31-7.39(4H,m),7.-44-7.47(2H,m),7.59(1H, br.s).

EXAMPLE 83

Production of (E,E,E)-N-ethyl-N-(6,6-dimethyl-2-hepten-4-ynyl)-3-5-(3-thienyl)-3-oxo-1,4-pentadienyl]benzylamine 10 mg of (E)-4-(3-thienyl)-3-buten-2-one was dissolved in 1.5 ml of ethanol, and 22 mg of (E)-N-ethyl-N-(6,6-dimethyl-2-hepten-4-ynyl)-3-formylbenzylamine and 4 mg of sodium methoxide were added. The mixture was refluxed for hour, and the solvent was evaporated under reduced pressure, then ethyl acetate and water were added to the residue to extract it. The organic layer was separated, washed with a saturated s aqueous solution of sodium chloride, and dried over anhydrous magnesium sulfate. The solvent was evaporated under reduced pressure, and the residue was purified by medium-pressure liquid chromatography [silica gel column, hexane/ethyl acetate=3/1→methylene chloride/methanol=70/1] to give 13 mg (yield 42%) of the captioned compound as a pale yellow oil.

IR(neat,cm$^{-1}$): 2968, 1656, 1623, 1458, 1320, 1266, 1185, 1095, 981, 756.

$^1$H-NMR(300 MHz, CDCl$_3$, δppm):1.06(3H,t,J=5.3 Hz),1.24(9H, s),2.50(2H,q,J=5.3 Hz),3.11(2H,dd,J=6.3 Hz,1.5 Hz),3.59 (2H,s),5.65(1H,dt,J=15.9 Hz,1.5 Hz),6.05(1H,dt,J=15.9 Hz, 6.3 Hz),6.95(1H,d,J=15.8 Hz),7.05(1H,d,J=17.2 Hz),7.33 7.42(4H,m),7.49(1H,dd,J=4.2 Hz,1.7 Hz),7.60(2H,s),7.72 (1H,d,J=15.8 Hz),7.74(1H,d,J=17.2 Hz).

EXAMPLE 84

Production of
(E,E)-N-ethyl-N-(6,6-dimethyl-2-hepten-4-ynyl)-6-3-(3-thienyl)phenyl)-4-oxo-5-hexenylamine A 1M tetrahydrofuran solution (0.6 ml) of lithium bis-(trimethylsilyl)amide was added to 1 ml of tetrahydrofuran under an argon atmosphere, and the mixture was cooled to −78° C. To this solution were added, dropwise with stirring, a tetrahydrofuran solution (2 ml) of 125 mg of (E)-N-ethyl-N-(6,6-dimethyl-2-hepten-4-ynyl)-4-oxo-pentylamine, followed by a tetrahydrofuran solution (2 ml) of 94 mg of 3-(3-thienyl)benzaldehyde. The mixture was stirred at −78° C. for 1 hour, and then at 0° C. for 1 hour. The reaction mixture was neutralized with acetic acid, and ethyl acetate and water were added to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by silica gel column chromatography [ethyl acetate→ethyl acetate/methanol=20/1] to give 78 mg (yield 40%) of (E)-N-ethyl-N-(6,6-dimethyl-2-hepten-4-ynyl)-6-hydroxy-4-oxo-6-[3-(3-thienyl)phenyl]hexenylamine.

The resulting alcohol compound (68 mg) was dissolved in 3 ml of methylene chloride, and 40 μl of methanesulfonyl chloride and 0.2 ml of triethylamine were added. The mixture was stirred at room temperature for 5 hours, and the solvent was evaporated. The residue was worked up in a customary manner, and then purified by silica gel column chromatography [hexane/ethyl acetate=1/1] to give 20 mg (yield 30%) of the captioned compound as a pale yellow oil.

IR(neat,cm$^{-1}$): 2974, 1692, 1668, 1611, 1458, 1365, 1266, 1200, 1173, 1095, 1053, 901, 774.

$^1$H-NMR(300 MHz, CDCl$_3$, δppm):1.01(3H,t,J=7.2 Hz),1.23(9H, s),1.83(2H,q,J=7.2 Hz),1.48(2H,t,J=7.2 Hz),2.51(2H,q,J=7.2 Hz),2.72(2H,t,J=7.2 Hz),3.11(2H,dd,J=6.3 Hz,1.5 Hz), 5.64(1H,dt,J=15.9 Hz,1.5 Hz),6.04(1H,dt,J=15.9 Hz,6.3 Hz), 6.79(1H,d,J=16.5 Hz),7.38-7.64(6H,m),7.76(1H,t,J=2.1 Hz).

EXAMPLE 85

Production of
(E)-N-[3-(3-thienyl)benzyl]-4-(N'-ethyl-6,6-dimethyl-2-hepten-4-ynylamino)crotonamide 100 mg of 4-(N-ethyl-6,6-dimethyl-2-hepten-4-ynylamino)crotonic acid [synthesized by condensing ethyl 4-bromocrotonate with N-ethyl-6,6-dimethyl-2-hepten-4-ynylamine in the presence of base, and subsequently hydrolizing it with alkaline]hydrochloride was suspended in 2 ml of chloroform, and 0.1 ml of thionyl chloride was added. The mixture was stirred at 50° C. for 30 minutes, and the solvent was evaporated under reduced pressure, then the residue was dissolved in 15 ml of dioxane. To this solution, 73 mg of 3-(3-thienyl)-benzylamine and 140 mg of potassium carbonate were added, and the mixture was stirred overnight at room temperature. The solvent was evaporated, and ethyl acetate and water were added to the residue to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by medium-pressure liquid chromatography [silica gel column, chloroform→chloroform/methanol=50/1] to give 64 mg (yield 37%) of the captioned compound as a pale yellow oil.

IR(neat,cm$^{-1}$): 3286, 2968, 2926, 1674, 1623, 1548, 1365, 777.

$^1$H-NMR(300 MHz, CDCl$_3$, δppm):1.04(3H,t,J=7.1 Hz),1.23(9H, s),2.50(2H,q,J=7.1 Hz),3.10(2H,dd,J=6.3 Hz,1.4 Hz),3.19 (2H,dd,J=5.7 Hz,1.4 Hz),4.55(2H,d,J=5.9 Hz),5.63(1H,dt,J=15.4 Hz,1.4 Hz),5.79(1H,t,J=5.9 Hz),5.95–6.06(2H,m),6.87 (1H,dt,J=15.3 Hz,5.7 Hz),7.23(1H,dt,J=8.1 Hz,2.4 Hz),7.37 (1H,t,J=8.1 Hz),7.37–7.41(2H,m),7.45(1H,dd,J=3.0 Hz,1.8 Hz),7.49–7.54(2H,m).

EXAMPLE 86

Production of
(E)-N-3-(N'-ethyl-6,6-dimethyl-2-hepten-4-ynylaminomethyl)phenyl]-3-thienylmethoxyacetamide 30 mg of 3-thienylmethoxyacetic acid was dissolved in 1 ml of methylene chloride, and 24 mg of 1-hydroxybenzotriazole and 31 mg of 1-(3-dimethylaminopropyl)-3-ethylcarbodiimide were added. The mixture was stirred at room temperature for 20 minutes and then a methylene chloride solution (1 ml) of 43 mg of (E)-N-ethyl-N-(6,6-dimethyl-2-hepten-4-ynyl)-3-aminobenzylamine was added. The mixture was stirred at room temperature for 2 hours, and then diluted with methylene chloride. The reaction mixture was washed with a saturated aqueous solution of sodium chloride, and dried over anhydrous magnesium sulfate. The desiccant was separated by filtration, and the solvent was evaporated under reduced pressure. The residue was purified by silica gel column chromatography [hexane/ethyl acetate=5/1→2/1] to give 61 mg (yield 90%) of the captioned compound as a colorless oil.

IR(neat,cm$^{-1}$): 3400, 2974, 2932, 2872, 286, 1692, 1614, 1599, 1539, 1494, 1446, 1365, 1341, 1311, 1266, 1227, 1158, 1104, 963, 786, 696.

$^1$H-NMR(300 MHz, CDCl$_3$, δppm):1.04(3H,t,J=7.2 Hz),1.24(9H, s),2.50(2H,q,J=7.2 Hz),3.09(2H,dd,J=6.3 Hz,1.5 Hz),3.54 (2H,s),4.08(2H,s),4.68(2H,s),5.64(1H,dt,J=15.9 Hz,1.5 Hz),6.07(1H,dt,J=15.9 Hz,6.3 Hz),7.09(1H,d.J=7.8 Hz), 7.12(1H,dd,J=5.1 Hz,1.5 Hz),7.20–7.58(5H,m),8.26(1H, br.s).

Compounds of Examples 87 to 89 were obtained by performing the same reaction as in Example 86 except that the corresponding carboxylic acid derivatives and amine derivatives were used instead of the starting compounds, 3-thienylmethoxyacetic acid and (E)-N-ethyl-N-(6,6-dimethyl-2-hepten-4-ynyl)-3-aminobenzylamine, which were used in the above-mentioned reaction.

EXAMPLE 87

(E)-N-2-(3-thienyl)ethyl]-3-(N'-ethyl-6,6-dimethyl-2-hepten-4-ynylaminomethyl)phenylacetamide IR(neat,cm$^{-1}$): 3275, 2950, 1640, 1550, 1440, 1360, 1260, 770.

$^1$H-NMR(300 MHz, CDCl$_3$, δppm):1.03(3H,t,J=7.0 Hz),1.23(9H, s),2.49(2H,q,J=7.0 Hz),2.75(2H,t,J=6.8 Hz),3.07(2H,dd,J=6.3 Hz,1.8 Hz),3.45(2H,q,J=6.8 Hz),3.53(4H,s),5.34–5.42 (1H,m),5.64(1H,dt,J=15.9 Hz,1.4 Hz),6.05(1H,dt,J=15.9 Hz, 6.3 Hz),6.79–7.29(7H,m).

EXAMPLE 88

(E,E)-N-3-(N'-ethyl-6,6-dimethyl-2-hepten-4-ynyl-aminomethyl)benzyl]-β-(3-thienyl)acrylamide IR(neat,cm$^{-1}$): 2974, 1626, 1554, 1281, 786, 756.
$^1$H-NMR(300 MHz, CDCl$_3$, δppm):1.04(3H,t,J=7.0 Hz),1.23(9H, s),2.51(2H,q,J=7.0 Hz),3.10(2H,dd,J=6.3 Hz,1.4 Hz),3.55 (2H,s),4.56(2H,d,J=5.6 Hz),5.64(1H,dt,J=15.4 Hz,1.9 Hz), 5.85-5.92(1H,m),6.06(1H,dt,J=15.9 Hz,6.3 Hz),6.25(1H,d, J=15.7 Hz),7.18-7.33(6H,m),7.43-7.45(1H,m),7.66(1H,d,J=15.2 Hz).

EXAMPLE 89

(E,E)-N-(3-thienylmethyl)-β-3-(N'-ethyl-6,6-dimethyl-2-hepten-4-ynylaminomethyl)cinnamamide IR(neat,cm$^{-1}$): 3280, 2968, 2926, 2866, 2806, 1662, 1626, 1554,
$^1$H-NMR(300 MHz, CDCl$_3$, δppm):1.03(3H,t,J=6.6 Hz),1.23(9H, s),2.50(2H,q,J=6.6 Hz),3.09(2H,dd,J=6.8 Hz,1.9 Hz),3.56 (2H,s),4.59(2H,d,J=5.6 Hz),5.60(1H,dt,J=15.8 Hz,1.9 Hz), 5.86(1H,t,J=5.6 Hz),6.08(1H,dt,J=15.8 Hz,6.8 Hz),6.40(1H, d,J=15.7 Hz),7.08(1H,dd,J=5.3 Hz,1.2 Hz),7.20(1H,m),7.28-7.38(4H,m),7.48(1H,s),7.65(1H,d,J=15.7 Hz).

EXAMPLE 90

Production of (E,E)-N-ethyl-N-(6-methoxy-6-methyl-2-hepten-4-ynyl)-5-3-(3-thienylmethoxy)-1-propenyl]-2-furylmethylamine hydrochloride 123 mg of (E,E)-N-ethyl-N-(6-methoxy-6-methyl-2-hepten-4-)-5-(3-hydroxy-1-propenyl)-2-furylmethylamine and 69 mg of 3-bromomethylthiophene were dissolved in 3 ml of dimethylform-amide, and 16 mg of 60% oily sodium hydride was added under ice cooling. The mixture was stirred at this temperature for 3 hours, and then ethyl ether and water were added. The organic layer was separated, washed with a saturated aqueous solution of sodium chloride, and dried over anhydrous magnesium sulfate. The desiccant was separated by filtration, and the solvent was evaporated under reduced pressure. The residue was purified by silica gel column chromatography [hexane/ethyl acetate=3/1] to give 78 mg (yield 49%) of the captioned free base as a pale yellow oil. The resulting free base was treated by a hydrogen chloride-ethyl ether solution, and recrystallized from a mixture of ethyl acetate and ethyl ether to give the captioned compound (m.p. 100°-102 ° C.) as a colorless crystalline powder.

IR(KBr,cm$^{-1}$): 2608, 1167, 1119, 1074, 966.
$^1$H-NMR(300 MHz, CDCl$_3$, δppm):1.47(6H,s),1.54(3H,t,J=7.2 Hz),2.92-3.16(2H,m),3.35(3H,s),3.62(2H,d,J=7.4 Hz), 4.17(2H,dd,J=1.5 Hz,5.3 Hz),4.24(1H,br.s),4.59(1H,s), 5.91(1H,d,J=15.9 Hz),6.21-6.32(2H,m),6.42-6.55(2H,m), 6.65(1H,d,J=3.5 Hz),7.10(1H,dd,J=5.0 Hz,1.5 Hz),7.23-7.28(1H,m),7.32(1H,dd,J=5.0 Hz,3.0 Hz).

Compounds of Examples 91 to 95 were obtained by performing the same reaction as in Example 90 except that the corresponding alcohol derivatives and/or bromoalkyl derivatives were used instead of the starting s compounds, (E,E)-N-ethyl-N-(6-methoxy-6-methyl-2-hepten-4-)-5-(3-hydroxy-1-propenyl)-2-furylmethylamine and/or 3-bromomethylthiophene, which were used in the above-mentioned reaction.

EXAMPLE 91

(E,E)-N-ethyl-N-(6-methoxy-6-methyl-2-hepten-4-ynyl)-5-[3-(3-thienyl)-2-propenyloxymethyl]-2-oxazolylmethylamine IR(neat,cm$^{-1}$): 2980, 1248, 1173, 1101, 1074, 966.
$^1$H-NMR(300 MHz, CDCl$_3$, δppm):1.09(3H,t,J=7.1 Hz),1.46(6H, s),2.58(2H,q,J=7.1 Hz),3.23(2H,dd,J=6.2 Hz,1.5 Hz),3.35 (3H,s),3.78(2H,s),4.16(2H,dd,J=6.4 Hz,1.5 Hz),4.53(2H, s),5.72(1H,dt,J=15.9 Hz,1.5 Hz),6.08-6.20(2H,m),6.63(1H, d,J=15.9 Hz),6.98(1H,s),7.18(1H,dd,J=2.7 Hz,1.5 Hz),7.21 (1H,dd,J=5.4 Hz,1.5 Hz),7.28(1H,dd,J=5.4 Hz,3.0 Hz)

EXAMPLE 92

(E,E)-N-ethyl-N-(6-methoxy-6-methyl-2-hepten-4-ynyl)-2-[3-(3-thienyl)-2-propenyloxymethyl]-4-thiazolylmethylamine IR(neat,cm$^{-1}$): 2980, 2926, 2824, 1248, 1173, 1149, 1107, 1074, 966.
$^1$H-NMR(300 MHz, CDCl$_3$, δppm):1.09(3H,t,J=7.1 Hz),1.46(6H, s),2.57(2H,q,J=7.1 Hz),3.19(2H,dd,J=6.3 Hz,1.8 Hz),3.35 (3H,s),3.73(2H,s),4.26(2H,dd,J=6.3 Hz,1.5 Hz),4.81(2H, s),5.69(1H,dt,J=15.6 Hz,1.8 Hz),6.16(1H,dt,J=15.9 Hz, 6.3 Hz),6.19(1H,dt,J=15.6 Hz,6.3 Hz),6.66(1H,dt,J=15.9 Hz, 1.5 Hz),7.12(1H,s),7.17(1H,dd,J=3.0 Hz,1.2 Hz),7.22(1H, dd,J=5.4 Hz,1.2 Hz),7.27(1H,dd,J=5.4 Hz,3.0 Hz).

EXAMPLE 93

(E,E)-N-ethyl-N-(6-methoxy-6-methyl-2-hepten-4-ynyl)-3-[3-(3-thienylmethoxy)-1-propenyl]-2-isoxazolylmethylamine IR(neat,cm$^{-1}$): 2980, 1440, 1362, 1248, 1173, 1152, 1113, 1074, 966, 780.
$^1$H-NMR(30 ppm):1.08(3H,t,J=7.1 Hz),1.46(6H, s),2.55(2H,q,J=7.1 Hz),3.17(2H,dd,J=6.3 Hz,1.5 Hz),3.36 (3H,s),3.75(2H,s),4.20(2H,dd,J=5.3 Hz,1.5 Hz),4.59(2H, s),5.72(1H,dt,J=15.9 Hz,1.5 Hz),6.13(1H,dt,J=15.9 Hz, 6.3 Hz),6.24(1H,s),6.40(1H,dt,J=16.1 Hz,5.3 Hz),6.69(1H, dt,J=16.1 Hz,1.5 Hz),7.10(1H,dd,J=4.9 Hz,1.3 Hz),7.21-7.23 (1H,m),7.32(1H,dd,J=4.9 Hz,2.9 Hz).

EXAMPLE 94

(E)-N-ethyl-N-(6,6-dimethyl-2-hepten-4-ynyl)-3-[3-(5-oxazolyl)-2-propenyloxymethyl]benzylamine IR(neat,cm$^{-1}$): 2974, 1365, 1266, 1110, 960.
$^1$H-NMR(300 MHz, CDCl$_3$, δppm):1.01-1.16(3H,m),1.24(9H,s), 2.48-2.65(2H,m),3.05-3.25(2H,m),3.54-3.70(2H,m),4.19 (2H,dd,J=1.5 Hz,5.3 Hz),4.57(2H,s),5.66(1H,d,J=15.9 Hz), 6.09(1H,dt,J=15.5 Hz,6.5 Hz),6.34(1H,dt,J=15.8 Hz,5.3 Hz), 6.53(1H,d,J=15.8 Hz),6.97(1H,s),7.22-7.38(4H,m),7.79 (1H,s).

EXAMPLE 95

(E)-N-ethyl-N-(6,6-dimethyl-2-hepten-4-ynyl)-3-2-(3thienyloxy)ethoxymethyl]benzylamine IR(neat,cm$^{-1}$): 2968, 2932, 2872, 1548, 1362, 1179, 1110, 753.
$^1$H-NMR(300 MHz, CDCl$_3$, δppm):1.03(3H,t,J=7.3 Hz),1.24(9H, s),2.50(2H,q,J=7.3 Hz),3.09(2H,dd,J=6.3 Hz,1.7 Hz),3.55 (2H,s),3.80-3.82(2H,m),4.-

12-4.15(2H,m),4.61(2H,s), 5.64(1H,dt,J=15.9 Hz,1.7 Hz),6.07(1H,dt,J=15.9 Hz,6.3 Hz), 6.26(1H,dd,J=3.0 Hz,1.6 Hz),6.79(1H,dd,J=5.3 Hz,1.6 Hz), 7.16(1H,dd,J=5.3 Hz,3.0 Hz),7.15-7.31(4H,m).

EXAMPLE 96

Production of (E)-N-ethyl-N-(6,6-dimethyl-2-hepten-4-ynyl)-3-3-(3-thienylmethoxy)-2-oxopropyl]benzylamine A methylene chloride solution( 0.6 ml) of 25 μl of oxalyl chloride and a methylene chloride solution (1 ml) of 45 mg of dimethylsulfoxide were mixed at −70 ° C., and to this solution, a methylene chloride solution(1.5 ml) of 61 mg of (E)-N-ethyl-N-(6,6-dimethyl-2-hepten-4-ynyl)-3-[2-hydroxy-3-(3-thienylmethoxy)propyl]benzylamine was added. After stirring at −70° C. for 1 hour, 0.1 ml of triethylamine was added, and then the mixture was stirred at this temperature for 5 minutes. The solvent was evaporated under reduced pressure, and methylene chloride and water were added to the residue to extract it. The organic layer was separated, washed with a saturated aqueous solution of sodium chloride, and dried over anhydrous magnesium sulfate. The desiccant was separated by filtration, and the solvent was evaporated under reduced pressure. The residue was purified by medium-pressure liquid chromatography [silica gel column, hexane ethyl acetate 4/1] to give 43 mg (yield 70%) of the captioned compound as a colorless oil.

IR(neat,cm$^{-1}$): 2974, 1731, 1365, 1269, 1134, 1095, 783.

$^1$H-NMR(300 MHz, CDCl$_3$, δppm):1.03(3H,t,J=7.1 Hz),1.24(9H, s),2.49(2H,q,J=7.1 Hz),3.08(2H,dd,J=5.4 Hz,1.3 Hz),3.53 (2H,s),3.74(2H,s),4.10(2H,s),5.63(1H,dt,J=15.9 Hz,1.3 Hz),6.06(1H,dt,J=15.9 Hz,5.4 Hz),7.05-7.07(2H,m),7.-16-7.23(5H,m),7.31(1H,dd,J=4.8 Hz,2.9 Hz).

Compound of Example 97 was obtained by performing the same reaction as in Example 96 except that N-ethyl-N-(6,6-dimethyl-2-hepten-4-ynyl)-2-hydroxy-5-[3-(3-thienyl)phenoxy]pentylamine was used instead of the starting compound, (E)-N-ethyl-N-(6,6-dimethyl-2-hepten-4-ynyl)-3-[2-hydroxy-3-(3-thienyl-methoxy)-propyl]benzylamine, which was used in the above-mentioned reaction.

EXAMPLE 97

(E)-N-ethyl-N-(6,6-dimethyl-2-hepten-4-ynyl)-2-oxo-5-[3-(3-thienyl)phenoxy]pentylamine IR(neat,cm$^{-1}$): 2968, 1716, 1605, 1584, 1287, 1218, 1185, 771.

$^1$H-NMR(300 MHz, CDCl$_3$, δppm):1.03(3H,t,J=7.1 Hz),1.23(9H, s),2.08(2H,q,J=6.3 Hz),2.54(2H,q,J=7.1 Hz),2.70(2H,t,J=7.1 Hz),3.15(2H,dd,J=6.6 Hz,1.5 Hz),3.24(2H,s),5.62(1H, dt,J=15.9 Hz,1.5 Hz),6.02(1H,dt,J=15.9 Hz,6.6 Hz),6.81(1H, ddd,J=7.9 Hz,2.3 Hz,1.1 Hz),7.12(1H,t,J=2.2 Hz),7.17(1H, dt,J=8.0 Hz,1.4 Hz),7.30(1H,t,J=7.5 Hz),7.37(2H,d,J=2.2 Hz),7.45(1H,t,J=2.2 Hz).

EXAMPLE 98

Production of (E)-2-(N-ethyl-6,6-dimethyl-2-hepten-4-ynylamino)ethyl (E)-3-(3-thienyl)cinnamate 100 mg of 3-(3-thienyl)cinnamic acid was dissolved in 2 ml of chloroform, and 0.3 ml of thionyl chloride was added. The mixture was stirred at 70 ° C. for 1 hour, and then the solvent was evaporated under reduced pressure. A chloroform solution ( 2 ml) of 100 mg of (E)-2-(N-ethyl-6,6-dimethyl-2-hepten-4-ynylamino)ethanol was added to the residue, and the mixture was stirred at room temperature for 1 hour. The solvent was evaporated under reduced pressure, and the residue was purified by medium-pressure liquid chromatography [silica gel column, chloroform→chloroform/methanol=10/1] to give 23 mg (yield 11%) of the captioned compound as a colorless oil.

IR(neat,cm$^{-1}$): 2974, 1713, 1644, 1458, 1365, 1308, 1263, 1167, 981, 960, 777.

$^1$H-NMR(300 MHz, CDCl$_3$, δppm):1.05(3H,t,J=7.0 Hz),1.23(9H, s),2.61(2H,q,J=7.0 Hz),2.79(2H,t,J=6.1 Hz),3.21(2H,dd,J=6.6 Hz,1.2 Hz),4.28(2H,t,J=6.1 Hz),5.67(1H,dt,J=15.9 Hz, 1.2 Hz),6.06(1H,dt,J=15.9 Hz,6.6 Hz),6.50(1H,d,J=16.0 Hz), 7.38-7.47(4H,m),7.48(1H,dd,J=3.0 Hz,1.9 Hz),7.61(1H,dt, J=7.0 Hz,1.7 Hz),7.73(1H,d,J=16.0 Hz),7.73(1H,t,J=1.7 Hz).

EXAMPLE 99

Production of (E,E)-N-ethyl-N-(6-methoxy-6-methyl-2-hepten-4-ynyl)-4-[3-(3-thienyl)-2-propenoxymethyl]-2-pyridylmethylamine 11.6 mg of 60% oily sodium hydride was suspended in 0.5 ml of tetrahydrofuran at 0 ° C., under a nitrogen atmosphere, and a tetrahydrofuran solution( 2 ml) of 87.5 mg of (E)-N-ethyl-N-(6-methoxy-6-methyl-2-hepten-4-ynyl)-4-hydroxymethyl-2-pyridylmethylamine was added dropwise. The mixture was stirred for 20 minutes, and a tetrahydrofuran solution (1 ml) of 50 mg of (E)-3-bromo-1-(3-thienyl)-1-propene was added dropwise. The mixture was stirred overnight at room temperature, and then ice water and ethyl ether were added. The organic layer was separated, washed with a saturated aqueous solution of sodium chloride, and dried over anhydrous magnesium sulfate. The desiccant was separated by filtration, and the solvent was evaporated under reduced pressure. The residue was purified by medium-pressure liquid chromatography [silica gel column, chloroform→chloroform/methanol=20/1] to give 56 mg (yield 46%) of the captioned compound as a pale yellow oil.

IR(neat,cm$^{-1}$): 2980, 2938, 1362, 1248, 1173, 1152, 1113, 1074, 966.

$^1$H-NMR(300 MHz, CDCl$_3$, δppm):1.06(3H,t,J=7.1 Hz),1.45(6H, s),2.57(2H,q,J=7.1 Hz),3.18(2H,dd,J=6.4 Hz,1.5 Hz),3.34 (3H,s),3.73(2H,s),4.21(2H,dd,J=6.4 Hz,1.5 Hz),4.57(2H, s),5.69(1H,dd,J=15.7 Hz,1.5 Hz),6.17(1H,dt,J=15.7 Hz,6.4 Hz),6.18(1H,dt,J=15.7 Hz,6.4 Hz),6.66(1H,d,J=15.7 Hz), 7.17(1H,dd,J=4.9 Hz,1.0 Hz),7.19(1H,d,J=3.0 Hz),7.23(1H, dd,J=5.6 Hz,1.8 Hz),7.28(1H,dd,J=4.9 Hz,3.0 Hz),7.43-7.45 (1H,m),8.50(1H,dd,J=5.6 Hz,1.3 Hz).

EXAMPLE 100

Production of (E)-N-(6-acetoxy-6-methyl-2,4-heptadiynyl)-5-3-(3-thienyl)-2-propenoxymethyl]-2-furylmethylamine 196 mg of (E)-N-ethyl-N-(6-hydroxy-6-methyl-2,4-heptadiynyl)-5-[3-(3-thienyl)-2-propenyloxymethyl]-2-furylmethylamine [synthesized by condensing the same reaction as in Example 58 using (E)-N-ethyl-N-propargyl-5-[3-(3-thienyl)-2-propenyloxymethyl]-2-furylmethylamine and 1-bromo-3-hydroxy-3-methyl-1-butyne as starting materials]was dissolved in 2 ml of pyridine, and 106 μl of acetyl chloride and 60 mg of 4-dimethylaminopyridine were added. The solution was stirred at room temperature for 24 hours, and then the solvent was evaporated under reduced pressure. Ethyl acetate and water were added to the residue to extract it, and the organic layer separated was washed with water, then dried over anhydrous magnesium sulfate. The desiccant was separated by filtration, and the solvent was evaporated under reduced pressure. The residue was purified by silica gel column chromatography [hexane/ethyl acetate = 10/1→4/1] to give 51 mg (yield 26%) of the captioned compound as a pale yellow oil.

IR(neat,cm$^{-1}$): 1746, 1371, 1242, 1197, 1155, 1125, 1056, 1017, 966.

$^1$H-NMR(300 MHz, CDCl$_3$, δppm):1.09(3H,t,J=7.2 Hz),1.67(6H, s),2.03(3H,s),2.59(2H,q,J=7.2 Hz),3.46(3H,s),3.65(2H, s),4.14(2H,dd,J=6.0 Hz,1.2 Hz),4.46(2H,s),6.13(1H,dt,J=15.9 Hz,6.0 Hz),6.21(1H,d,J=3.2 Hz),6.26(1H,d,J=3.2 Hz), 6.62(1H,dt,J=15.9 Hz,1.2 Hz),7.15(1H,dd,J=3.0 Hz,1.2 Hz), 7.21(1H,dd,J=5.1 Hz,1.2 Hz),7.26(1H,dd,J=5.1 Hz,3.0 Hz).

EXAMPLE 101

Production of a powder and capsules containing the compound of Example 30 as active ingredients 1 g of the compound (hydrochloride) of Example 30, 12 g of lactose, 5.8 g of corn starch and 0.2 g of magnesium stearate were mixed uniformly to form a powder containing 1 g of the active ingredient per 20 g.

The powder obtained above was filled in hard gelatin capsules in an amount of 200 mg per capsule to give capsules containing 10 mg of the active ingredient per capsule.

The following Referential Examples illustrate the general synthesizing methods of the starting compounds used in the foregoing Examples.

Referential Example 1

Production of (E)-3-[3-(3-bromomethylbenzyloxy)-1-propenyl]thiophene 18 g of 3-thiophenecarboxaldehyde was dissolved in 300 ml of pyridine, and 25 g of malonic acid and 1.8 ml of piperidine were added. The mixture was refluxed for 3 hours, and the solvent was evaporated, then ethyl acetate and water were added to the residue to extract it. The organic layer was separated, washed with 1N hydrochloric acid, and the solvent was evaporated. The residue was treated with ethyl ether, and the precipitate was collected by filtration, then dissolved in 400 ml of methanol. 17.5 ml of thionyl chloride was added, and the mixture was stirred for 30 minutes. The solvent was evaporated, and the residue was worked up in a customary manner, then purified by silica gel column chromatography [hexane/ethyl acetate=3/1] to give 16.1 g of methyl (E)-α-(3-thienyl)acrylate as a pale yellow powder.

10 g of the resulting ester compound was dissolved in 200 ml of tetrahydrofuran, and 150 ml of a 1M diisobutylaluminum hydride toluene solution was added at −40° C. The mixture was stirred for 30 minutes, and the solvent was evaporated. The residue was worked up in a customary manner, and purified by silica gel column chromatography [hexane/ethyl acetate=1/1] to give 8.4 g of (E)-3-(3-thienyl)-2-propen-1-ol as a white powder.

1.3 g of the resulting alcohol compound and 3.0 g of α,α'-dibromo-m-xylene were dissolved in 15 ml of dimethylformamide, and 400 mg of 60% oily sodium hydride was added at −60° C. The mixture was stirred at room temperature for 30 minutes, and then the solvent was evaporated. The residue was worked up in a customary manner, and purified by silica gel column chromatography [hexane/ethyl acetate=60/1] to give 1.9 g of the captioned compound as a colorless oil.

When the same reactions as in Referential Example 1 are carried out using (E)-3-(3-chloromethylphenyl)-2-propen-1-ol [synthesized by the same reaction as in Referential Example 1 using 3-hydroxymethylbenzaldehyde, prepared by partial reduction of isophthalaldehyde, and malonic acid ] or 3-(3-thienyl)propanol[synthesized by the catalytic hydrogenation of (E)-3-(3-thienyl)-2-propen-1-ol in the presence of 10% palladium-carbon catalyst in methanol] and/or 3-bromothiophene, α,α'-dichloro-m-xylene 3,5-bis(chloromethyl)-1,2,4-oxadiazole[see Tetrahedron, 46,3941(1990)] or 2,6-bis(chloromethyl)pyridine instead of the starting (E)-3-(3-thienyl)-2-propen-1-ol and α,α'-dibromo-m-xylene, (E)-3-[3-(3-chloromethylphenyl)-2-propenyloxymethyl]thiophene, 3-[3-(3-chloromethylbenzyloxy)-propyl]thiophene (E)-3-chloromethyl-5-[3-(3-thienyl)-2-propenyloxymethyl]-1,2,4-oxadiazole and (E)-6-chloromethyl-2-[3-(3-thienyl)-2-propenyloxymethyl]-pyridine are obtained.

Referential Example 2

Production of (E)-4-(3-thienyl)-3-buten-1-ol 1.0 g of (3-hydroxypropyl)triphenylphosphonium bromide was dissolved in 20 ml of tetrahydrofuran, and under ice cooling, 3.4 ml of a 15% n-butyllithiumhexane solution was added. After the mixture was stirred for 30 minutes, 270 mg of 3-thiophenecarboxaldhyde was added. The mixture was stirred for 30 minutes, and then the solvent was evaporated. The residue was worked up in a customary manner, and purified by silica gel column chromatography [benzene/ethyl acetate=6/1] to give 28 mg (yield 7%) of the captioned compound as a colorless oil.

Referential Example 3

Production of (E,E)-N-methyl-N-(6,6-dimethyl-2-hepten-4-ynyl)-3-(4-chloro-2-butenyloxy)benzylamine 245 mg of (E)-N-methyl-N-(6,6-dimethyl-2-hepten-4-ynyl)-3-hydroxybenzylamine was dissolved in 5 ml of tetrahydrofuran, and under ice cooling, 40 mg of oily sodium hydride was added. After the mixture was stirred for 15 minutes, a dimethylformamide solution (3ml) of 125 mg of (E)-1,4-dichloro-2-butene was added. The mixture was stirred at room temperature for 12 hours, and then the solvent was evaporated. The residue was worked up in a customary manner, and purified by silica gel column chromatography [hexane/ethyl acetate=5/1] to give 216 mg of the captioned compound as a colorless oil.

Referential Example 4

Production of (E)-N-ethyl-N-(6,6-dimethyl-2-hepten-4-ynyl)-3-formylbenzylamine 440 mg of 3-bromomethylbenzaldehyde [synthesized by brominating 3-hydroxymethylbenzaldehyde with phosphorus tribromide ]was dissolved in 10 ml of dimethylformamide, and 535 mg of (E)-N-ethyl-6,6-dimethyl-2-hepten-4-ynylamine hydrochloride and 460 mg of potassium carbonate were added. The mixture was stirred overnight at room temperature, and then the solvent was evaporated. The residue was worked up in a customary manner, and purified by silica gel column chromatography [hexane/ethyl acetate=20/1] to give 670 mg of the captioned compound as a pale yellow oil.

When the same reactions as in Referential Example 4 are carried out using methyl 3-bromomethylbenzoate [synthesized by brominating methyl m-toluate with N-bromosuccinimide] or α,α'-dichloro-m-xylene instead of the starting 3-bromomethylbenzaldehyde, methyl (E)-3-(N-ethyl-6,6-dimethyl-2-hepten-4-ynylaminomethyl)benzoate or (E)-N-ethyl-N-(6,6-dimethyl-2-hepten-4-ynyl)-3-chloromethylbenzylamine is obtained.

Referential Example 5

Production of (E)-4-(3-thienyl)-3-buten-2-one 1.6 g of 3-thiophenecarboxaldehyde was dissolved in 30 ml of acetone, and 20 g of potassium carbonate was added. The mixture was stirred overnight at room temperature. The solvent was evaporated, and the residue was worked up in a customary manner. The resulting alcohol compound was dissolved in 10 ml of methylene chloride, and 1.1 ml of methanesulfonyl chloride and 2.3 ml of triethylamine were added. The mixture was stirred overnight at room temperature, and then the solvent was evaporated. The residue was worked up in a customary manner, and purified by silica gel column chromatography [hexane/ethyl acetate=40/1] to give 650 mg of the captioned compound as a pale yellow oil.

Referential Example 6

Production of S-[(E)-3-(3-thienyl)-2-propenyl]thioacetate 500 mg of (E)-3-(3-thienyl)-2-propen-1-ol was dissolved in 10 ml of ethyl acetate, and 0.3 ml of phosphorus tribromide was added under ice cooling. The mixture was stirred for 2 hours. The solvent was s evaporated, and the residue was worked up in a customary manner. The resulting brominated compound was dissolved in 5 ml of dimethylformamide, and 650 mg of potassium thioacetate was added under ice cooling. The mixture was stirred for 1 hour, and then the solvent was evaporated. The residue was worked up in a customary manner, and purified by silica gel column chromatography [hexane/ethyl acetate=50/1] to give 679 mg of the captioned compound as a pale yellow oil.

Referential Example 7

Production of 2-(3-thienylmethoxy)ethanol 621 mg of ethylene glycol was dissolved in 1 ml of tetrahydrofuran, and 88 mg of 60% oily sodium hydride and 0.5 ml of dimethylformamide were added. After the mixture was stirred at room temperature for 5 minutes, a tetrahydrofuran solution(1 ml) of 200 mg of 3-bromomethylthiophene was added. The mixture was stirred at 60 °C. for 2 hours, and then the solvent was evaporated. The residue was worked up in a customary manner to give 181 mg of the captioned compound as a pale yellow oil.

Referential Example 8

Production of (E)-N-ethyl-N-(6,6-dimethyl-2-hepten-4-ynyl)ethylenediamine 6.3 g of N-(2-bromoethyl)phthalimide [see Org. Syn. V, 585 was dissolved in 50 ml of dimethylformamide, and 5.0 g of (E)-N-ethyl-6,6-dimethyl-2-hepten-4-ynylamine hydrochloride and 4.1 9 of potassium carbonate were added. The mixture was stirred at 70 °C. for 6.5 hours, and then the solvent was evaporated. The residue was worked up in a customary manner, and purified by silica gel column chromatography [hexane/ethyl acetate 10/1→4/1], followed by treated with hexane to give 1.7 g of (E)-N-[2-(N'-ethyl-6,6-dimethyl-2-hepten-4-ynylamino)ethyl]phthalimide as a pale yellow powder.

1.5 g of the resulting phthalimide compound was dissolved in 15 ml of ethanol, and 0.23 ml of hydrazine hydrate was added. The mixture was stirred overnight at room temperature, and then the precipitate was removed by filtration. The solvent was evaporated and ethyl acetate and IN hydrochloric acid were added to the residue to extract it. The aqueous layer was separated, neutralized with potassium carbonate, and then extracted with ethyl acetate. The extract was worked up in a customary manner, and the solvent was evaporated to give 1.0 g of the captioned compound as a pale yellow oil.

Referential Example 9

Production of (E)-N-ethyl-N-(6,6-dimethyl-2-hepten-4-ynyl)glycine hydrochloride 1.0 g of (E)-N-ethyl-6,6-dimethyl-2-hepten-4-ynylamine hydrochloride was dissolved in 20 ml of dimethylformamide, and 0.7 g of methyl bromoacetate and 1.0 g of potassium carbonate were added. The mixture was stirred overnight at room temperature, and worked up in a customary manner. The resulting glycine ester compound was dissolved in a methanol solution (50 ml) of 0.5 g of sodium hydroxide, and 25 ml of water was added. The mixture was stirred at room temperature for 2 hours, and the solvent was evaporated. The residue was dissolved in water, and the solution was made weakly acidic with hydrochloric acid, then butanol and a saturated aqueous solution of sodium chloride were added. The organic layer was separated and the solvent was evaporated, then the residue was dissolved in a 10% hydrogenchloridemethanol solution. The solvent was re-evaporated, and the residue was treated with hexane to give 1.36 g of the captioned compound as a pale yellow powder.

Referential Example 10

Production of (E)-2-(N-ethyl-6,6-dimethyl-2-hepten-4-ynylamino)ethanol 1.3 g of (E)-N-ethyl-N-(6,6-dimethyl-2-hepten-4-ynyl)glycine methyl ester, obtained in Referential Example 9, was dissolved in 30 ml of ethyl ether, and 0.2 g of lithium aluminum hydride was added under ice cooling with stirring. The mixture was stirred for 1 hour, and then water was added. After the mixture was stirred for 1 hour, the precipitate was removed by filtration. The organic layer was separated, and the solvent was evaporated to give 1.0 g of the captioned compound as a pale yellow oil.

Referential Example 11

Production of (E)-β-4-(3-thienyl)-2-thienylacrylic acid 517 mg of 4-(3-thienyl)-2-thienylcarboxaldehyde, 552 mg of malonic acid and 41 μl of piperidine were dissolved in 30 ml of pyridine, and the mixture was refluxed for 5.5 hours. The solvent was evaporated, and the residue was dissolved in water. The resulting solution was acidified with hydrochloric acid, and extracted with ethyl acetate, then the extract was worked up in a customary manner to give 508 mg of the captioned compound as a pale yellow powder.

When the same reaction as in Referential Example 11 is carried out using 3-(3-thienyl)benzaldehyde instead of the starting (4-(3-thienyl)-2-thienylcarboxyaldehyde, (E)-3-(3-thienyl)cinnamic acid is obtained.

Referential Example 12

Production of 3-(3-thienyl)phenoxyacetic acid 0.5 g of 3-bromophenol and 0.33 ml of ethyl bromoacetate were dissolved in 4 ml of dimethylformamide, and 0.4 g of potassium carbonate was added. The mixture was stirred at 65°-70° C. for 3.5 hours. The solvent was evaporated, and the residue was worked up in a customary manner to give 0.6 g of ethyl 3-bromophenoxyacetate as a colorless oil.

2.6 g of the resulting ether compound, 5.3 g of tri-n-butyl(3-thienyl)tin and 20 mg of tetrakis(triphenhylphosphine)paladium were dissolved in 10 ml of xylene, and the mixture was refluxed for 5.5 hours. A 25% aqueous solution of potassium fluoride was added to the solution, and then the precipitate was removed by filtration. The organic layer separated was worked up in a customary manner, and the product was purified by silica gel column chromatography [hexane/ethyl acetate=20/1→15/1] to give 1.7 g of ethyl 3-(3-thienyl)-phenoxyacetate as a white powder.

0.7 g of the resulting thienyl compound was dissolved in 20 ml of ethanol, and 1 ml of a 10% aqueous solution of sodium hydroxide was added. The mixture was stirred at 60° C. for 10 minutes, and acidified with hydrochloric acid, then the solvent was evaporated. The residue was worked up in a customary manner to give 0.6 g of the captioned compound as a white powder.

When the same reactions as in Referential Example 12 are carried out using 3-bromothiophenol or 3-bromoaniline instead of the starting 3-bromophenol, 3-(3-thienyl)phenylthioacetic acid and 3-(3-thienyl)-phenylaminoacetic acid are obtained.

Referential Example 13

Production of (E)-3-(3-thienyl)cinnamaldehyde 1.0 g of 3-(3-thienyl)benzaldehyde, 0.5 g of cyanoacetic acid, 15 mg of ammonium acetate and 1 ml of pyridine were dissolved in 1.5 ml of xylene, and the mixture was refluxed for 5.5 hours. The solvent was evaporated, and the residue was dissolved in a mixture of ethyl ether and water, then the resulting solution was acidified with diluted hydrochloric acid. The organic layer separated was worked up in a customary manner, and the product purified by medium-pressure liquid chromatography [silica gel column, hexane/ethyl acetate=7/1→5/1] to give 0.4 g of (E)-3-(3-thienyl)cinnamonitrile as a white powder.

0.4 g of the resulting nitrile compound was dissolved in 2 ml of toluene, and under cooling at −78° C., a 1.0M toluene solution(2 ml) of diisobutylaluminum hydride was added. The mixture was stirred at this temperature for 20 minutes, and then poured into ice-cold water. The resulting solution was acidified with a small amount of a 10% aqueous solution of sulfuric acid, and extracted with ethyl ether. The extract was worked up in a customary manner, and purified by medium-pressure liquid chromatography [silica gel column, hexane/ethyl acetate=9/1→7/1] to give 0.2 g of the captioned compound as a pale yellow oil.

Referential Example 14

Production of 3-(3-thienyl)phenoxyacetaldehyde 0.54 g of ethyl 3-(3-thienyl)phenoxyacetate obtained in Referential Example 12 was dissolved in 5 ml of tetrahydrofuran, and under ice cooling with stirring, 76 mg of lithium aluminum hydride was added. The mixture was stirred for 20 minutes, and the solution was then worked up in a customary manner to give 0.43 g of 2-[3-(3-thienyl)phenoxy]ethanol as a white powder.

The resulting alcohol compound was oxidized in a similar manner to that described in J. Org. Chem., 43, 2481 (1978) using oxalyl chloride and dimethylsulfoxide to give the captioned compound.

Referential Example 15

Production of 3-[3-(3-thienyl)phenyl]propanal

To a suspension (20 ml) of 0.4 g of lithium aluminum hydride in terahydrofuran was added, under ice cooling, a tetrahydrofuran solution (10 ml) of 2.1 g of ethyl (E)-3-(3-thienyl)cinnamate [synthesized by the same reaction as in Referential Example 12 using ethyl (E)-3-bromocinnamate [see Org. Syn. I, 252] and tri-n-butyl(3-thienyl)tin ]. The mixture was stirred at room temperature for 30 minutes, and then refluxed for 30 minutes. The solution was worked up in a customary manner, and the product was purified by medium-pressure liquid chromatography [silica gel column, hexane/ethyl acetate=5/1→5/2] to give 1.1 g of 3-[3-(3-thienyl)phenyl]-1-propanol as a pale yellow oil.

150 mg of the resulting alcohol compound was dissolved in 5 ml of chloroform, and 222 mg of pyridinium chlorochromate was added. The mixture was stirred overnight at room temperature, and then the s precipitate was removed by filtration. The filtrate was Worked up in a customary manner, and the product was purified by silica gel column chromatography [hexane/ethyl acetate=5/1] to give 115 mg Of the captioned compound as a colorless oil.

Referential Example 16

Production of (E)-4-[3-(3-thienyl)phenyl]-3-buten-2-one 300 mg of 3-(3-thienyl)benzaldehyde was dissolved in 3 ml of acetone, and 441 mg of potassium carbonate was added. The mixture was stirred overnight at s room temperature, and then the solvent was evaporated. The residue was worked up in a customary manner, and purified by medium-pressure liquid chromatography [hexane/ethyl acetate =3/1]to give 1-[3-(3-thienyl)-phenyl]-3-oxo-1-butanol as a colorless oil.

The resulting alcohol compound was dissolved in 2 ml of ethyl acetate, and 207 mg of methanesulfonyl chloride and 366 mg of triethylamine were added. The mixture was stirred overnight at room temperature, and then the precipitate was removed by filtration. The filtrate was worked up in a customary manner, and the product was purified by silica gel column chromatography [hexane/ethyl acetate=5/1] to give 327 mg of the captioned compound as a pale yellow powder.

Referential Example 17

Production of
(E)-3-[3-(6-chloro-1-hexenyl)phenyl]thiophene 122 mg of 5-chloro-1-pentanol was dissolved in 1 ml of methylene chloride, and under ice cooling, 322 mg of pyridinium chlorochromate was added. The mixture was stirred with ice cooling for 10 minutes, and then at room temperature for 2 hours. The solution was worked up in a customary manner to give 5-chloro-pentanal.

400 mg of 3-(3-thienyl)benzyl(triphenyl)phosphonium bromide was dissolved in 2 ml of dimethylformamide, and under ice cooling, 37 mg of 60% oily sodium hydride was added. The mixture was stirred for 15 minutes, and to this solution was added an ethyl ether solution (0.6 ml) of the foregoing aldehyde compound. The mixture was stirred overnight at room temperature, and then the solvent was evaporated. The residue was worked up in a customary manner, and purified by silica gel column chromatography [hexane/ethyl acetate=19/1] to give 123 mg of the captioned compound (a mixture of E:Z=1:1) as a pale yellow oil.

Referential Example 18

Production of
(E)-3-3-(3-thienyl)phenyl]-2-propenylamine 3.8 g of (E)-3-(3-thienyl)cinnamic acid was dissolved in 50 ml of chloroform, and 10 ml of thionyl chloride was added. The mixture was stirred at 70 ° C. for 1 hour, and then the solvent was evaporated. Ethanol was added to the residue, and the solvent was evaporated again. The residue was purified by silica gel column chromatography [methylene chloride]to give 4.3g of ethyl (E)-3-(3-thienyl)cinnamate as pale yellow oil.

1.0 g of the resulting ester compound was reduced in a customary manner with lithium aluminum hydride, and then brominated by phosphorus tribromide. 0.7 g of (E)-3-[3-(3-thienyl)phenyl]-2-propenyl bromide obtained thus was dissolved in 10 ml of dimethylformamide, and 0.6 g of potassium phthalimide was added. The mixture was stirred overnight at room temperature, and the solution was worked up in a customary manner to give (E)-N-[3-[3-(3-thienyl)phenyl]-2-propenyl]phthalimide. 0.7 g of the resulting phthalimide compound was dissolved in a mixture (3 ml) of tetrahydrofuran and ethanol (1:1), and 0.5 ml of hydrazine hydrate was added. The mixture was stirred at room temperature for 1 hour, and then worked up in a customary manner to give 0.42 g of the captioned compound.

Referential Example 19

Production of
(E)-2-[3-[3-(3-thienyl)phenyl]-2-propenyloxy]ethanol 4.0 g of (E)-3-[3-(3-thienyl)phenyl]-2-propenyl bromide obtained in Reference Example 18 was dissolved in 70 ml of tetrahydrofuran, and 70 ml of ethylene glycol and 2.1 g of 60% oily sodium hydride were added. The mixture was heated at 100 ° C. with stirring for 1.5 hours. The solution was worked up in a customary manner, and then the product was purified by silica gel column chromatography [hexane/ethyl acetate=2/1] to give 3.7 g of the captioned compound as a pale yellow oil.

When the same reaction as in Referential Example 18 is carried out using (E)-3-[4-(3-thienyl)-2-thienyl]-2-propenyl bromide instead of the starting (E)-3-[3-(3-thienyl)phenyl]-2-propenyl bromide, (E)-2-[3-[4-(3-thienyl)-2-thienyl]-2-propenyloxy]ethanol is obtained.

Referential Example 20

Production of 2-[2-3-(3-thienyl)phenoxyethoxy]ethanol 400 mg of 2-[3-(3-thienyl)phenoxy]ethanol, obtained in Referential Example 14, was dissolved in 5 ml of tetrahydrofuran, and under ice cooling, 80 mg of 60% oily sodium hydride was added. The mixture was stirred for 5 minutes, and then a dimethylformamide solution (2 ml) of 0.22 ml of ethyl bromoacetate was added. The mixture was stirred at room temperature for 2 hours, and the solvent was evaporated. The residue was worked up in a customary manner, and purified by medium-pressure liquid chromatography [silica gel column, hexane/ethyl acetate=10/1→8/1] to give 320 mg of ethyl 2-[3-(3-thienyl)phenoxy]ethoxyacetate as a colorless oil.

311 mg of the resulting ester compound was reduced by lithium aluminum hydride as the same method in Referential Example 14 to give 276 mg of the captioned compound as a colorless oil.

Referential Example 21

Production of
5-3-(3-chloromethylbenzyloxy)-1-propenyl]-thiazole 700 mg of methyl β-(5-thiazolyl)acrylate [see Chem. Pharm. Bull., 35 823 (1987)] was dissolved in 10 ml of tetrahydrofuran, and under a nitrogen atmosphere, 8.1 ml of a 1M toluene solution of diisobutylaluminum hydride was added dropwise at −70° C. The mixture was stirred at this temperature for 50 minutes, and water and ethyl acetate were added to the solution. The precipitate was removed by filtration, and the filtrate was worked up in a customary manner to give 279 mg of 3-(5-thiazolyl)-2-propen-1-ol as a yellow oil.

38 mg of the resulting alcohol compound and 61 mg of α,α'-dichloro-m-xylene were dissolved in 1 ml of dimethylformamide, and under a nitrogen atmosphere with stirring, 12 mg of 60% oily sodium hydride was added at −42 ° C. The solution was gradually warmed to room temperature, and then stirred for 2 hours. The solution was worked up in a customary manner to give 37 mg of the captioned compound as a colorless oil.

Referential Example 22

Production of
3-2-2-(3-bromomethylphenyl)ethoxy]ethyl]thiophene 242 mg of 2-(3-thienyl)ethanol and 167 mg of 3-bromo-2-phenethyl alcohol were dissolved in 3 ml of benzene, and under a nitrogen atmosphere, 324 mg of silver trifluoromethanesulfonate was added. The mixture was refluxed for 5 hours, and then ethyl ether and water were added to the solution to extract it. The organic layer was separated, and worked up in a customary manner to give 186 mg of 3-[2-[2-(3-bromophenyl)ethoxy]ethyl]thiophene as a colorless oil.

46 mg of the resulting ether compound was dissolved in 1 ml of dimethylformamide, and 17 mg of copper cyanide was added. The mixture was stirred s overnight at 150 ° C. To this solution was added, a mixture of 39 mg of iron(II) chloride, 0.1 ml of water and 16 μl of hydrochloric acid, and the mixture was stirred at 60 ° C. for 30 minutes. The solution was extracted with ethyl ether, and the extract was worked up in a customary manner to give 17 mg of 3-[2-[2-(3cyanophenyl)ethoxy]ethyl]thiophene as a colorless oil.

17 mg of the resulting cyano compound was dissolved in 1 ml of toluene, and a 1M toluene solution (0.17 ml)of diisobutylaluminum hydride was added at −50° C. The mixture was stirred at this temperature for 1.5 hours. Water and 0.2 ml of 1N hydrochloric acid were added to the solution, and then the mixture was stirred at room temperature for 30 minutes. The solution was extracted with ethyl ether, and the extract was worked up in a customary manner to give 16 mg of 3-[2-[2-(3-thienyl)ethoxy]ethyl]benzaldehyde as a colorless oil.

The resulting aldehyde compound was reduced with sodium borohydride in ethanol, and subsequently brominated with phosphorus tribromide to give the captioned compound as a colorless oil.

Referential Example 23

Production of
3-[3-[2-(3-chloropropoxy)ethoxy]phenyl]thiophene 0.21 g of 60% oily sodium hydride was dissolved in a mixture of dimethylsulfoxide (5 ml) and tetrahydrofuran (5 ml), and a dimethylformamide solution (5 ml) of 1.08 g of trimethylsulfonium iodide was added dropwise at 0 ° C. with stirring. To this solution, a tetrahydrofuran solution(5 ml) of 1.0 g of 3-(3-thienyl)benzaldehyde was added at 0 ° C. with stirring. The mixture was stirred at room temperature for 60 hours, and then water was added to the solution. The organic layer was separated, and worked up in a customary manner to give 0.93 g of 3-(3-thienyl)phenyloxyrane as a colorless oil.

0.93 g of the resulting epoxide compound was added to a ethyl ether solution (30 ml) of diborane prepared from 0.33 g of aluminum chloride and 0.1 g of sodium borohydride. The mixture was refluxed for 1 hour, and water was added to the solution. The organic layer was separated, and worked up in a customary manner, then the product was purified by silica gel column chromatography [hexane/ethyl acetate=2/1] to give 0.26 g of 2-[3-(3-thienyl)phenyl]ethanol as a white powder.

55 mg of the resulting alcohol compound was dissolved in 1 ml of benzene, and under a nitrogen atmosphere, 80 μl of 1-bromo-3-chloropropane and 69 mg of silver trifluoromethanesulfonate were added. The mixture was refluxed for 16 hour while intercepting light, and then water was added to the solution. The organic layer was separated, and worked up in a customary manner, then the product was purified by silica gel column chromatoraphy [hexane/ethyl acetate=5/1] to give 24 mg of the captioned compound as a colorless oil.

Referential Example 24

Production of 3-3-(5-bromopentoxy)phenyl)thiophene 0.5 g of 3-(3-thienyl)phenol and 1.97 ml of 1, 5-dibromopentane were dissolved in 10 ml of dimethylformamide, and under ice cooling, 116 mg of 60% oily sodium hydride was added. The mixture was stirred at room temperature for 1 hour. The solvent was evaporated, and ethyl ether and water were added to the residue to extract it. The organic layer was worked up in a customary manner, and the product was purified by silica gel column chromatography [hexane/ethyl acetate=10/1] to give 0.83 g of the captioned compound as a colorless oil.

Referential Example 25

Production of
5-[3-[2-(2-chloroethoxy)ethoxy]phenyl]thiazole 260 mg of 3-(5-thiazolyl)phenol, 303 mg of 2-(2-chloroethoxy)ethyl methanesulfonate [synthesized by mesylating 2-(2-chloroethoxy)ethanol with methanesulfonyl chloride in the presence of triethylamine] and 621 mg of potassium carbonate were added to 5 ml of dimethylformamide, and the mixture was stirred at 55° C. for 5 hours. Water and ethyl acetate were added, and the organic layer separated was worked up in a customary manner, then the product was purified by medium-pressure liquid chromatography [silica gel column, hexane/ethyl acetate=15/2→15/7 and methylene chloride/ethyl acetate=10/1] to give 73 mg of the captioned compound as a colorless oil.

When the same reaction as in Referential Example 25 is carried out using 3-(3-pyridyl)phenol instead of the starting 3-(5-thiazolyl)phenol, 3-[3-[2-(2-chloroethoxy)ethoxy]phenyl]pyridine is obtained.

Referential Example 26

Production of
1-3-2-(2-chloroethoxy)ethoxy]phenyl]imidazole

An ethyl ether solution (3 ml) of 2.35 g of 3- [2-(2-chloroethoxy)ethoxy]aniline was added to a mixture of water (23 ml) and thiophosgene (0.83 ml), and the mixture was stirred at room temperature for 1 hour. Ethyl ether (30 ml) was added, and the organic layer was s separated. To the ether extract, 4.0 ml of 2,2-dimethoxyethylamine was added, and the mixture was stirred overnight at room temperature. The resulting solution was washed with water and the solvent was evaporated. The residue was purified by silica gel column chromatography [hexane / ethyl acetate=5/1→2/1] to give 3.41 g of N-[3-[2-(2-chloroethoxy)ethoxy]phenyl]-N'-(2,2-dimethoxyethyl)-thiourea as a pale yellow oil.

3.3 g of the resulting thiourea compound was dissolved in a mixture of methanol(10 ml) and 10% hydrochloric acid (40 ml), and the mixture was heated at 100° C. with stirring for 30 minutes. The solution was neutralized with sodium bicarbonate, and extracted with ethyl acetate. The extract was worked up in a customary manner, and the product was purified by silica gel column chromatography [hexane / ethyl acetate=2/1 →1/1] to give 0.46 g of 1-[3-[2-(2-ethoxy]phenyl]-2-mercaptoimidazole as a pale yellow oil.

0.25 g of the resulting imidazole compound was dissolved in 4 ml of 20% nitric acid, and the mixture was heated at 100° C. with stirring for 5 minutes. The solution was neutralized with sodium bicarbonate, and extracted with chloroform. The extract was worked up in a customary manner, and the product was purified by silica gel column chromatography [ethyl acetate/hexane=2/1→ethyl acetate] to give 0.16 g of the captioned compound as a colorless oil.

Referential Example 27

Production of
N-ethyl-6,6-dimethyl-2,4-heptadiynylamine
hydrochloride

A methanol solution (7.5 ml) of 0.75 ml of propargyl bromide was added dropwise to 6 ml of a 70% aqueous solution of ethylamine with stirring and ice cooling, and the mixture was stirred for 1.5 hours. 120 mg of copper(I) chloride and 100 mg of hydroxylamine hydrochloride were added, and to this solution, a methanol solution(3 ml) of 5.6 mg of 1-bromo-3,3-dimethyl-1-butyne [synthesized by a bromination of lithiated tert-butylacetylene with bromine ] was added dropwise under ice cooling. The mixture was stirred at room temperature for 2 hours, and then the solvent was evaporated. The residue was worked up in a customary manner, and the product was treated with a methanol solution of hydrogen chloride to give 0.94 g of the captioned hydrochloride as a white crystalline powder.

Referential Example 28

Production of
(E)-5-[3-(3-thienyl)phenoxy]-2-penten-1-ol 1.3 g of 3-(3-thienyl)phenol, 1.09 ml of 3-bromopropanal dimethylacetal and 1.1 g of potassium carbonate were dissolved in 10 ml of dimethylformamide, and the mixture was heated at 90° C. with stirring for 6 hours. Ethyl acetate and water were added, and the organic layer separated was worked up in a customary manner, then the product was purified by silica gel column chromatography [hexane / ethyl acetate=30/1→20/1] to give 1.0 g of 3-[3-(3-thienyl)-phenoxy] propanal dimethylacetal as a colorless oil.

0.46 g of the resulting ether compound was dissolved in 5 ml of tetrahydrofuran, and 2 ml of 2N hydrochloric acid was added. The mixture was allowed to stand at room temperature for 4 hours, and then the solution was made basic with an aqueous solution of sodium bicarbonate. The solution was extracted with s ethyl acetate, and the extract was worked up in a customary manner. The product was purified by silica gel column chromatography [hexane / ethyl acetate =20/1→10/1] to give 0.28 g of 3-[3-(3-thienyl)phenoxy]propanal as a colorless oil.

0.28 g of the resulting aldehyde compound was dissolved in 5 ml of benzene, and 0.5 g of methyl (triphenylphosphoranylidene)acetate was added. The mixture was stirred overnight at room temperature. The reaction solution was worked up in a customary manner, and the product was purified by silica gel column chromatography [hexane / ethyl acetate=10/1] to give 0.21 g of 5-[3-(3-thienyl)phenoxy]-2-pentenoate as a colorless oil.

143 mg of the resulting ester compound was dissolved in 3 ml of tetarahydrofuran, and under a nitrogen atmosphere, 1.02 ml of a 1M toluene solution of diisobutylaluminum hydride was added dropwise with stirring at −60° C. An aqueous solution of citric acid and ethyl ether were added to the solution to extract it. The organic layer separated was worked up in a customary manner, and the product was purified by silica gel column chromatography [hexane / ethyl acetate =5/1] to give 90 mg of the captioned compound as a colorless oil.

Referential Example 29

Production of
(E)-4-[3-(3-thienyl)benzyloxy]-2-buten-1-ol

Under a nitrogen atmosphere, 0.47 g of 60% oily sodium hydride was suspended in 10 ml of dimethylformamide, and a dimethylformamide solution (10 ml) of 1.0 g of 2-butyn-1,4-diol was added dropwise with stirring and ice cooling. After the mixture was stirred for 10 minutes, a dimethylformamide solution (5 ml) of 0.59 g of 3-(3-bromomethylphenyl)thiophene was added. The mixture was stirred at room temperature for 1 hour and then ethyl ether and water were added. The organic layer separated was worked up in a customary manner, and the product was purified by silica gel column chromatography [hexane / ethyl acetate=3/1] to give 0.48 g of 4-[3-(3-thienyl)benzyloxy]-2-butyn-1-ol as a colorless oil.

0.48 g of the resulting alcohol compound was dissolved in 5 ml of tetarahydrofuran, and under a nitrogen atmosphere, a tetrahydrofuran solution (5 ml) of 78 mg of lithium aluminum hydride was added. The mixture was stirred under ice cooling for 2 hours, and then at room temperature for 1 hour. Ethyl acetate and water were added, and the organic layer separated was worked up in a customary manner. The product was purified by silica gel column chromatography [hexane / ethyl acetate=4/1] to give 0.28 g of the captioned compound as a colorless oil.

Referential Example 30

Production of
1-[3-(3-thienyl)phenoxy]-5-bromo-2-pentanone 0.25 g of 3-(3-thienyl)phenol was dissolved in 2.5 ml of dimethylformamide, and 28 mg of 60% oily sodium hydride was added. The mixture was stirred at room temperature for 15 minutes, and then a dimethylformamide solution (1 ml) of 0.45 g of 1,5-dibromo-2-pentanone [see J. Chem. Soc., 1948, 278] was added dropwise at −40° C. The mixture was stirred at this temperature for 2 hours, and ethyl ether and water were added. The organic layer separated was worked up in a customary manner, and the product was purified by silica gel column chromatography [hexane / ethyl acetate=30/1] to give 50 mg of the captioned compound as a colorless oil.

Referential Example 31

Production of
2-(2-hydroxyethoxy)-1-3-(3-thienyl)phenoxy]propane
oxy]propane 0.68 g of 1-[3-(3-thienyl)phenoxy]-2-propanol [synthesized by reducing 3-(3-thienyl)phenoxyacetone, prepared by the reaction of 3-(3-thienyl)phenol and monobromoacetone in the presence of potassium carbonate, with sodium borohydride in ethanol] was dissolved in 7 ml of dimethylformamide, and 48 mg of 60% oily sodium hydride was added. After the mixture was stirred at room temperature for 20 minutes, 0.12 ml of ethyl bromoacetate was added. The mixture was stirred at room temperature for 2 hours, and then ethyl ether and water were added. The organic layer separated was worked up in a customary manner, and the product was purified by silica gel column chromatography [hexane / ethyl acetate=10/1] to give 0.12 g of methyl [1-methyl- 2-[3-(3-thienyl)phenoxy]ethoxy]acetate as a colorless oil.

0.12 g of the resulting ester compound was dissolved in 5 ml of tetrahydrofuran, and under ice cooling, 15 mg of lithium aluminum hydride was added. The mixture was stirred at room temperature for 2 hours, and ethyl acetate and water were added. The organic layer separated was worked up in a customary manner, and the product was purified by silica gel column chromatography [hexane / ethyl acetate=3/1] to give 83 mg of the captioned compound as a colorless oil.

Referential Example 32

Production of 2-[2-[3-(3-thienyl)phenoxy]ethoxy]propanol 0.22 g of 2-[3-(3-thienyl)phenoxy]ethanol was dissolved in 7 ml of tetrahydrofuran, and 48 mg of 60% oily sodium hydride was added. After the mixture was stirred at room temperature for 20 minutes, a dimethylformamide solution (5 ml) of 0.14 ml of methyl α-bromopropionate was added. The mixture was stirred at room temperature for 1.5 hours, and then ethyl ether and water were added. The organic layer separated was worked up in a customary manner, and the product was purified by silica gel column chromatography [hexane / ethyl acetate=10 / 1] to give 0.22 g of methyl 2-[2-[3-(3-thienyl)phenoxy] ethoxy]propionate as a colorless oil.

0.20 g of the resulting ester compound was dissolved in 5 ml of tetrahydrofuran, and reduced as in Referential Example 31 with 25 mg of lithium alminum hydride to give 0.18 g of the captioned compound as a colorless oil.

Referential Example 33

Production of (E)-N-ethyl-5-[3-(3-thienyl)-2-propenyloxymethyl]-2-furylmethylamine hydrochloride 16.8 g of 5-hydroxymethyl-2-furaldehyde was dissolved in 70 ml of methanol, and 14.7 ml of methyl orthoformate and 170 mg of pyridinium p-toluenesulfonate were added. After the mixture was stirred at room temperature for 2 hours, 350 mg of sodium bicarbonate was added. The solution was stirred at room temperature for 30 minutes, and then ethyl ether and water were added. The organic layer separated was worked up in a customary manner to give 21.6 g of 5-hydroxymethyl-2-furaldehyde dimethylacetal as a pale brown oil.

Under a nitrogen atmosphere, a tetrahydrofuran solution (210 ml) of 21.3 g of the resulting acetal compound was added by portion to a suspension of 5.01 g of 60% oily sodium hydride in tetrahydrofuran (20 ml). The mixture was stirred under ice cooling for 30 minutes, and to its solution, a tetrahydrofuran solution (150 ml) of 20.9 g of (E)-3-(3-thienyl)-2-propenyl bromide was added dropwise over 1 hour at −20° C. The solution was warmed to 0° C., and 7 ml of dimethylformamide was added, then the mixture was stirred overnight at 5~10° C. Water and ethyl ether were added, and the organic layer separated was worked up in a customary manner to give 22.0 g of (E)-5-[3-(3-thienyl)-2-propenyloxymethyl]-2-furaldehyde dimethylacetal as a pale yellow oil.

Under a nitrogen atmosphere, 22.0 g of the resulting acetal compound was dissolved in 650 ml of tetrahydrofuran, and 223 ml of 0.1N hydrochloric acid was added dropwise under ice cooling. The mixture was stirred overnight at 5~10° C., and then water and ethyl ether were added. The organic layer separated was worked up in a customary manner, and the product was recrystalized from a mixture of ethyl ether and hexane to give 16.8 g of (E)-5-[3-(3-thienyl)-2-propenyloxymethyl]-2-furaldehyde as a white crystalline powder.

16.2 g of the resulting aldehyde compound was dissolved in 50 ml of tetrahydrofuran, and 90 ml of a 2.2M ethylamine - ethanol solution was added. The mixture was allowed to stand overnight at room temperature, and then the solvent was evaporated. An additional amount (60 ml) of a 2.2M ethylamine - ethanol solution was added to the residue, and the mixture was then left at room temperature for 1 hour. The solvent was evaporated, and the residue was dissolved in 150 ml of ethanol. 2.9 g of sodium borohydride was added, and then the mixture was stirred at room temperature for 1 hour. The solvent was evaporated, and methylene chloride and water were added. The organic layer separated was worked up in a customary manner, and the resulting oily free base was dissolved in 300 ml of ethyl ether under ice cooling. To this solution, 150 ml of a 0.5M hydrogenchloride-ethyl ether solution was added dropwise with ice cooling and stirring, and the precipitate was collected by filtration to give 17.5 g of the captioned compound as a white crystalline powder.

When the same reactions as in Referantial Example 33 are carried out using ethanol or methanol solutions of various amines instead of the ethylamineethanol solution, (E)-N-methyl-5-[3-(3-thienyl)-2-propenyloxymethyl]-2-furylmethylamine hydrochloride,(E)-N-propyl-5-[3-(3-thienyl)-2-propenyloxymethyl]-2-furylmethylamine hydrochloride, (E)-N-(2-fluoroethyl)-5-[3(3-thienyl)-2-propenyloxymethyl]-2-furylmethylamine and (E)-N-cyclopropyl-5-[3-(3-thienyl)-2-propenyloxymethyl]-2-furylmethylamine are obtained.

Referential Example 34

Production of N-cyclopropyl-2-[2-[3-(3-thienyl)phenoxy]ethoxy]ethylamine 0.36 g of 2-[3-(3-thienyl)phenoxy]ethoxyacetic acid was dissolved in 7 ml of tetrahydrofuran, and under ice cooling, 110 μl of methyl chloroformate and 200 μl of triethylamine were added. After the mixture was stirred with cooling for 30 minutes, 178 μl of cyclopropylamine was added. The mixture was stirred at room temperature for 1 hour, and then ethyl ether and water were added. The organic layer separated was worked up in a customary manner to give 0.31 g of N-cyclopropyl-2-[3(3-thienyl)phenoxy]ethoxyacetamide as a pale yellow oil.

0.31 g of the resulting amide compound was dissolved in 3 ml of tetrahydrofuran, and 4 ml of a 1M diborane-tetrahydrofuran solution was added. The mixture was refluxed for 3 hours, and water and ethyl actate were added. The organic layer separated was worked up in a customary manner to give 0.25 g of the captioned compound as a pale yellow oil.

When the same reactions as in Referential Example 34 are carried out using ethylamine or 2-fluoroethylamine instead of the starting cyclopropylamine, N-ethyl-2-[2-[3-(3-thienyl)phenoxy]ethoxy]ethylamine and N-(2-fluoroethyl)-2-[2-[3-(3-thienyl)phenoxy]ethoxy]ethylamine are obtained.

Referential Example 35

Production of N-ethyl-2-[2-3-(3-thienyl)phenoxy}ethylthio]ethylamine

2-[3-(3-thienyl)phenyl]ethyl methanesulfonate, [synthesized by reacting 100 mg of 2-[3-(3-thienyl)phenoxy]ethanol with 50 μl of methanesulfonyl chloride and 190 μl of triethylamine in 1 ml of ethyl acetate] was dissolved in 1.5 ml of dimethylformamide, and 68 mg of potassium thioacetate was added. The mixture was heated at 80° C. with stirring for 3 hours, and then water and ethyl acetate were added. The organic layer separated was worked up in a customary manner to give 111 mg of S-[2-[3-(3-thienyl)phenoxy]ethyl] thioacetate as a pale brown oil.

55 mg of the resulting thioester compound, 30 mg of N-ethylchloroacetamide and 50 mg of potassium carbonate were dissolved in 2 ml of methanol, and the mixture was stirred at room temperature for 40 minutes. Water and ethyl actate were added, and the organic layer separated was worked up in a customary manner, then the product was purified by medium-pressure liquid chromatography [hexane / ethyl acetate=2/1→1/2] to give 58 mg of N-ethyl-2-[3-(3-thienyl)phenoxy]ethylthioaoetamide as a colorless oil.

58 mg of the resulting amide compound was dissolved in 2 ml of tetrahydrofuran, and under a nitrogen atmosphere, 1.6 ml of a 1M diboran-tetrahydrofuran solution was added dropwise at 0° C. The mixture was stirred at this temperature for 30 minutes, and then IN hydrochloric acid was added to the solution to adjust its pH to 1.0. The slovent was evaporated, and then the residue was dissolved in a mixture of water and ethyl ether. After the solution was made basic with a 1N aqueous solution of sodium hydroxide, the organic layer was separated, and worked up in a customary manner. The product was purified by silica gel column chromatography [chloroform / methanol=10/1→4/1] to give 37 mg of the captioned compound as a colorless oil.

Referential Example 36

Production of (E,E)-3-5-(3-thienyl)-2,4-pentadienyl]benzylalcohol 46 mg of methyl (E,E)-5-(3-thienyl)-2,4-pentadienoate was dissolved in 1 ml of tetrahydrofuran, and 0.59 ml of a 1M toluene solution of diisobutylaluminum hydride was added dropwise at −40° C. Water, 0.6 ml of 1N hydrochloric acid and ethyl acetate were added to the solution , and the organic layer separated was worked up in a customary manner to give 40 mg of (E,E)-5-(3-thienyl)-2,4-pentadien-1-ol as a colorless oil.

20 mg of the resulting alcohol compound was dissolved in 1.5 ml of ethyl acetate, and under ice cooling, an ethyl acetate solution (0.5 ml) of 16.2 mg of phosphorus tribromide was added dropwise. The mixture was stirred for 1 hour, and then the solvent was evaporated. The residue was dissolved in 3 ml of toluene, and under a nitrogen atmosphere, 59 mg of 3-(tributylstannyl)benzaldehyde and 3 mg of tetrakis(triphenylphosphine)palladium were added. After the mixture was refluxed for 3 hours, 1 ml of a saturated aqueous solution of potassium fluoride was added, and the mixture was stirred at room temperature for 30 minutes. Water and ethyl acetate were added, and the organic layer separated was worked up in a customary manner. The product was purified by medium-pressure liquid chromatography [hexane / ethyl acetate=8/1] to give 7 mg of (E,E)-3-[5-(3-thienyl)-2,4-penta-dienyl]benzaldehyde as a pale yellow oil.

6 mg of the resulting aldehyde compound was dissolved in 1 ml of ethanol, and 1 mg of sodium borohydride was added. The mixture was stirred at room temperature for 15 minutes, and then water and ethyl ether were added. The organic layer separated was worked up in a customary manner to give 6 mg of the captioned compound as a pale yellow oil.

Referential Example 37

Production of (E)-6,6-dimethyl-4-hepten-2-yn-1-ol 0.63 g of (E)-1- iodo-3,3-dimethyl-1-butene [see J. Org. Chem., 43, 4424 (1978)] was dissolved in 10 ml of tetrahydrofuran, and 31 mg of triphenylphosphine, 29 mg of copper(I) iodide, 11 mg of palladium chloride, 1.5 ml of n-butylamine and 0.35 ml of propargyl alcohol were added. The mixture was stirred overnight at room temperature, and then water and ethyl acetate were added. The organic layer separated was worked up in a customary manner, and the product was purified by silica gel column chromatography [hexane/ethyl acetate=2/1] to give 0.27 g of the captioned compound as a pale brown oil.

Referential Example 38

Production of 6-methoxy-6-methyl-2,4-heptadiyn-1-ol 200 ml of a 70% aqueous solution of ethyamine, 1 g of copper(I) chloride, 5 g of hydroxylamine hydrochloride and 25 g of propargyl alcohol were dissolved in 500 ml of methanol, and with ice cooling and stirring, a methanol solution (100 ml) of 74 g of 1-bromo-3-methoxy-3-methyl-1-butyne was added. The mixture was stirred at room temperature for 1 hour, and then the solvent was evaporated. Water and ethyl acetate were added, and the insoluble material was removed by filtration. The organic layer separated was worked up in a customary manner, and the product was purified by vacuum distillation ( b.p. −97° C. / 2 mmHg ) to give 57 g of the captioned compound as a colorless oil.

Referential Example 39

Production of 6-methoxy-6-methyl-4-hepten-2-yn-1-ol 1 g of 7-tert-butyldimethylsilyloxy-2-methyl-3,5-heptadiyn-2-ol [synthesized by the same reaction as Referential Example 38 using tert-butyldimethylpropargyloxysilane and 4-bromo-2-methyl-3-butyn-2-ol] was dissolved in 10 ml of tetrahydrofuran, and under ice cooling, 190 mg of lithium alminum hydride was added. The mixture was stirred at this temperature for 1 hour, and then was poured into ice-cold water. The resulting solution was extracted with ethyl ether, and the extract was worked up in a customary manner, then purified by silica gel column chromatography [hexane / ethyl acetate =15/1] to give 0.80 g of 7-tert-butyldimethylsilyloxy-2-methyl-3-hexen-5-yn-2-ol.

The resulting en-yne compound (800 mg) was dissolved in 10 ml of dimethylformamide, and under a nitrogen atmosphere and ice cooling, 150 mg of 60% oily sodium hydride was added. The mixture was stirred under ice cooling for 10 minutes, and 0.34 ml of dimethylsulfate was added. The reaction solution was stirred at this temperature for 1 hour and at room temperature for 1 hour, then poured into ice-cold water. The resulting solution was extracted with ethyl ether, and the extract was worked up in a customary manner.

The resulting methoxy compound was dissolved in 10 ml of tetrahydrofuran, and under ice cooling, 4 ml of a 1M tetrabutylammonium fluoride-tetrahydrofuran solution was added. The mixture was stirred at this temperature for 1 hour, and then poured into ice water. The resulting solution was extracted with ethyl ether, and the extract was worked up in a customary manner, then purified by silica gel column chromatography [hexane / ethyl acetate=4/1] to give 280 mg of the captioned compound as a colorless oil.

Referential Example 40

Production of 6,6-dimethyl-4-heptynyl methanesulfonate 0.81 g of tert-butylacetylene was dissolved in 19 ml of tetrahydrofuran, and 6.1 ml of a 0.55M n-butyllithium-hexane solution was added dropwise with stirring at −78° C. After the mixture was stirred at this temperature for 1 hour, 2.2 g of 3-bromo-1-(2-tetrahydropyranyloxy)propane was added. The solution was warmed to the room temperature, and then heated at 80° C. with stirring for 8 hours. The reaction mixture was poured into the ice water, and ethyl ether was added. The organic layer separated was worked up in a customary manner, and the product was purified by silica gel column chromatography [hexane / ethyl acetate=20 /1] to give 0.90 g of 6,6-dimethyl-1-(2-tetrahydropyranyloxy)-4-heptyne.

0.90 g of the resulting heptyne compound was dissolved in 18 ml of methanol, and 6 ml of 1N hydrochloric acid was added. The mixture was stirred at s room temperature for 2 hour, and then the solvent was evaporated. Ethyl ether and a saturated aqueuos solution of sodium bicarbonate was added , and the organic layer separated was worked up in a customary manner. The product was purified by silica gel column chromatography [hexane / ethyl acetate=20/1] to give 0.26 g of 6,6-dimethyl-4-heptyn-1-ol.

100 mg of the resulting alcohol compound was dissolved in 1 ml of ethyl acetate, and 60 μl of methanesulfonyl chloride and 200 μl of triethylamine were added. The mixture was stirred at room temperature for 1 hour, and then the precipitate of triethylamine hydrochloride was removed by filtration. The filtrate was diluted with ethyl acetate, and washed succesively with a saturated aqueous solution of sodium bicarbonate, 1N hydrochloric acid and a saturated aqueous slution of sodium chloride, then worked up in a customary manner to give 150 mg of the captioned compound as a colorless oil.

Referential Example 41

Production of 5-[3-(3-thienyl)phenoxy]pentylamine 0.65 g of 3-[3-(5-bromopentyloxy)phenyl]thiophene, 0.37 g of potassium phthalimide and 0.14 g of potassium carbonate were dissolved in 5 ml of dimethylformamide, and the mixture was heated at 50° C. with stirring for 5 hours. Ethyl acetate and water were added, and the organic layer separated was worked up in a customary manner. The product was purified by silica gel column chromatography [hexane / ethyl acetate=7/1 →5/1] to give 0.36 g of N-[5-[3-(3-thienyl)phenoxy]pentyl] phthalimide as a colorless oil.

0.36 g of the resulting phthalimide compound was dissolved in a mixture of ethanol (10 ml) and tetrahydrofuran (3 ml), and 1 ml of hydrazine hydrate was added. The mixture was stirred at room temperature for 2 hours, and then chloroform and water were added. The organic layer separated was worked up in a customary manner, and the product was purified by silica gel column chromatography [chloroform / methanol 3/1 →1/1] to give 0.17 g of the captioned compound as a pale yellow oil.

When the same reaction as in Referential Example 39 is carried out using 3-[3-[2-(2-chloroethoxy)ethoxy]-phenyl]thiophene instead of using the starting 3-[3-(5-bromopentyloxy)phenyl] thiophene, 2-[2-[3-(3-thienyl)-phenoxy]ethoxy ]ethylamine is obtained.

Referential Example 42

Production of (E)-N-ethyl-N-(7,7,7-trifluoro-6-trifluoromethyl-6-hydroxy-2-hepten-4-ynyl)-2-2-[3-(3-thienyl)phenoxy]ethoxy]ethylamine 1.9 g of N-ethyl-2-[2-[3-(3-thienyl)phenoxy]ethoxy]ethylamine and 2.7 g of potassium carbonate were dissolved in 15 ml of dimethylformamide, and a dimethylformamide solution (5 ml) of 1.43 g of (E)-5-bromo-3-penten-1-ynyl(trimethyl)silane [synthesized by mesylating 3-hydroxy-4-penten-1-ynyl(trimethyl)silane, prepared from trimethylsilylacetylene and acrolein, with methanesulfonyl chloride and triethylamine, and subsequently treating the mesylated product with trimethylammonium bromide] was added dropwise. The mixture was stirred at room temperature for 30 minutes, and then ethyl acetate and water were added. The organic layer separated was worked up in a customary manner, and the product was purified by silica gel column chromatography [methylene chloride / methanol=20/1] to give 2.3 g of (E)-N-ethyl-N-(5-trimethylsilyl-2-penten-4-ynyl)-2-[2-[3-(3-thienyl) phenoxy]ethoxy]ethylamine as a colorless oil.

2.0 g of the resulting allylamine compound was dissolved in a mixture of methanol (5 ml) and tetrahydrofuran (5 ml), and 10 ml of a saturated aqueous solution of potassium fluoride was added. The mixture was stirred overnight at room temperature, and then ethyl acetate and water were added. The organic layer s separated was worked up in a customary manner, and the product was purified by silica gel column chromatography [methylene chloride / methanol=100/1] to give 1.3 g of (E)-N-ethyl-N-(2-penten-4-ynyl)-2-[2-[3-(3-thienyl) phenoxy)ethoxy]ethylamine as a colorless oil.

240 mg of the above-obtained compound was dissolved in 6 ml of tetrahydrofuran, and under a nitrogen atmosphere, 0.48 ml of a 1.6M n-butyllithiumhexane solution was added at −78° C. After the mixture was stirred at this temperature for 40 minute, 0.5 ml of hexafluoroacetone was added. The mixture was stirred at −78° C. for 1 hour, and then ethyl acetate and water were added. The organic layer separated was worked up in a customary manner, and the product was purified by silica gel column chromatography [methylene chloride / methanol =50/1] to give 185 mg of the captioned compound as a colorless oil.

Referential Example 43

Production of 3-(3-thienyloxy)propanol 68 mg of sodium was added to 10 ml of 1,3-propandiol, and the mixture was stirred at room temperature for 1 hour. The reaction solution was warmed to 70° C., and to this solution were added, 126 μl of 3-bromothiophene, 13 mg of copper(I) iodide and 16 mg of copper-(II) oxide. The mixture was heated at 150° C. with stirring for 20 hours, and then poured into the ice-cold water. The resulting solution was neutralized with diluted hydrochloric acid, and extracted with ethyl ether. The extract was worked up in a customary manner, and the product was purified by medium-pressure liquid chromatography [silica gel column, hexane ethyl acetate=20/1→5/1] to give 49 mg of the captioned compound as a white crystal.

Referential Example 44

Production of (E)-N-ethyl-N-(4-oxopentyl)-6,6-dimethyl-2-hepten-4-ynylamine 0.33 g of 2-(3-chloropropyl)-2-methyl-1,3-dioxorane, 0.33 g of potassium iodide, 0.69 g of potassium carbonate and 0.61 g of (E)-N-ethyl-6,6-dimethyl-2-hepten-4-ynylamine hydrochloride were dissolved in 5 ml of dimethylformamide, and the mixture was stirred at 100° C. for 14 hours. Water and ethyl acetate were added, and then the organic layer separated was worked up in a customary manner. The product was purified by silica gel column chromatography [hexane / ethyl acetate=1/1] to give 0.51 g of ethylene acetal of the captioned ketone.

The resulting ethylene acetal compound (0.51 g) was dissolved in 5 ml of tetrahydrofuran, and 5 ml of 1N hydrochloric acid was added. The mixture was stirred at room temperature for 2 hours, and then a saturated aqueous solution of sodium bicarbonate was added to the mixture to make it basic. Ethyl acetate and water were added, and the organic layer separated was worked up in a customary manner to give 0.43 g of the captioned compound as a colorless oil.

Referential Example 45

Production of 3-thienylmethoxyacetic acid 1.0 g of 3-thiophenemethanol was dissolved in 6 ml of dimethylformamide, and under ice cooling, 0.36 g of 60% oily sodium hydride and 1 ml of ethyl bromoacetate were added. The mixture was stirred at room temperature for 15 hours, and then worked up in a customary manner. The product was purified by silica gel column chromatography [hexane / ethyl acetate=6/1] to give 0.9 g of ethyl 3-thienylmethoxyacetate as a colorless oil.

0.9 g of the resulting ether compound was dissolved in 10 ml of ethanol, and an aqueous solution(10 ml) of 1.44 g of sodium hydroxide was added. The mixture was refluxed for 4 hours, and then acetic acid was added to the solution to acidify it. The solvent was evaporated, and ethyl acetate and water were added. The organic layer separated was worked up in a customary manner to give 0.75 g of the captioned compound as a colorless oil.

Referential Example 46

Production of (E)-3-(N-ethyl-6,6-dimethyl-2-hepten-4-ynylaminomethyl)phenylacetic acid 240 mg of (E)-N-ethyl-N-(6,6-dimethyl-2-hepten-4-ynyl)-3-bromomethylbenzylamine was dissolved in 4 ml of dimethylformamide, and 61 mg of sodium cyanide was added. The mixture was stirred overnight at room temperature, and then ethyl ether and water were added. The organic layer separated was worked up in a customary manner to give 195 mg of (E)-3-(N-ethyl-6,6-dimethyl-2-hepten-4-ynylaminomethyl)phenylacetonitrile as a colorless oil.

195 mg of the resulting nitrile compound was dissolved in 6 ml of ethanol, and a 3N aqueous solution (2ml) of sodium hydroxide was added. The mixture was refluxed for 3 hours, and then acidified with 1N hydrochloric acid. Ethyl acetate and water were added, and the organic layer separated was worked up in a customary manner. The product was purified by silica gel column chromatography [ethyl acetate / methanol=20/1] to give 176 mg of the captioned compound as a colorless oil.

Referential Example 47

Production of (E)-N-ethyl-N-(6,6-dimethyl-2-hepten-4-ynyl)-3-aminomethylbenzylamine 0.57 g of potassium phthlimide was suspended in 20 ml of dimethylformamide, and 2.42 g of α,α-dibromo-m-xylene was added. The mixture was stirred overnight at room temperature, and then ethyl ether and water were added. The organic layer separated was worked up in a customary manner, and the product was purified by silica gel column chromatography [hexane / ethyl acetate=10/1] to give 0.52 g of N-(3-bromomethylbenzyl)phthalimide as a white crystalline powder.

0.50 g of the resulting bromo compound was dissolved in 20 ml of dimethylformamide, and 0.42 g of potassium carbonate, 0.21 g of potassium iodide and 0.37 g of (E)-N-ethyl-6,6-dimethyl-2-hepten-4-ynylamine hydrochloride were added. The mixture was stirred overnight at room temperature. Ethyl ether and water were added, and the organic layer separated was worked up in a customary manner. The resulting phthalimide compound was dissolved in 10 ml of tetrahydrofuran, and 0.22 ml of hydrazine hydrate was added. The mixture was stirred overnight at room temperature, and then the precipitate was removed by filtration. The filtrate was worked up in a customary manner, and the product was purified by silica gel column chromatography [ethyl acetate] to give 0.30 g of the captioned compound as a pale yellow oil.

Referential Example 48

Production of (E,E)-N-ethyl-N-(6-methoxy-6-methyl-2-hepten-4-ynyl)-5-(3-hydroxy-1-propenyl)-2 -furylmethylamine 0.36 g of 5-hydroxymethyl-2-furaldehyde was dissolved in 10 ml of ethyl ether, and under a nitrogen atmosphere, a ethyl ether solution (2 ml) of 0.25 g of phosphorus tribromide was added dropwise at 0° C. After the mixture was stirred at room temperature for 30 minutes, 0.70 g of potassium carbonate and a dimethylformamide solution (15 ml) of 0.62 g of (E)-N-ethyl-6-methoxy-6-methyl-2-hepten-4-ynylamine hydrochloride were added. The mixture was stirred overnight at room temperature, and then worked up in a customary manner. The product was purified by silica gel column chromatography [hexane/ethyl acetate=2/1] to give 0.62 g of (E)-N-ethyl-N-(6-methoxy-6-methyl-2-hepten-4-ynyl)-5-formyl-2-furylmethylamine as a pale yellow oil.

A dimethoxyethane solution (2 ml) of 200 mg of the resulting formyl compound was added to a mixture of 60% oily sodium hydride(28 mg), ethyl diethylphosphonoacetate (55 mg) and dimethoxyethane (1 ml). The mixture was stirred at room temperature for 30 minutes, and then ethyl acetate and water were added. The organic layer separated was worked up in a customary manner to give 246 mg of ethyl (E,E)-β-[5-(N-ethyl-6-methoxy-6-methyl-2-hepten-4-ynylaminomethyl)-2-furyl]acrylate.

232 mg of the resulting ester compound was dissolved in 10 ml of tetrahydrofuran, and 1.61 ml of a 1M diisobutylaluminum hydride-toluene solution was added dropwide with stirring at −40° C. After 5 ml of water and 1.6 ml of 1N hydrochloric acid were added, the mixture was stirred at room temperature for 30 minutes, and then 20 ml of a saturated aqueous solution of sodium bicarbonate was added. The mixture was stirred at room temperature for 2 hours, and ethyl ether and water were added. The organic layer separated was worked up in a customary manner, and the product was purified by silica gel column chromatography [ethyl acetate=1/1] to give 175 mg of the captioned compound as a pale yellow oil.

When ethyl (E)-3-(N-ethyl-6,6-dimethyl-2-hepten-4-ynylaminomethyl)cinnamate, prepared by using 3-hydroxymethylbenzaldehyde and (E)-N-ethyl-6,6-dimethyl-2-hepten-4-ynylamine hydrochloride instead of the starting 5-hydroxymethyl-2-furaldehyde and (E)-N-ethyl-6-methoxy-6-methyl-2-hepten-4-ynylamine hydrochloride as in Referential Example 46, is hydrolyzed with potassium hydroxide, (E)-3-(N-ethyl-6,6-dimethyl-2-hepten-4-ynylaminomethyl) cinnamic acid is obtained.

Referential Example 49

Production of
(E)-N-ethyl-N-(6-methoxy-6-methyl-2-hepten-4-ynvl)-5-hydroxymethyl-2-oxazolylmethylamine 111 mg of ethyl 2-methyloxazol-5-carboxylate [see J. Heterocyclic Chem., 17, 721 (1980)] was dissolved in 5 ml of carbon tetrachloride, 133 mg of N-bromosuccinimide and 5 mg of dibenzoyl peroxide was added. The mixture was refluxed for 3 hours under the irradiation of the artificial sun light, and then the solvent was evaporated. The residue was purified by silica gel column chromatography [hexane/ethyl acetate=3/1] to give 110 mg of ethyl 2-bromomethyloxazole-5-carboxylate as a pale yellow oil.

25 mg of the resulting brominated compound was dissolved in 1 ml of dimethylformamide, and 26 mg of (E)-N-ethyl-6-methoxy-6-methyl-2-hepten-4-ynylamine hydrochloride and 22 mg of potassium carbonate were added. The mixture was stirred overnight at room temperature and then ethyl ether and water were added. The organic layer separated was worked up in a customary manner, and the product was purified by silica gel column chromato-graphy [ethyl acetate=3/1] to give 19 mg of ethyl (E)-2-(N-ethyl-6-methoxy-6-methyl-2-hepten-4-ynylaminomethyl)oxazole-5-carboxylate as a colorless oil.

19 mg of the resulting amino compound was dissolved in 3 ml of ethanol, and 3.2 mg of sodium borohydride and 11 mg of calucium chloride was added. The mixture was stirred at room temperature for 3 hours, and then ethyl acetate and water were added. The organic layer separated was worked up in a customary manner, and the product was purified by silica gel column chromatography [ethyl acetate / hexane=3/1] to give 10 mg of the captioned compound as a colorless oil.

When the same reactions as in Referential Example 49 are carried out using ethyl 4-bromomethylthiazol-2-carboxylate [see Ann., 1981, 623] or ethyl 5-bromoethylisoxazol-3-carboxylate [synthesized by brominating ethyl 5-methylisoxazole-5-carboxylate [see J. Heterocyclic Chem., 19, 557(1982)] with N-bromosuccimide in carbon tetrachloride] insted of the starting ethyl 4-bromomethyloxazol-2-carboxylate, (E)-N-ethyl-N-(6-methoxy-6-methyl-2-hepten-4-ynyl)-2-hydroxymethyl-4-thiazolylmethylamine and (E)-N-ethyl-N-(6-methoxy-6-methyl-2-hepten-4-ynyl)-3-hydroxymethyl-5-isoxazolylmethylamine are obtained.

Referential Example 50

Production of
(E)-N-ethyl-N-(6,6-dimethyl-2-hepten-4-ynyl)-3-[2-hydroxy-3-(3-thienylmethoxy) propyl]benzylamine 62 mg of 3(3-chlromethylphenyl)-1-(3-thienylmethoxy)-2-propanol [synthesized by the epoxidation reaction of (E)-3-[3-(3-chloromethylphenyl)-2-propenyloxymethyl]thiophene with m-chloroperbenzoic acid in benzene, followed by the reduction with lithium aluminun hydride in ethyl ether] was dissolved in 1 ml of dimethylformamide, and 47 mg of (E)-N-ethyl-6,6-dimethyl-2-hepten-4-ynylamine hydrochloride, 49 mg of potassium carbonate and 3 mg of potassium iodide were added. The mixture was stirred overnight at room temperature, and then ethyl ether and water were added. The organic layer separated was worked up in a customary manner, and the product was purified by medium-pressure liquid chromatography [silica gel column, hexane/ ethyl acetate=5/1→4/1] to give 61 mg of the captioned compound as a colorless oil.

Referential Example 51

Production of
(E)-N-ethyl-N-(6,6-dimethyl-2-hepten-4-ynyl)-2-hydroxy-5-[3-(3-thienyl)phenoxy ]pentylamine 0.22 g of 1,2-epoxy-5-[3-(3-thienyl)phenoxy]pentane [synthesized by the epoxidation reaction of 3-[3-(4-pentenyloxy)phenyl]thiophene, prepared from 3-(3-thienyl)phenol and 5-bromo-1-pentene, with m-chloroperbenzoic acid in benzene] was dissolved in 4 ml of ethanol, and 0.22 g of (E)-N-ethyl-6,6-dimethyl-2-hepten-4-ynylamine hydrochloride, 0.34 ml of triethylamine were added. The mixture was refluxed for 5 hours, and then the solvent was evaporated. The residue was purified by silica gel column chromatography [chloroform / ethyl acetate=20/1] to give 0.23 g of the captioned compound as a pale yellow oil.

Effect of the Invention

Compound of the invention inhibit biosynthesis of cholesterol in mammals by inhibiting their squalene epoxidase, and thereby lower their blood cholesterol values. Thus, it can be expected that these compounds are effective as an agent for the treatment and prophylaxis of diseases caused by excess of cholesterol, for example, obesity, hyperlipemia and arteriosclerosis and heart and encephalic diseases accompanying them.

What we claim is:

1. Substituted amine derivatives represented by the following formula (I) and their nontoxic salts:

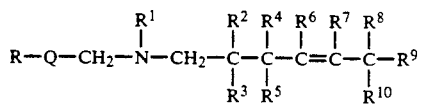

wherein
R is a thienyl group; and
Q denotes (a) a group represented by the formula

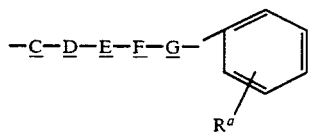

wherein C, D, E, F and G are the same or different and each denotes an oxygen atom, sulfur atom, carbonyl group, group represented by the formula —CHR$^b$—, group represented by the formula —CR$^c$= or group represented by the formula —NR$^d$—, wherein R$^b$, R$^c$ and R$^d$ are the same or different and each denotes a hydrogen atom or lower alkyl group;

R$^a$ denotes a hydrogen atom, halogen atom, hydroxyl group, cyano group, lower alkyl group or lower alkoxy group, provided that except that each pair of C and F, C and G, or D and G are the same or different and can denote oxygen atom(s), sulfur atom(s) or group(s) represented by the formula —NR$^d$—, it is impossible that at least two of C, D, E, F and G are simultaneously oxygen atom(s), sulfur atom(s) or group(s) represented by the formula —NR$^d$—, and it is impossible that at least two of C, D, E, F and G simultaneously denote carbonyl groups, and further when double bond(s) and oxygen atom(s), sulfur atom(s) or group(s) represented by the formula —NR$^d$— coexist in the chain formed by C, D, E, F and G, they do not adjoin one another; or (b) a group represented by the formula:

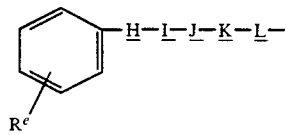

wherein H, I, J, and K are the same or different and each denotes an oxygen atom, sulfur atom, carbonyl group, group represented by the formula —CHR$^f$—, group represented by the formula —CR$^g$—= or group represented by the formula —NR$^b$—, wherein R$^f$, R$^g$ and R$^h$ are the same or different and each denotes a hydrogen atom or lower alkyl group; L denotes a carbonyl group, group represented by the formula —CHR$^i$— or group represented by the formula —CR$^j$—=, wherein R$^i$ and R$^j$ are the same or different and each denotes a hydrogen atom or lower alkyl group; and R$^e$ denotes a hydrogen atom, halogen atom, hydroxyl group, cyano group, lower alkyl group or lower alkoxy group, provided that except that H and K are the same or different and each can denote an oxygen atom, sulfur atom or group represented by the formula —NR$^h$—, it is impossible that at least two of H, I, J, and K simultaneously denote oxygen atom(s), sulfur atom(s) or group(s) represented by the formula —NR$^h$—, and it is impossible that at least two of H, I, J, and K simultaneously denote carbonyl groups, and further when double bond(s) and oxygen atom(s), sulfur atom(s) or group(s) represented by the formula —NR$^h$— coexist in the chain formed by H, I, J, K and L, they do not adjoin one another;

R$^1$ denotes a hydrogen atom, lower alkyl group, lower haloalkyl group, lower alkenyl group, lower alkynyl group or cycloalkyl group;

R$^2$, R$^3$, R$^4$ and R$^5$ are the same or different and each denotes a hydrogen atom, halogen atom or lower alkyl group, or R$^2$ and R$^4$ and/or R$^3$ and R$^5$ combine to denote a single bond;

R$^6$ and R$^7$ are the same or different and each denotes a hydrogen atom, halogen atom or lower alkyl group, or R$^6$ and R$^7$ combine to denote a single bond;

R$^8$ and R$^9$ are the same or different and each denotes a fluorine atom, trifluoromethyl group or lower alkyl group, or R$^8$ and R$^9$ combine to form a cycloalkane together with the adjacent carbon atom; and R$^{10}$ denotes a hydrogen atom, fluorine atom, trifluoromethyl group, acetoxy group, lower alkyl group or lower alkoxy group.

2. (E,E)-N-ethyl-N-(6-methoxy-6-methyl-2-hepten-4-ynyl)-3-[3-(3-thienyl)-2-propenyloxymethyl] benzylamine or pharmaceutically acceptable salt thereof.

3. A pharmaceutical composition for treating hypercholesterolemia, hyperlipemia or arteriosclerosis, comprising a pharmaceutically effective amount of a compound of formula (I) as set forth in claim 1, or a pharmaceutically acceptable salt thereof and a pharmaceutically acceptable carrier or diluent.

4. The substituted amine derivatives and their nontoxic salts of claim 1 wherein Q denotes a group represented by one of the following formula:

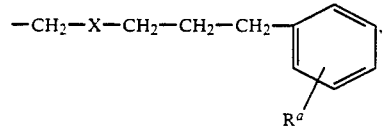

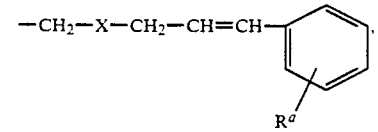

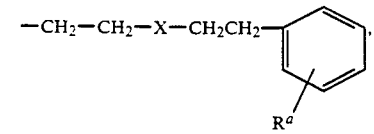

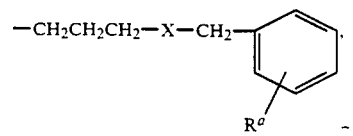

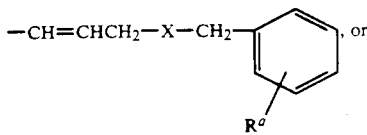

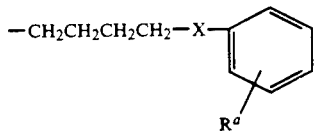

wherein X denotes an oxygen atom, sulfur atom or a group represented by the formula —NR$^d$—, wherein R$^d$ and R$^a$ are as defined above.

5. The substituted amine derivatives and their non-toxic salts of claim 1 wherein Q denotes a group represented by one of the following formula:

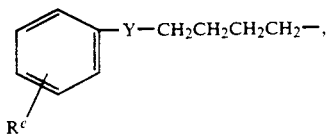

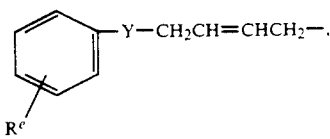

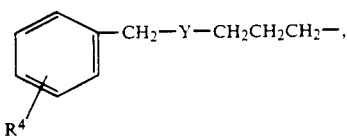

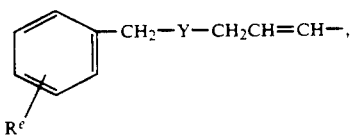

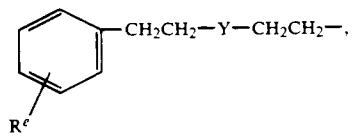

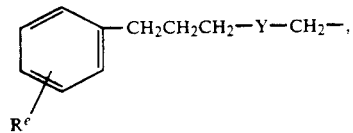

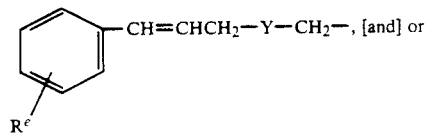

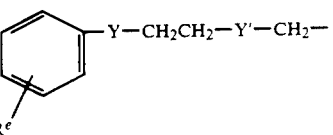

wherein Y and Y' are the same or different and each denotes an oxygen atom, sulfur atom or a group represented by the formula —NR$^d$—, wherein R$^d$ and R$^c$ are as defined above.

6. The substituted amine derivatives and their non-toxic salts of claim 1 wherein R$^1$ is a methyl, ethyl, propyl, allyl, propargyl, cyclopropyl or 2-fluoroethyl group;

R$^2$, R$^3$, R$^4$ and R$^5$ are simultaneously hydrogen atoms, or R$^2$ and R$^4$ and/or R$^3$ and R$^5$ combine to form a single bond and the remainder of R$^2$, R$^3$, R$^4$ and R$^5$ are the same or different and each represents a hydrogen atom or fluorine atom;

R$^6$ and R$^7$ are hydrogen atoms or R$^6$ and R$^7$ combine to form a single bond;

R$^8$ and R$^9$ are the same or different and each represents a fluorine atom, methyl group, ethyl group, propyl group or trifluoromethyl group, or R$^8$ and R$^9$ combine together with the adjacent carbon to form a cyclopropane ring; and R$^{10}$ is a hydrogen atom, fluorine atom, methyl group, ethyl group, propyl group, trifluoromethyl group, methoxy group, ethoxy group, propoxy group or acetoxy group.

7. The substituted amine derivatives and their non-toxic salts of claim 1 wherein R$^1$ is a methyl, ethyl, propyl, allyl, propargyl, cyclopropyl or 2-fluoroethyl group.

8. The substituted amine derivatives and their non-toxic salts of claim 1 wherein R$^2$, R$^3$, R$^4$ and R$^5$ are simultaneously hydrogen atoms, or R$^2$ and R$^4$ and/or R$^3$ and R$^5$ combine to form a single bond and the remainder of R$^2$, R$^3$, R$^4$ and R$^5$ are the same or different and hydrogen atom(s) or fluorine atom(s).

9. The substituted amine derivatives and their non-toxic salts of claim 1 wherein R$^6$ and R$^7$ are hydrogen atoms or R$^6$ and R$^7$ combine to form a single bond.

10. The substituted amine derivatives and their non-toxic salts of claim 1 wherein R$^8$ and R$^9$ are the same or different and each denotes a fluorine atom, methyl group, ethyl group, propyl group or trifluoromethyl group, or R$^8$ and R$^9$ combine togehter with the adjacent carbon to form a cyclopropane ring.

11. The substituted amine derivatives and their non-toxic salts of claim 1 wherein R$^{10}$ is a hydrogen atom, fluorine atom, methyl group, ethyl group, propyl group, trifluoromethyl group, methoxy group, ethoxy group, propoxy group or acetoxy group.

12. A method of treating or preventing hypercholesterolemia, hyperlipemia or arteriosclerosis in an individual in need of such treatment which comprises administering to said individual a therapeutically effective amount of a compound of formula (I) as set forth in claim 1 or a pharmaceutically acceptable salt thereof.

13. A squalene oxidase inhibitor comprising a compound of general formula of claim 1 or a pharmaceutically acceptable salt thereof.

* * * * *